(12) United States Patent
Al-Obeidi et al.

(10) Patent No.: US 6,794,365 B2
(45) Date of Patent: Sep. 21, 2004

(54) MALONIC ACID DERIVATIVES, PROCESSES FOR THEIR PREPARATION THEIR USE AND PHARMACEUTICAL COMPOSITIONS CONTAINING THEM

(75) Inventors: Fahad A. Al-Obeidi, Tucson, AZ (US); Armin Walser, Tucson, AZ (US); Peter Wildgoose, Oberursel (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 146 days.

(21) Appl. No.: 09/790,641

(22) Filed: Feb. 23, 2001

(65) Prior Publication Data

US 2002/0022596 A1 Feb. 21, 2002

(30) Foreign Application Priority Data

Feb. 26, 2000 (EP) .............................. 00104041

(51) Int. Cl.⁷ ................................ C07K 5/06
(52) U.S. Cl. ...................... 514/19; 514/18; 530/331; 530/332
(58) Field of Search ...................... 514/18, 19; 530/331, 530/332

(56) References Cited

U.S. PATENT DOCUMENTS

| 5,518,735 A | 5/1996 | Stürzebecher et al. | ...... 424/449 |
| 5,607,937 A | 3/1997 | Stuerzebecher et al. | .... 514/255 |

FOREIGN PATENT DOCUMENTS

| EP | 075 896 | 4/1983 |
| EP | 1 016 663 A1 | 7/2000 |
| WO | WO 92/08709 | 5/1992 |
| WO | WO 94/18185 | 8/1994 |
| WO | WO 95/29189 | 11/1995 |
| WO | WO 96/05189 | 2/1996 |
| WO | WO 97/22712 | 6/1997 |
| WO | WO 98/50420 | 11/1998 |
| WO | WO 99/33800 | 7/1999 |
| WO | WO 00/40548 | 7/2000 |
| WO | WO 00/40571 | 7/2000 |

OTHER PUBLICATIONS

Steinmetzer, T. et al, (Expert Opinion on Investigational Drugs, 10 845–64, 2001).*
Rutsch, W. et al (European Heart Journal 19 Suppl K, K11–K17, 1998).*
Oldgren, J. et al. (European Heart Journal 20 1657–66, 1999).*
Thomas (Thrombosis and Haemostasis 47, 244, 1982).*
S. F. Brady, et al. "Amide and α–Keto Carbonyl Inhibitors of Thrombin Based on Arginine and Lysine: Synthesis, Stability and Biological Characterization" *Bioorganic and Medicinal Chemistry*, 3(8):1063–1078 (1995).
D. M. Jones, et al. "Thrombin Inhibitors Based on Ketone Derivatives of Arginine and Lysine" *J. Enzyme Inhibition* 9:43–60 (1995).
M. R. Wiley, et al. "D–PHE–PRO–p–Amidinobenzylamine: A Potent and Highly Selective Thrombin Inhibitor" *Bioorganic & Medicinal Chemistry Letters* 6(20):2387–2392 (1996).
Jörg Stürzebecher, et al."Structure–Activity Relationships of Inhibitors Derived From 3–Amidinophenylalanine" *J. Enzyme Inhibition* 9:87–99 (1995).
B. Voigt, et al. "Synthese von Nα–(Arylsulfonyl)–4–amidino–phenylalanyl–prolinen und von Nα–(Arylsulfonylglycyl)–4–amidino–phenylalanyl–prolinen und deren Prüfung als Inhibitoren von Serinproteinasen" *Pharmazie* 43:412–414 (1988)* English Abstract at p. 412.

* cited by examiner

Primary Examiner—Christopher S. F. Low
Assistant Examiner—David Lukton
(74) Attorney, Agent, or Firm—Finnegan, Henderson, Farabow, Garrett & Dunner, L.L.P.

(57) ABSTRACT

The present invention relates to new malonic acid derivatives of the formula I,

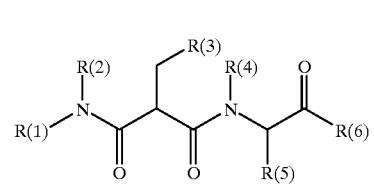

(I)

wherein R(1), R(2), R(3), R(4), R(5), and R(6) have the meanings indicated in the claims. The compounds of formula I are inhibitors of the blood clotting enzyme factor Xa. The invention also relates to processes for the preparation of the compounds of formula I, to methods of inhibiting factor Xa activity and of inhibiting blood clotting, to the use of the compounds of formula I in the treatment and prophylaxis of diseases, which can be treated or prevented by the inhibition of factor Xa activity such as thromboembolic diseases, and to the use of the compounds of formula I in the preparation of medicaments to be applied in such diseases. The invention further relates to compositions containing a compound of formula I in admixture or otherwise in association with an inert carrier, in particular pharmaceutical compositions containing a compound of formula I together with pharmaceutically acceptable carrier substances and auxiliary substances.

31 Claims, No Drawings

MALONIC ACID DERIVATIVES, PROCESSES FOR THEIR PREPARATION THEIR USE AND PHARMACEUTICAL COMPOSITIONS CONTAINING THEM

The present invention relates to compounds of the formula I,

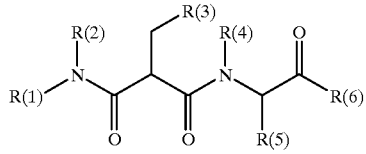
(I)

in which R(1), R(2), R(3), R(4), R(5), and R(6) have the meanings as indicated below. The compounds of formula I are valuable pharmacologically active compounds. They exhibit an antithrombotic effect and are suitable, for example, for the therapy and prophylaxis of cardiovascular disorders like thromboembolic diseases or restenoses. They are reversible inhibitors of the blood clotting enzyme factor Xa and can in general be applied in conditions in which an undesired activity of factor Xa is present or for the cure or prevention of which an inhibition of factor Xa is intended. The invention also relates to processes for the preparation of the compounds of formula I, to methods of inhibiting factor Xa activity and of inhibiting blood clotting, to the use of the compounds of formula I in the treatment and prophylaxis of diseases which can be treated or prevented by the inhibition of factor Xa activity such as thromboembolic diseases, and to the use of the compounds of formula I in the preparation of medicaments to be applied in such diseases. The invention further relates to compositions containing a compound of formula I in admixture or otherwise in association with an inert carrier, as well as pharmaceutical compositions containing a compound of formula I together with pharmaceutically acceptable carrier substances and auxiliary substances.

The ability to form blood clots is vital to survival. In certain disease states, however, the formation of blood clots within the circulatory system reaches an undesired extent and is itself a source of morbidity potentially leading to pathological consequences. It is nevertheless not desirable in such disease states to completely inhibit the clotting system because life threatening hemorrhage would ensue. In the treatment of such states a well-balanced intervention into the blood clotting system is required, and there is still a need for substances exhibiting a suitable pharmacological activity profile for achieving such a result.

Blood coagulation is a complex process involving a progressively amplified series of enzyme activation reactions in which plasma zymogens are sequentially activated by limited proteolysis. Mechanistically the blood coagulation cascade has been divided into intrinsic and extrinsic pathways, which converge at the activation of factor X. Subsequent generation of the thrombin proceeds through a single common pathway (see Scheme 1).

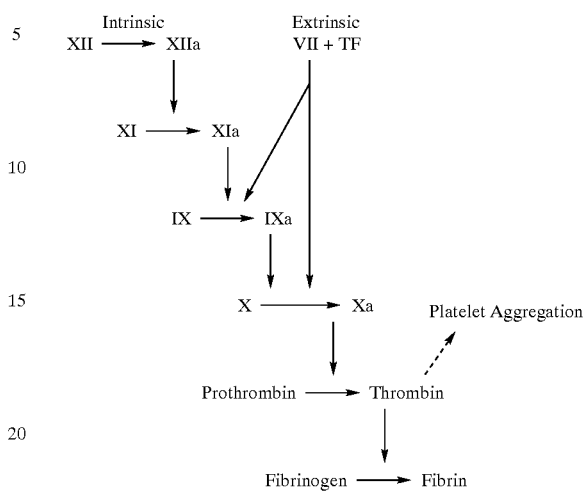

Present evidence suggests that the intrinsic pathway plays an important role in the maintenance and growth of fibrin formation, while the extrinsic pathway is critical in the initiation phase of blood coagulation. It is generally accepted that blood coagulation is physically initiated upon formation of a tissue factor (TF)/factor VIIa complex. Once formed, this complex rapidly initiates coagulation by activating factors IX and X. The newly generated activated factor X, i.e. factor Xa, then forms a one-to-one complex with factor Va and phospholipids to form a prothrombinase complex, which is responsible for converting soluble fibrinogen to insoluble fibrin via the activation of thrombin from its precursor prothrombin. As time progresses, the activity of the factor VIIa/tissue factor complex (extrinsic pathway) is suppressed by a Kunitz-type protease inhibitor protein, TFPI, which, when complexed to factor Xa, can directly inhibit the proteolytic activity of factor VIIa/tissue factor. In order to maintain the coagulation process in the presence of an inhibited extrinsic system, additional factor Xa is produced via the thrombin-mediated activity of the intrinsic pathway. Thus, thrombin plays a dual autocatalytic role, mediating its own production and the conversion of fibrinogen to fibrin.

The autocatalytic nature of thrombin generation is an important safeguard against uncontrolled bleeding and it ensures that, once a given threshold level of prothrombinase is present, blood coagulation will proceed to completion, effecting, for example, an end of the hemorrhage. Thus, it is most desirable to develop agents that inhibit coagulation without directly inhibiting thrombin but by inhibiting other steps in the coagulation cascade like factor Xa.

In many clinical applications there is a great need for the prevention of intravascular blood clots or for anti-coagulant therapy. For example, nearly 50% of patients who have undergone a total hip replacement develop deep vein thrombosis (DVT). The currently approved therapies are fixed dose low molecular weight heparin (LMWH) and variable dose heparin. Even with these drug regimes 10% to 20% of patients develop DVT and 5% to 10% develop bleeding complications.

Another clinical situation for which better anticoagulants are needed concerns subjects undergoing transluminal coronary angioplasty and subjects at risk for myocardial infarction or angina. The present, conventionally accepted therapy which consists of administering heparin and aspirin, is associated with a 6% to 8% abrupt vessel closure rate with 24 hours of the procedure. The rate of bleeding complications requiring transfusion therapy due to the use of heparin also is approximately 7%. Moreover, even though delayed closures are significant, administration of heparin after termination of the procedures is of little value and can be detrimental.

The most widely used blood-clotting inhibitors are heparin and the related sulfated polysaccharides, LMWH and heparin sulfate. These molecules exert their anti-clotting effects by promoting the binding of a natural regulator of the clotting process, anti-thrombin III, to thrombin and to factor Xa. The inhibitory activity of heparin primarily is directed toward thrombin, which is inactivated approximately 100 times faster than factor Xa. Although relative to heparin, heparin sulfate and LMWH are somewhat more potent inhibitors of Xa than of thrombin, the differences in vitro are modest (3–30 fold) and effects in vivo can be inconsequential. Hirudin and hirulog are two additional thrombin-specific anticoagulants that have been tested in clinical trials. However, these anticoagulants, which inhibit thrombin, also are associated with bleeding complications.

Preclinical studies in baboons and dogs have shown that specific inhibitors of factor Xa prevent clot formation without producing the bleeding side effects observed with direct thrombin inhibitors.

Several specific inhibitors of factor Xa have been reported. Both synthetic and protein inhibitors of factor Xa have been identified, these include, for example, antistasin ("ATS") and tick anticoagulant peptide ("TAP"). ATS, which is isolated from the leech, *Haementerin officinalis*, contains 119 amino acids and has a Ki for factor Xa of 0.05 nM. TAP, which is isolated from the tick, *Ornithodoros moubata*, contains 60 amino acids and has a Ki for factor Xa of about 0.5 nM.

The effectiveness of recombinantly-produced ATS and TAP have been investigated in a number of animal model systems. Both inhibitors decrease bleeding time compared to other anticoagulants, and prevent clotting in a thromboplastin-induced, ligated jugular vein model of deep vein thrombosis. The results achieved in this model correlate with results obtained using the current drug of choice, heparin.

Subcutaneous ATS also was found to be an effective treatment in a thromboplastin-induced model of disseminated intravascular coagulation (DIC). TAP effectively prevents "high-shear" arterial thrombosis and "reduced flow" caused by the surgical placement of a polyester (DACRON®) graft at levels that produced a clinically acceptable prolongation of the activated partial thromboplastin time (aPTT), i.e. less than about two fold prolongation. By comparison, standard heparin, even at doses causing a five fold increase in the aPTT, did not prevent thrombosis and reduced flow within the graft. The aPTT is a clinical assay of coagulation which is particularly sensitive to thrombin inhibitors.

ATS and TAP have not been developed clinically. One major disadvantage of these two inhibitors is that administration of the required repeated doses causes the generation of neutralizing antibodies, thus limiting their potential clinical use. Moreover, the sizes of TAP and ATS render oral administration impossible, further restricting the number of patients able to benefit from these agents.

A specific inhibitor of factor Xa with a favourable property profile would have substantial practical value in the practice of medicine. In particular, a factor Xa inhibitor would be effective under circumstances where the present drugs of choice, heparin and related sulfated polysaccharides, are ineffective or only marginally effective.

Low molecular weight, factor Xa-specific blood clotting inhibitors, that are effective but do not cause unwanted side effects have been described, for example, in WO-A 95/29189). Indole derivatives as low molecular weight, factor Xa-specific blood clotting inhibitors have been described in WO-A-99/33800. However, besides being an effective factor Xa-specific blood clotting inhibitor, it is desirable that such inhibitors also have further advantageous pharmacological properties, for instance good oral bioavailabilty, high stability in plasma and liver and/or high selectivity versus other serine proteases whose inhibition is not intended, such as thrombin. Thus there exists an ongoing need for further low molecular weight factor Xa-specific blood clotting inhibitors which are effective and have the above advantages as well. Arylalkanoyl and malonic acid derivatives, which are suitable Factor Xa inhibitors have been proposed in European application nos. 99100001, 99100002, 99119537, and 99119538.

The present invention also satisfies the above needs by providing novel compounds of the formula I which exhibit factor Xa inhibitory activity and are favourable agents for inhibiting unwanted blood clotting and thrombus formation.

Thus, a subject of the present invention are compounds of the formula I,

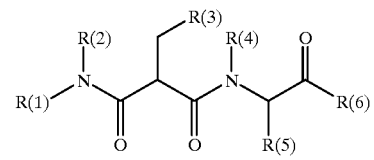

(I)

where

R(1) is hydrogen, $(C_1-C_6)$-alkyl, $(C_2-C_6)$-alkenyl, $(C_6-C_{10})$-aryl, $(C_6-C_{10})$-aryl-$(C_1-C_4)$-alkyl, where aryl in aryl-alkyl is unsubstituted or substituted by R(17);

R(2) is hydrogen or $(C_1-C_4)$-alkyl;

R(3) is $(C_6-C_{10})$-aryl which is substituted by R(7);

R(4) is hydrogen or $(C_1-C_4)$-alkyl;

R(5) is $(C_1-C_6)$-alkyl, $(C_3-C_7)$-cycloalkyl, $(C_3-C_7)$-cycloalkyl-$(C_1-C_4)$-alkyl, $(C_6-C_{10})$-aryl, $(C_6-C_{10})$-aryl-$(C_1-C_4)$-alkyl, where aryl in aryl-alkyl is unsubstituted or substituted by a residue R(20), and where alkyl is unsubstituted or substituted by a residue R(21); or R(4) and R(5) together form a residue of the formula II

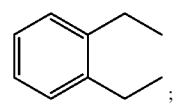

(II)

R(6) is NR(8)R(9) or OR(22);

R(7) is R(17) or R(20);

R(8) is hydrogen; $(C_1-C_4)$-alkyl, where alkyl is unsubstituted or substituted by a residue R(20); heteroaryl-$(C_1-C_4)$-alkyl; $(C_6-C_{10})$-aryl-$(C_1-C_4)$-alkyl, where aryl is unsubstituted or substituted by a residue R(17);

R(9) is $(C_6-C_{10})$-aryl-$(C_1-C_4)$-alkyl,

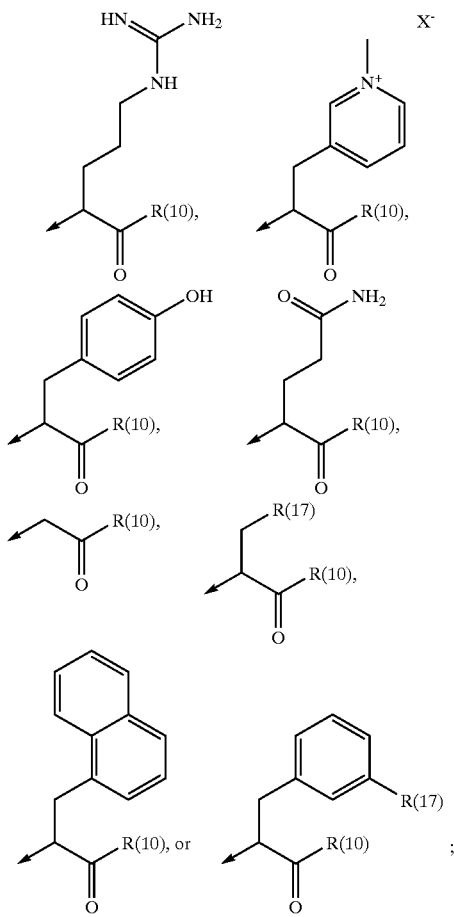

R(10) is NR(12)R(13), OR(14), or

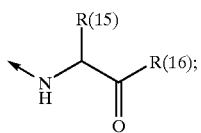

R(12) is hydrogen or $(C_1-C_4)$-alkyl;
R(13) is hydrogen, $(C_6-C_{10})$-aryl-$(C_1-C_4)$-alkyl, or $(C_1-C_4)$-alkyl;
R(14) is hydrogen, $(C_1-C_4)$-alkyl, $(C_2-C_4)$-alkenyl or $(C_6-C_{10})$-aryl-$(C_1-C_4)$-alkyl;
R(15) is $(C_3-C_7)$-cycloalkyl-$(C_1-C_4)$-alkyl;
R(16) is R(20);
R(17) is —C(=N—R(18))-N(R(19))$_2$;
R(18) is hydrogen, hydroxy, or an amino protective group;
R(19) is hydrogen, $(C_1-C_4)$-alkyl, $(C_6-C_{10})$-aryl-$(C_1-C_4)$-alkoxycarbonyl, or an amino protective group;
R(20) is N(R(19))$_2$;
R(21) is hydroxy, $(C_6-C_{10})$-aryl-$(C_1-C_4)$-alkoxy, $(C_6-C_{10})$-aryl-$(C_1-C_4)$-alkoxycarbonylamino, carboxyl, or R(20);
R(22) is hydrogen or $(C_1-C_4)$-alkyl;
X$^-$ is a physiologically acceptable anion;
in all their stereoisomeric forms and mixtures thereof in any ratio, and their physiologically acceptable salts.

Alkyl residues present in the compounds of formula I can be saturated or unsaturated (and therefore cover alkenyl or alkynyl residues) and straight-chain or branched. This also applies when they carry substituents or appear as substituents in other residues such as for example, in alkoxy residues, arylalkoxy residues, alkoxycarbonyl residues, cycloalkyl-alkyl residues, arylalkyl residues, heteroarylalkyl residues, and arylalkoxycarbonyl residues. Examples of saturated alkyl residues are methyl, ethyl, n-propyl, n-butyl, isopropyl, isobutyl, sec-butyl, and tert-butyl, n-pentyl, n-hexyl, isopentyl, isohexyl, neopentyl, 3-methylpentyl, and tert-pentyl, examples of unsaturated alkyl residues are vinyl, 1-propenyl, 2-propenyl (i. e. allyl), butenyl, 3-methyl-2-butenyl, pentenyl, hexenyl, (alkenyl residues) or ethynyl, 1-propynyl, 2-propynyl (i. e. propargyl), butynyl, pentynyl and hexynyl (alkynyl residues).

Cycloalkyl residues present in the compounds of formula I can be mono-, di- or tricyclic and are connected in the ring. This also applies when they appear as substituents in other residues. Examples of cycloalkyl residues are cyclopropyl, methyl-cyclopropyl, ethyl-cyclopropyl, dimethyl-cyclopropyl, propyl-cyclopropyl, methyl-ethyl-cyclopropyl, butyl-cyclopropyl, methyl-propyl-cyclopropyl, diethyl-cyclopropyl, cyclobutyl, methyl-cyclobutyl, ethyl-cyclobutyl, cyclopentyl, methyl-cyclopentyl, ethyl-cyclopentyl, dimethyl-cyclopentyl, cyclohexyl, methyl-cyclohexyl, and cycloheptyl, where ethyl, propyl, and butyl, can be straight-chain or branched as described above.

Examples of aryl are phenyl or naphthyl.

Arylalkyl residues present in the compounds of formula I can consist of an alkyl residue, which can contain one to three aryl moieties. Examples of arylalkyl residues are phenyl-methyl, phenyl-ethyl, phenyl-propyl, phenyl-butyl, naphthyl-methyl, naphthyl-ethyl, naphthyl-propyl, naphthyl-butyl, diphenyl-methyl, diphenyl-ethyl, diphenyl-propyl, diphenyl-butyl, naphthyl-phenyl-methyl, naphthyl-phenyl-butyl, dinaphthyl-butyl, and triphenyl-ethyl.

Examples of heteroaryl residues are pyridyl, pyridazinyl, pyrimidyl, pyrazinyl, furanyl, pyrrolyl, imidazolyl, 1H-pyrazolyl, thiazolyl, oxazolyl, thiophenyl, 1H-benzoimidazolyl, benzothiazolyl, benzofuranyl, indolyl, thieno[3,2-c]pyridinyl, thieno[2,3-c]pyridinyl, furo[3,2-c]pyridinyl, furo[2,3-c]pyridinyl, 3H-imidazo[4,5-c]pyridinyl, [1,2,4]oxadiazolyl, quinolinyl, and isoquinolinyl. The residues can be bound at every possible position.

Examples of pyridyl residues are 2-pyridyl, 3-pyridyl and 4-pyridyl. This also applies to pyridyl residues in which the nitrogen atom is substituted by an alkyl group etc. this substitution leading to a positively charged pyridinium group. This pyridinium group has an X$^-$ as counterion.

In monosubstituted phenyl residues the substituent can be located in the 2-position, the 3-position or the 4-position.

Naphthyl residues can be 1-naphthyl and 2-naphthyl. In substituted naphthyl residues the substituents can be in any position, i. e. in monosubstituted 1-naphthyl residues in the 2-, 3-, 4-, 5-, 6-, 7-, or 8-position and in monosubstitued 2-naphthyl residues in the 1-, 3-, 4-, 5-, 6-, 7-, or 8-position.

An example of an $(C_6-C_{10})$-aryl-$(C_1-C_4)$-alkyl residue in compounds of formula I is benzyl (phenylmethyl).

Suitable amino protective groups are known to those skilled in the art and encompass for example those which are customarily used in peptide synthesis. Suitable amino protective groups in the residues R(18) and R(19) can be for example the following residues:

$(C_1-C_6)$-alkyl, $(C_1-C_6)$-alkylcarbonyl, $(C_1-C_6)$-alkoxycarbonyl, $(C_1-C_{18})$-alkylcarbonyloxy-$(C_1-C_6)$-alkoxycarbonyl, optionally substituted $(C_6-C_{14})$- arylcarbonyl, optionally substituted $(C_6-C_{14})$-aryloxycarbonyl, $(C_6-C_{14})$-aryl-$(C_1-C_6)$-alkoxycarbonyl which can also be substituted in the aryl moiety; cyano, nitro, amino, hydroxy, $(C_1-C_6)$-alkoxy, and $(C_6-C_{14})$-aryl-$(C_1-C_6)$-alkoxy which is unsubstituted or substituted in the aryl moiety for example by $(C_1-C_4)$-alkoxy, preferably methoxy, chloro, or $(C_1-C_4)$-alkyl, preferably methyl.

$(C_1-C_3)$-alkyl means alkyl having 1, 2, or 3 carbon atoms.

$(C_1-C_4)$-alkyl means alkyl having 1, 2, 3, or 4 carbon atoms.

$(C_1-C_6)$-alkyl means alkyl having 1, 2, 3, 4, 5, or 6 carbon atoms.

$(C_2-C_4)$-alkenyl means alkenyl having 2, 3, or 4 carbon atoms.

$(C_2-C_6)$-alkenyl means alkenyl having 2, 3, 4, 5, or 6 carbon atoms.

$(C_6-C_{10})$-aryl means aryl having 6, 7, 8, 9, or 10 carbon atoms.

$(C_6-C_{14})$-aryl means aryl having 6, 7, 8, 9, 10, 11, 12, 13, or 14 carbon atoms.

$(C_1-C_4)$-alkoxy means alkoxy having 1, 2, 3, or 4 carbon atoms.

$(C_1-C_6)$-alkoxy means alkoxy having 1, 2, 3, 4, 5, or 6 carbon atoms.

$(C_1-C_6)$-alkoxycarbonyl means alkoxycarbonyl having 1, 2, 3, 4, 5, or 6 carbon atoms in the alkoxy part.

$(C_1-C_6)$-alkylcarbonyl means alkylcarbonyl having 1, 2, 3, 4, 5, or 6 carbon atoms in the alkyl part.

$(C_6-C_{10})$-aryl-$(C_1-C_4)$-alkyl means aryl-alkyl having independently from each other 6, 7, 8, 9, or 10 carbon atoms in the aryl part and 1, 2, 3, or 4 carbon atoms in the alkyl part.

$(C_6-C_{14})$-aryl-$(C_1-C_6)$-alkoxy means aryl-alkoxy having independently from each other 6, 7, 8, 9, 10, 11, 12, 13, or 14 carbon atoms in the aryl part and 1, 2, 3, 4, 5, or 6 carbon atoms in the alkoxy part.$(C_6-C_{10})$-aryl-$(C_1-C_4)$-alkoxy means aryl-alkoxy having independently from each other 6, 7, 8, 9, or 10 carbon atoms in the aryl part and 1, 2, 3, or 4 carbon atoms in the alkoxy part.

Heteroaryl-$(C_1-C_4)$-alkyl means heteroaryl-alkyl having 1, 2, 3, or 4 carbon atoms in the alkyl part.

$(C_1-C_{18})$-alkylcarbonyloxy-$(C_1-C_6)$-alkoxycarbonyl means alkylcarbonyloxy-alkoxycarbonyl having independently from each other 1, 2, 3, 4, 5, 6, 7, 8, 9, 10, 11, 12, 13, 14, 15, 16, 17, or 18 carbon atoms in the alkyl part and 1, 2, 3, 4, 5, or 6 carbon atoms in the alkoxy part.

$(C_6-C_{14})$-arylcarbonyl means arylcarbonyl having 6, 7, 8, 9, 10, 11, 12, 13, or 14 carbon atoms in the aryl part.

$(C_6-C_{14})$-aryloxycarbonyl means aryloxycarbonyl having 6, 7, 8, 9, 10, 11, 12, 13, or 14 carbon atoms in the aryl part.

$(C_6-C_{14})$-aryl-$(C_1-C_6)$-alkoxy means aryl-alkoxy having independently from each other 6, 7, 8, 9, 10, 11, 12, 13, or 14 carbon atoms in the aryl part and 1, 2, 3, 4, 5, or 6 carbon atoms in the alkoxy part.

$(C_6-C_{14})$-aryl-$(C_1-C_6)$-alkoxycarbonyl means aryl-alkoxycarbonyl having independently from each other 6, 7, 8, 9, 10, 11, 12, 13, or 14 carbon atoms in the aryl part and 1, 2, 3, 4, 5, or 6 carbon atoms in the alkoxy part.

$(C_6-C_{10})$-aryl-$(C_1-C_4)$-alkoxycarbonyl means aryl-alkoxycarbonyl having independently from each other 6, 7, 8, 9, or 10 carbon atoms in the aryl part and 1, 2, 3, or 4 carbon atoms in the alkoxy part.

$(C_3-C_7)$-cycloalkyl means cycloalkyl having 3, 4, 5, 6, or 7 carbon atoms.

$(C_3-C_7)$-cycloalkyl-$(C_1-C_4)$-alkyl means cycloalkyl-alkyl having independently from each other 3, 4, 5, 6, or 7 carbon atoms in the cycloalkyl part and 1, 2, 3, or 4 carbon atoms in the alkyl part.

It is understood that residues present more that one time in a compound of formula I, e.g. the residues R(17), R(18), R(19), R(20) and R(21), are independent of one another and can be identical or different.

Physiologically acceptable anions $X^-$, which are present in the compounds of formula I if a positively charged group is present, can be anions derived from suitable inorganic acids or organic carboxylic acids or sulfonic acids. Suitable acids are pharmaceutically utilizable or non-toxic salts. Examples of such acids are those given below as examples of acids which can form physiologically acceptable salts with the compounds of formula I containing basic groups. If a compound of formula I contains an anion $X^-$ and simultaneously is present as an acid addition salt formed at a basic group, the anion $X^-$ can be the same or different as the anion introduced by salt formation. The present invention also covers inner salts (or betaines) of the compounds of formula I.

Physiologically acceptable salts of the compounds of formula I are pharmaceutically utilizable or non-toxic salts. Such salts are formed, for example, from compounds of formula I which contain acid groups, for example carboxylic acid groups. Examples of such salts are, for example, salts containing cations of alkali metals or alkaline earth metals, such as, for example, sodium, potassium, magnesium or calcium, or the unsubstituted ammonium cation or organic ammonium cations, the latter including cations obtained from physiologically acceptable organic amines, such as, for example, methylamine, ethylamine, triethylamine, ethanolamine, tris(2-hydroxyethyl)amine or amino acids by protonation, or suitable quaternary ammonium cations like, for example, tetramethylammonium.

Compounds of formula I which contain basic groups, for example an amino group or an amidino group, form acid addition salts with, for example, inorganic acids, organic carboxylic and organic sulfonic acids. Examples of such acids, the anions of which can be present in physiologically acceptable salts of the compounds of formula I, are hydrochloric acid, hydrobromic acid, sulfuric acid, phosphoric acid, acetic acid, benzoic acid, oxalic acid, malonic acid, succinic acid, maleic acid, fumaric acid, malic acid, tartaric acid, citric acid, methanesulfonic acid, p-toluenesulfonic acid or naphthalenesulfonic acids.

Physiologically acceptable salts of the compounds of formula I can be prepared according to standard procedures, for example by combining the compound of formula I with the desired base, for example an alkaline metal hydroxide or carbonate or hydrogen carbonate or an amine, or with the desired acid in a solvent or diluent. A physiologically acceptable salt of a compound of formula I can also be prepared from another salt, for example trifluoroacetic acid salt by cation exchange or anion exchange by standard procedures. The present invention also covers in general salts of the compounds of formula I which are, for example, obtained during the chemical synthesis of the compounds and which can be used as starting materials for the subsequent preparation of a desired physiologically acceptable salt. The present invention further covers solvates of the compounds of formula I, for example hydrates or alcoholates.

The compounds of formula I according to the invention can contain optically active carbon atoms which independently of one another can have R or S configuration. They can thus be present in the form of individual enantiomers or individual diastereomers or in the form of enantiomeric mixtures including racemates, or diastereomeric mixtures. The present invention relates both to pure enantiomers and mixtures of enantiomers in all ratios and to pure diastereomers and mixtures of diastereomers in all ratios. The invention covers mixtures of two stereoisomers as well as mixtures of more than two stereoisomers of formula I, and all ratios of stereoisomers in the mixtures.

The compounds of formula I can also be present as E isomers or Z isomers. The present invention relates to both pure E and Z isomers and to mixtures of E/Z isomers in all ratios. Diastereomers, including E/Z isomers, can be separated into the individual isomers, for example, by chromatography. Racemates can be separated into the two enantiomers by chromatography on chiral phases or by resolution according to standard procedures. Pure enantiomers can otherwise also be obtained by employing into the synthesis optically active starting materials.

The compounds of formula I according to the invention can further contain mobile hydrogen atoms, i.e. they can be present in various tautomeric forms. The present invention also relates to all these tautomers.

The invention also includes derivatives and modifications of the compounds of the formula I, for example prodrugs, protected forms and other physiologically tolerable derivatives including esters and amides, as well as active metabolites of the compounds of the formula I. Such esters and amides are, for example, ($C_1$–$C_4$)-alkyl esters, unsubstituted amides or ($C_1$–$C_8$)-alkylamides. The invention relates in particular to prodrugs and protected forms of the compounds of the formula I which can be converted into compounds of the formula I under physiological conditions. Suitable prodrugs for the compounds of the formula I, i. e. chemically modified derivatives of the compounds of the formula I having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115–130; or H. Bundgaard, Drugs of the Future 16 (1991) 443 which are all incorporated herein by reference. Suitable prodrugs for the compounds of the formula I are, for example, ester prodrugs and amide prodrugs of carboxylic acid groups, and also acyl prodrugs and carbamate prodrugs of acylatable nitrogen-containing groups such as amino group, amidino group and the guanidino group. In the acyl prodrugs and carbamate prodrugs one or more, for example one or two, hydrogen atoms on nitrogen atoms in such groups are replaced with an acyl group or an oxyacyl group. Suitable acyl groups and oxyacyl groups for acyl prodrugs and carbamate prodrugs are, for example, the groups $R^{p1}$—CO— and $R^{p2}$O—CO—, in which $R^{p1}$ is hydrogen, ($C_1$–$C_{18}$)-alkyl, ($C_3$–$C_7$)-cycloalkyl, ($C_3$–$C_7$)-cycloalkyl-($C_1$–$C_4$)-alkyl-, ($C_6$–$C_{14}$)-aryl which is unsubstituted or substituted by a residue ($C_1$–$C_2$)-alkyl, ($C_1$–$C_2$)-alkoxy, fluoro, or chloro; heteroaryl-, ($C_6$–$C_{14}$)-aryl-($C_1$–$C_4$)-alkyl-where aryl is unsubstituted or substituted by a residue ($C_1$–$C_2$)-alkyl, ($C_1$–$C_2$)-alkoxy, fluoro, or chloro; or heteroaryl-($C_1$–$C_4$)-alkyl- and in which $R^{p2}$ has the meanings indicated for $R^{p1}$ with the exception of hydrogen.

In one embodiment of the present invention, compounds are of the formula I, wherein
R(1) is hydrogen, ($C_1$–$C_4$)-alkyl, allyl, phenyl, benzyl, or 4-carbamimidoyl-benzyl;
R(2) is hydrogen or ($C_1$–$C_4$)-alkyl;
R(3) is phenyl or naphthyl, such as 2-naphthyl, which is substituted by R(7);
R(4) is hydrogen or methyl;

R(5) is n-butyl, sec-butyl, tert-butyl, cyclohexyl, cyclohexylmethyl, phenyl, benzyl, 2-phenyl-ethyl, 1-naphthylmethyl, 2-naphthylmethyl, aminobenzyl, such as 4-aminobenzyl, hydroxymethyl, benzyloxymethyl, carboxymethyl, 2-carboxy-ethyl, 3-amino-propyl, or 4-(benzyloxycarbonylamino)-butyl; or R(4) and R(5) together form a residue of the formula II

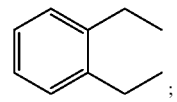

(II)

;

R(6) is NR(8)R(9), OH, or $OCH_3$;

R(7) is amidino, hydroxyamidino, amino, or dimethylamino;

R(8) is hydrogen, pyridylmethyl, such as 4-pyridylmethyl, 3-carbamimidoylbenzyl, or 4-aminobutyl;

R(9) is naphthylmethyl, such as 1-naphthylmethyl,

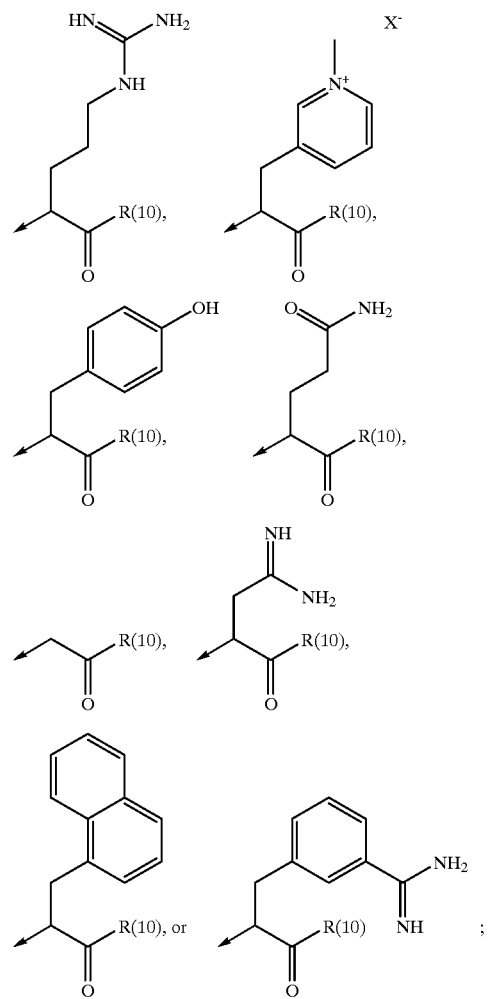

;

R(10) is NR(12)R(13), OR(14) or

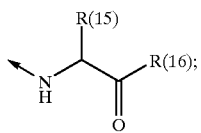

R(12) is hydrogen or methyl;

R(13) is hydrogen, phenyl-$(C_1-C_2)$-alkyl, or methyl;

R(14) is hydrogen, $(C_1-C_2)$-alkyl, benzyl, or allyl;

R(15) is cyclohexylmethyl;

R(16) is amino;

$X^-$ is a physiologically acceptable anion;

in all their stereoisomeric forms and mixtures thereof in any ratio, and their physiologically acceptable salts.

In another embodiment of the present invention, compounds are of the formula I where R(1) is hydrogen, $(C_1-C_3)$-alkyl, allyl, phenyl, benzyl, or 4-carbamimidoyl-benzyl;

R(2) is hydrogen or $(C_1-C_3)$-alkyl;

R(3) is phenyl or 2-naphthyl, which is substituted by R(7);

R(4) is hydrogen or methyl;

R(5) is n-butyl, sec-butyl, tert-butyl, cyclohexyl, cyclohexylmethyl, phenyl, benzyl, 2-phenyl-ethyl, 1-naphthylmethyl, 2-naphthylmethyl, 4-aminobenzyl, hydroxymethyl, benzyloxymethyl, carboxymethyl, 2-carboxy-ethyl, 3-amino-propyl, or 4-(benzyloxycarbonylamino)-butyl; or R(4) and R(5) together form a residue of the formula II

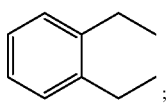

(II)

R(6) is NR(8)R(9), OH, or $OCH_3$;

R(7) is amidino, hydroxyamidino, or dimethylamino;

R(8) is hydrogen, pyridylmethyl, such as 4-pyridylmethyl, 3-carbamimidoylbenzyl, or 4-aminobutyl;

R(9) is naphthylmethyl, such as 1-naphthylmethyl,

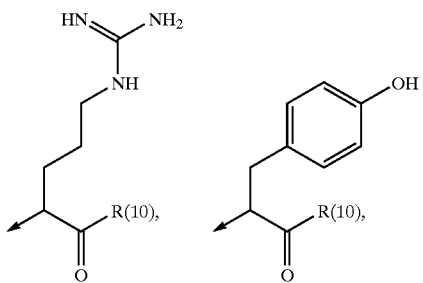

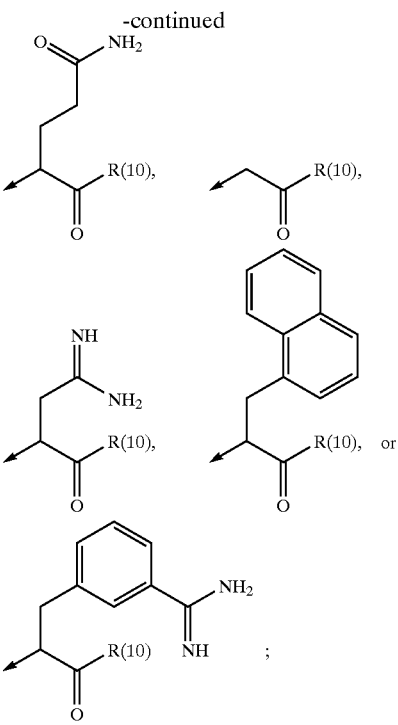

R(10) is NR(12)R(13), OR(14), or

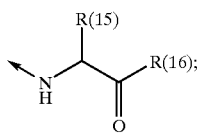

R(12) is hydrogen or methyl;

R(13) is hydrogen, phenyl-$(C_1-C_2)$-alkyl, or methyl;

R(14) is hydrogen, $(C_1-C_2)$-alkyl, benzyl, or allyl;

R(15) is cyclohexylmethyl;

R(16) is amino;

in all their stereoisomeric forms and mixtures thereof in any ratio, and their physiologically acceptable salts.

In another embodiment, compounds are of the formula I, where

R(1) is hydrogen, $(C_1-C_3)$-alkyl, allyl, phenyl, benzyl, or 4-carbamimidoyl-benzyl;

R(2) is hydrogen or $(C_1-C_3)$-alkyl;

R(3) is phenyl or naphthyl, such as 2-naphthyl, which is substituted by R(7);

R(4) is hydrogen or methyl;

R(5) is n-butyl, sec-butyl, tert-butyl, cyclohexyl, cyclohexylmethyl, phenyl, benzyl, 2-phenyl-ethyl, 1-naphthylmethyl, 2-naphthylmethyl, aminobenzyl, such as 4-aminobenzyl, hydroxymethyl, benzyloxymethyl, carboxymethyl, 2-carboxy-ethyl, 3-amino-propyl, or 4-(benzyloxycarbonylamino)-butyl; or R(4) and R(5) together form a residue of the formula II

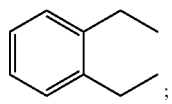
(II)

R(6) is NR(8)R(9), OH, or OCH$_3$;
R(7) is amidino, hydroxyamidino, or dimethylamino;
R(8) is hydrogen, pyridylmethyl, such as 4-pyridylmethyl, 3-carbamimidoylbenzyl, or 4-aminobutyl;
R(9) is naphthylmethyl, such as 1-naphthylmethyl,

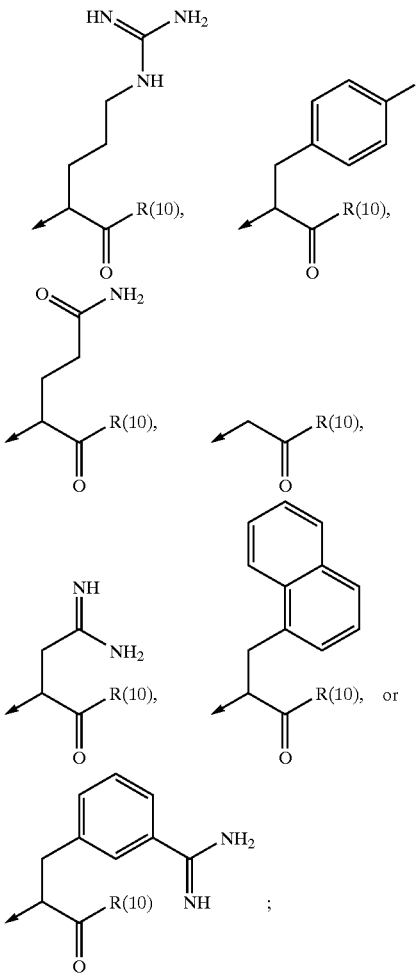

R(10) is NR(12)R(13), or OR(14);
R(12) is hydrogen or methyl;
R(13) is hydrogen, phenyl-(C$_1$–C$_2$)-alkyl, or methyl;
R(14) is hydrogen, (C$_1$–C$_2$)-alkyl, benzyl, or allyl;
in all their stereoisomeric forms and mixtures thereof in any ratio, and their physiologically acceptable salts.

In yet another embodiment, compounds are of the formula I where
R(1) is methyl, allyl, phenyl, or benzyl;
R(2) is hydrogen or methyl;
R(3) is phenyl which is substituted by R(7);
R(4) is hydrogen;
R(5) is butyl, preferably n-butyl, cyclohexyl, cyclohexylmethyl, phenyl, benzyl, 2-phenyl-ethyl, 1-naphthylmethyl, 2-naphthylmethyl, aminobenzyl, such as 4-aminobenzyl, benzyloxymethyl, carboxymethyl, or 2-carboxy-ethyl;
R(6) is NR(8)R(9);
R(7) is amidino or hydroxyamidino;
R(8) is hydrogen;
R(9) is

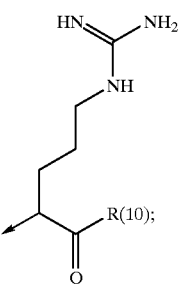

R(10) is NR(12)R(13) or OR(14);
R(12) is hydrogen or methyl;
R(13) is hydrogen or phenyl-(C$_1$–C$_2$)-alkyl;
R(14) is hydrogen, (C$_1$–C$_2$)-alkyl, or allyl;
in all their stereoisomeric forms and mixtures thereof in any ratio, and their physiologically acceptable salts.

Selected compounds of the formula I are:
2-(4-Carbamimidoyl-benzyl)-N-[(1-carbamoyl-4-guanidino-butylcarbamoyl)-cyclohexyl-methyl]-N',N'-dimethyl-malonamide trifluoroacetic acid salt, less polar diastereomer, 2-(S)-{2-(S)-[2-(Benzyl-methyl-carbamoyl)-3-(4-carbamimidoyl-phenyl)-propionylamino]-2-cyclohexyl-acetylamino}-5-guanidino-pentanoic acid allyl ester trifluoroacetic acid salt, less polar diastereomer, N-Benzyl-2-(4-carbamimidoyl-benzyl)-N'-[(S)-(1-(S)-carbamoyl-4-guanidino-butylcarbamoyl)-cyclohexyl-methyl]-malonamide trifluoroacetic acid salt, more polar diastereomer, N-Benzyl-2-(4-carbamimidoyl-benzyl)-N'-[(S)-(1-(S)-carbamoyl-4-guanidino-butylcarbamoyl)-cyclohexyl-methyl]-malonamide trifluoroacetic acid salt, less polar diastereomer, N-Benzyl-N'-[(S)-(1-(S)-carbamoyl-4-guanidino-butylcarbamoyl)-cyclohexyl-methyl]-2-[4-(N-hydroxycarbamimidoyl)-benzyl]-malonamide trifluoroacetic acid salt, N-[2-(4-Amino-phenyl)-1-(S)-(1-(S)-carbamoyl-4-guanidino-butylcarbamoyl)-ethyl]-2-(4-carbamimidoyl-benzyl)-N',N'-dimethyl-malonamide trifluoroacetic acid salt, 2-(4-Carbamimidoyl-benzyl)-N-[1-(S)-(1-(S)-carbamoyl-4-guanidino-butylcarbamoyl)-pentyl]-N'-methyl-malonamide trifluoroacetic acid salt, 4-(S)-[3-(4-Carbamimidoyl-phenyl)-2-dimethylcarbamoyl-propionylamino]-4-(1-(S)-carbamoyl-4-guanidino-butylcarbamoyl)-butyric acid, 2-(4-Carbamimidoyl-benzyl)-N-[1-(S)-(1-(S)-carbamoyl-4-guanidino-butylcarbamoyl)-2-naphthalen-2-yl-ethyl]-N',N'-dimethyl-malonamide trifluoroacetic acid salt, 2-(4-Carbamimidoyl-benzyl)-N-[1-(S)-(1-(S)-carbamoyl-4-guanidino-butylcarbamoyl)-3-phenyl-propyl]-N',N'-dimethyl-malonamide trifluoroacetic acid salt, 3-(S)-[3-(4-Carbamimidoyl-phenyl)-2-dimethylcarbamoyl-propionylamino]-N-(1-(S)-carbamoyl-4-guanidino-butyl)-succinamic acid trifluoroacetic acid salt, 2-(4-Carbamimidoyl-benzyl)-N-[(S)-(1-(S)-carbamoyl-4-guanidino-butylcarbamoyl)-phenyl-methyl]-N'-methyl-malonamide trifluoroacetic acid salt, 2-(4-Carbamimidoyl-benzyl)-N-[(S)-(1-(S)-carbamoyl-4-guanidino-butylcarbamoyl)-phenyl-methyl]-N',N'-dimethyl-malonamide trifluoroacetic acid salt, N-[2-Benzyloxy-1-(S)-(1-(S)-carbamoyl-4-guanidino-butylcarbamoyl)-ethyl]-2-(4-carbamimidoyl-benzyl)-N',N'-dimethyl-malonamide trifluoroacetic acid salt, 2-(4-Carbamimidoyl-benzyl)-N-[1-(S)-(1-(S)-carbamoyl-4-guanidino-butylcarbamoyl)-pentyl]-N',N'-dimethyl-malonamide trifluoroacetic acid salt, less polar diastereomer, 2-(S)-{2-(S)-[3-(4-Carbamimidoyl-phenyl)-2-dimethylcarbamoyl-propionylamino]-hexanoylamino}-5-guanidino-pentanoic acid trifluoroacetic acid salt, 2-(S)-{2-(S)-[3-(4-Carbamimidoyl-phenyl)-2-dimethylcarbamoyl-propionylamino]-2-cyclohexyl-acetylamino}-5-guanidino-pentanoic acid; compound with trifluoro-acetic acid trifluoroacetic acid salt, 2-(S)-{2-(S)-[3-(4-Carbamimidoyl-phenyl)-2-methylcarbamoyl-propionylamino]-2-cyclohexyl-acetylamino}-5-guanidino-pentanoic acid trifluoroacetic acid salt, 2-(S)-{2-(S)-[2-Benzylcarbamoyl-3-(4-carbamimidoyl-phenyl)-propionylamino]-2-cyclohexyl-acetylamino}-5-guanidino-pentanoic acid trifluoroacetic acid salt, 2-(S)-{2-(S)-[3-(4-Carbamimidoyl-phenyl)-2-dimethylcarbamoyl-propionylamino]-2-cyclohexyl-propionylamino}-5-guanidino-pentanoic acid trifluoroacetic acid salt, 2-(4-Carbamimidoyl-benzyl)-N-[1-(S)-(1-(S)-carbamoyl4-guanidino-butylcarbamoyl)-2-phenyl-ethyl]-N',N'-dimethyl-malonamide trifluoroacetic acid salt, less polar diastereomer, 2-(4-Carbamimidoyl-benzyl)-N-[1-(S)-(1-(S)-carbamoyl-4-guanidino-butylcarbamoyl)-2-naphthalen-1-yl-ethyl]-N',N'-dimethyl-malonamide trifluoroacetic acid salt, 2-(4-Carbamimidoyl-benzyl)-N-[1-(S)-(1-(S)-carbamoyl-4-guanidino-butylcarbamoyl)-pentyl]-N',N'-dimethyl-malonamide trifluoroacetic acid salt, 2-(4-Carbamimidoyl-benzyl)-N-[(S)-(1-(S)-carbamoyl-4-guanidino-butylcarbamoyl)-cyclohexyl-methyl]-N'-methyl-malonamide trifluoroacetic acid salt, 2-(4-Carbamimidoyl-benzyl)-N-[1-(S)-(1-(S)-carbamoyl-4-guanidino-butylcarbamoyl)-2-cyclohexyl-ethyl]-N',N'-dimethyl-malonamide trifluoroacetic acid salt, N-Benzyl-N'-[(S)-(1-(S)-carbamoyl-4-guanidino-butylcarbamoyl)-cyclohexyl-methyl]-2-[4-(N-hydroxycarbamimidoyl)-benzyl]-malonamide trifluoroacetic acid salt, less polar diastereomer, 2-(S)-{2-(S)-[3-(4-Carbamimidoyl-phenyl)-2-dimethylcarbamoyl-propionylamino]-2-cyclohexyl-acetylamino}-5-guanidino-pentanoic acid ethyl ester hydrochloric acid salt, 2-(S)-{2-(S)-[2-Benzylcarbamoyl-3-(4-carbamimidoyl-phenyl)-propionylamino]-2-cyclohexyl-acetylamino}-5-guanidino-pentanoic acid ethyl trifluoroacetic acid salt, less polar diastereomer, 2-(4-Carbamimidoyl-benzyl)-N-[(S)-cyclohexyl-(4-guanidino-1-(S)-phenethylcarbamoyl-butylcarbamoyl)-methyl]-N',N'-dimethyl-malonamide hydrochloric acid salt, N-Benzyl-2-(4-carbamimidoyl-benzyl)-N'-[(S)-(1-(S)-carbamoyl-4-guanidino-butylcarbamoyl)-cyclohexyl-methyl]-malonamide trifluoroacetic acid salt, more polar diastereomer, N-Benzyl-2-(4-carbamimidoyl-benzyl)-N'-[(S)-(1-(S)-carbamoyl-4-guanidino-butylcarbamoyl)-cyclohexyl-methyl]-malonamide trifluoroacetic acid salt, less polar diastereomer, N-Benzyl-2-(4-carbamimidoyl-benzyl)-N'-[(S)-(1-(S)-carbamoyl-4-guanidino-butylcarbamoyl)-cyclohexyl-methyl]-N-methyl-malonamide trifluoroacetic acid salt, 2-(S)-{2-(S)-[2-(Benzyl-methyl-carbamoyl)-3-(4-carbamimidoyl-phenyl)-propionylamino]-2-cyclohexyl-acetylamino}-5-guanidino-pentanoic acid hydrochloric acid salt, 2-(S)-{2-[2-(Benzyl-methyl-carbamoyl)-3-(4-carbamimidoyl-phenyl)-propionylamino]-2-cyclohexyl-acetylamino}-5-guanidino-pentanoic acid methyl ester trifluoroacetic acid salt, least polar diastereomer, N-Benzyl-N'-{[1-(S)-(benzyl-methyl-carbamoyl)4-guanidino-butylcarbamoyl]-cyclohexyl-methyl}-2-(4-carbamimidoyl-benzyl)-N-methyl-malonamide trifluoroacetic acid salt, less polar diastereomer, The invention also relates to compounds of formula I, wherein R(1) is hydrogen, $(C_1-C_6)$-alkyl, $(C_2-C_6)$-alkenyl, $(C_6-C_{10})$-aryl, $(C_6-C_{10})$-aryl-$(C_1-C_4)$-alkyl, where aryl in aryl-alkyl is unsubstituted or substituted by R(17);

R(2) is hydrogen or $(C_1-C_4)$-alkyl;

R(3) is $(C_6-C_{10})$-aryl which is substituted by R(7);

R(4) is hydrogen or $(C_1-C_4)$-alkyl;

R(5) is $(C_1-C_6)$-alkyl, $(C_3-C_7)$-cycloalkyl, $(C_3-C_7)$-cycloalkyl-$(C_1-C_4)$-alkyl, $(C_6-C_{10})$-aryl, $(C_6-C_{10})$-aryl-$(C_1-C_4)$-alkyl, where aryl in aryl-alkyl is unsubstituted or substituted by a residue R(20), and where alkyl is unsubstituted or substituted by a residue R(21); or R(4) and R(5) together form a residue of the formula II (II)

R(6) is NR(8)R(9) or OR(22);

R(7) is R(17) or R(20);

R(8) is hydrogen; $(C_1-C_4)$-alkyl, where alkyl is unsubstituted or substituted by a residue R(20); heteroaryl-$(C_1-C_4)$-alkyl; $(C_6-C_{10})$-aryl-$(C_1-C_4)$-alkyl, where aryl is unsubstituted or substituted by a residue R(17);

R(9) is

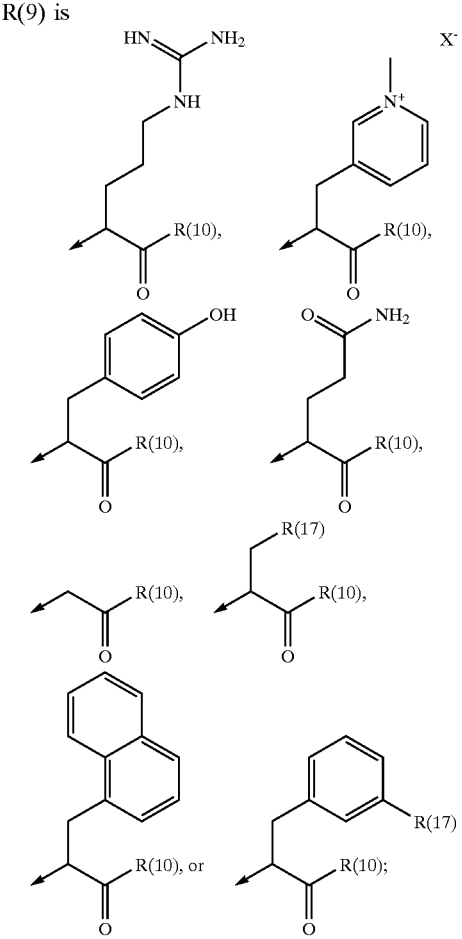

R(10) is

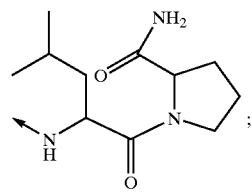

R(17) is —C(=N—R(18))-N(R(19))$_2$;
R(18) is hydrogen, hydroxy, or an amino protective group;
R(19) is hydrogen, $(C_1-C_4)$-alkyl, $(C_6-C_{10})$-aryl-$(C_1-C_4)$-alkoxycarbonyl, or an amino protective group;
R(20) is N(R(19))$_2$;
R(21) is hydroxy, $(C_6-C_{10})$-aryl-$(C_1-C_4)$-alkoxy, $(C_6-C_{10})$-aryl-$(C_1-C_4)$-alkoxycarbonylamino, carboxyl, or R(20);
R(22) is hydrogen or $(C_1-C_4)$-alkyl;
X$^-$ is a physiologically acceptable anion;
in all their stereoisomeric forms and mixtures thereof in any ratio, and their physiologically acceptable salts.

The invention also relates to compounds of formula I, wherein
R(1) is hydrogen, $(C_1-C_4)$-alkyl, allyl, phenyl, benzyl, or 4-carbamimidoyl-benzyl;
R(2) is hydrogen or $(C_1-C_4)$-alkyl;
R(3) is phenyl or 2-naphthyl which are substituted by R(7);
R(4) is hydrogen or methyl;
R(5) is n-butyl, sec-butyl, tert-butyl, cyclohexyl, cyclohexylmethyl, phenyl, benzyl, 2-phenyl-ethyl, 1-naphthylmethyl, 2-naphthylmethyl, aminobenzyl, such as 4-aminobenzyl, hydroxymethyl, benzyloxymethyl, carboxymethyl, 2-carboxy-ethyl, 3-amino-propyl, or 4-(benzyloxycarbonylamino)-butyl; or
R(4) and R(5) together form a residue of the formula II

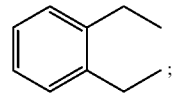

(II)

R(6) is NR(8)R(9), OH, or OCH$_3$;
R(7) is amidino, hydroxyamidino, amino, or dimethylamino;
R(8) is hydrogen, pyridylmethyl, such as 4-pyridylmethyl, 3-carbamimidoylbenzyl, or 4-aminobutyl;
R(9) is

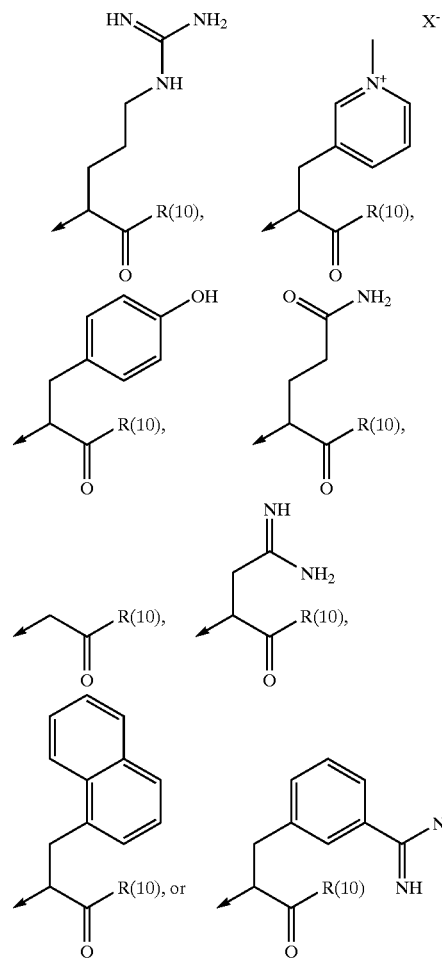

R(10) is

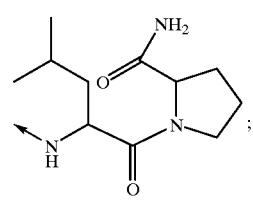

X⁻ is a physiologically acceptable anion;
in all their stereoisomeric forms and mixtures thereof in any ratio, and their physiologically acceptable salts.

The invention further relates to compounds of the formula I where
R(1) is propyl or butyl;
R(2) is propyl or butyl;
R(3) is phenyl which is substituted by R(7);
R(4) is hydrogen;
R(5) is cyclohexyl;
R(6) is NR(8)R(9);
R(7) is amidino, or amino;
R(8) is hydrogen;

R(9) is

R(10) is

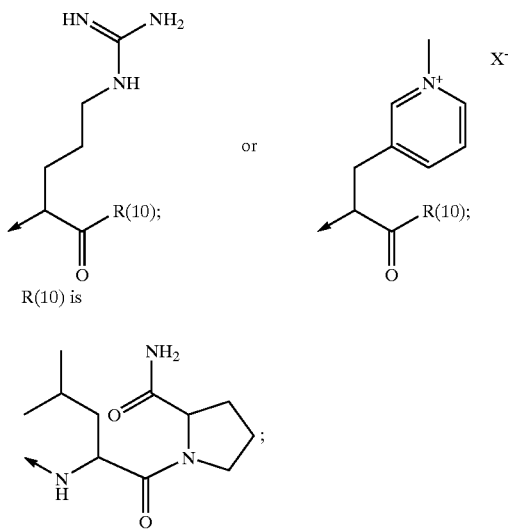

cyclohexyl-methyl)-N',N'-diisopropyl-malonamide trifluoroacetic acid salt, less polar diastereomer;

3-{2-(S)-{2-(S)-[3-(4-Carbamimidoyl-phenyl)-2-diisopropylcarbamoyl-propionylamino]-2-cyclohexyl-acetylamino}-2-[1-(S)-(2-(S)-carbamoyl-pyrrolidine-1-carbonyl)-3-methyl-butylcarbamoyl]-ethyl}-1-methyl-pyridinium trifluoro-acetate trifluoroacetic acid, less polar diastereomer, 2-(4-amino-benzyl)-N-((S)-{1-(S)-[1-(S)-(2-(S)-carbamoyl-pyrrolidine-1-carbonyl)-3-methyl-butylcarbamoyl]-4-guanidino-butylcarbamoyl}-cyclohexyl-methyl)-N',N'-diisopropyl-malonamide trifluoroacetic acid salt, less polar diastereomer, 2-(4-Carbamimidoyl-benzyl)-N-((S)-{1-(S)-[1-(S)-(2-(S)-carbamoyl-pyrrolidine-1-carbonyl)-3-methyl-butylcarbamoyl]-4-guanidino-butylcarbamoyl}-cyclohexyl-methyl)-N',N'-diisobutyl-malonamide trifluoroacetic acid salt, more polar diastereomer, The compounds of formula I can be prepared by utilizing procedures and techniques well known and appreciated by one of ordinary skill in the art. Starting materials or building blocks for use in the general synthetic procedures that can be applied in the preparation of the compounds of formula I are readily available to one of ordinary skill in the art. In many cases they are commercially available or have been described in the literature. Otherwise they can be prepared from readily available precursor compounds analogously to procedures described in this application.

The reactions described below that are carried out in the syntheses of the compounds of the formula I can generally be carried out according to the methods of conventional solution phase chemistry as well as according to the methods of solid phase chemistry which are well known, for example, from peptide synthesis.

Compounds of the formula I can be prepared, for example, by method A described in the schemes 2 and 3, where the residues R(1), R(2), R(3), R(4), R(5), R(6) are defined as indicated above.

Scheme 2

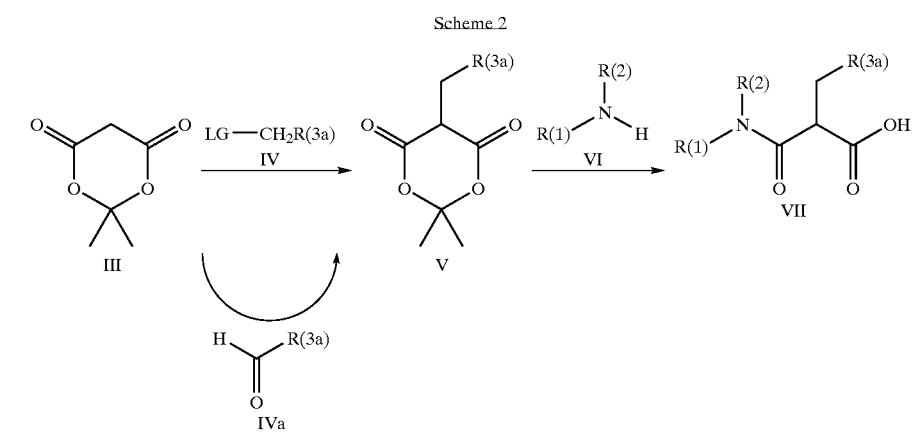

X⁻ is a physiologically acceptable anion;
in all their stereoisomeric forms and mixtures thereof in any ratio, and their physiologically acceptable salts.

Selected compounds of the formula 1 are:

2-(4-Carbamimidoyl-benzyl)-N-((S)-{1-(S)-[1-(S)-(2-(S)-carbamoyl-pyrrolidine-1-carbonyl)-3-methyl-butylcarbamoyl]-4-guanidino-butylcarbamoyl}-

Meldrum acid III can be alkylated by using base for example potassium carbonate, sodium hydrate, or triethylamine and IV, wherein
LG is a leaving group like a halogen or a substituted hydroxy group like tosyloxy or mesyloxy;
R(3a) is (C₆–C₁₀)-aryl which is substituted by R(23);
R(23) is N(R(24))₂, nitro, or cyano;

R(24) is $(C_1-C_6)$-alkyl, $(C_6-C_{10})$-aryl-$(C_1-C_4)$-alkyl, $(C_1-C_6)$-alkylcarbonyl, or $(C_1-C_6)$-alkoxycarbonyl;

to give V, or by condensation of meldrum acid III with the aldehyde IVa in presence of a reducing agent for example sodiumcyanoborohydride, while ring opening of V can be achieved by reaction of an amine VI, preferably in the presence of a silylating agent, for example N,O-bis-(trimethylsilyl)-acetamide in an organic solvent, for example in dichloromethane under reflux to give the malonic acid amide VII.

Compounds of the formulae III, IV, IVa, and VI are commercially available or can be prepared by standard procedures, which are known to one skilled in the art.

hydrogen sulfide to the cyano group, followed by alkylation, for example methylation, of the resulting thioamide and subsequent reaction with ammonia (GDR Patent No. 235 866), and the addition of hydroxylamine which may be obtained from a hydroxylammonium salt with a base, to the cyano group followed by conversion of the amidoxime to the amidine, for exam-pie by catalytic hydrogenation.

Saponification of the ester of compounds of the formula X to give compounds of the formula XI can be carried out by standard methods. Coupling of XI with XII to give compounds of the formula I can be carried out with coupling reagents as described above. Compounds of the formula XII are commercially available or can be prepared by standard procedures which are known to one skilled in the art.

Scheme 3

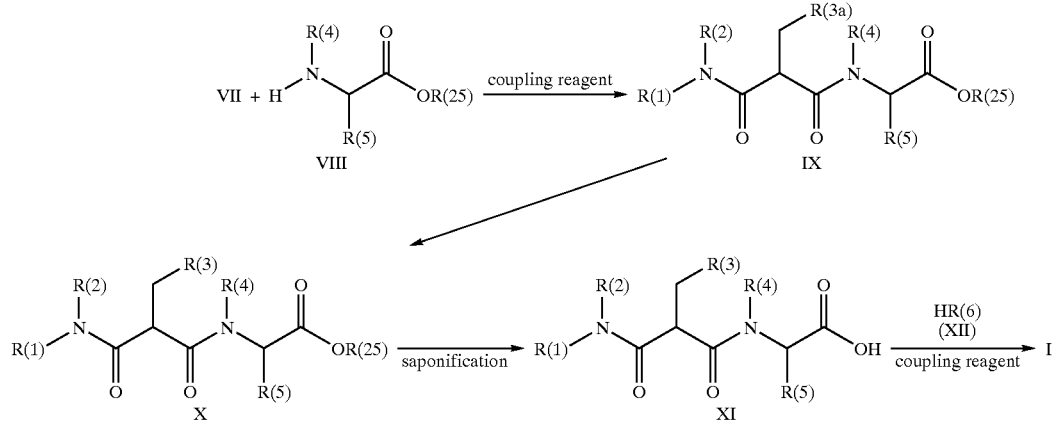

Coupling of VII with VIII, where R(25) is an easily cleavable ester (such as for example $(C_1-C_4)$-alkyl, benzyl, or 4-methoxybenzyl), to yield IX can be carried out by common coupling reagents used in peptide synthesis. Such coupling reagents are, for example, carbodiimides like dicyclohexylcarbodiimide (DCCI) or diisopropyl-carbodiimide (DICI), carbonyldiazoles like carbonyldiimidazole and similar reagents, propylphosphonic anhydride, O-((cyano-(ethoxycarbonyl)-methylen)amino)-N,N,N',N'-tetramethyluronium tetrafluoroborate (TOTU), N-[(dimethylamino)-1H-1,2,3-triazolo[4,5-b]pyridin-1yl-methylene]-N-methylmethanaminium hexafluorophosphate N-oxide (HATU), and many others. Compounds of the formula VIII are commercially available or can be prepared by standard procedures, which are known to one skilled in the art.

Conversion of R(3a) to R(3) (IX→X), if necessary, can be made by introduction of an amidino group as described below, or by reduction of a nitro group by hydrogenation with for example Raney-Nickel, palladium/charcoal or other catalysts in the presence of hydrogen.

Amidines can be prepared from the corresponding cyano compounds by addition of alcohols, for example methanol or ethanol, in acidic anhydrous medium, for example dioxane, methanol or ethanol, and subsequent aminolysis, for example treatment with ammonia in alcohols such as, for example, isopropanol, methanol or ethanol (G. Wagner, P. Richter and Ch. Garbe, Pharmazie 29 (1974), 12–55). Further methods of preparing amidines are the addition of Compounds of the formula I can also be obtained by method B as drawn in schemes 4 and 5.

Scheme 4

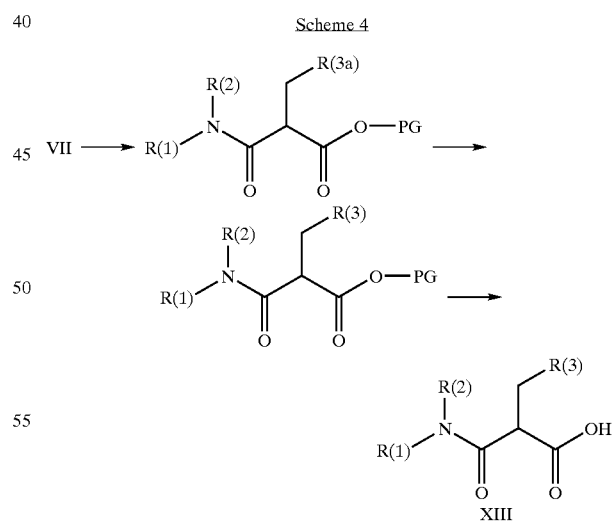

After protection of the carboxylfunction with an easily cleavable protection group PG (such as for example $(C_1-C_4)$-alkyl, benzyl, or 4-methoxybenzyl) by standard methods, the residue R(3a) in compounds of the formula VII can be transformed to the residue R(3) and deprotected as outlined above to give compounds of the formula XIII.

Scheme 5

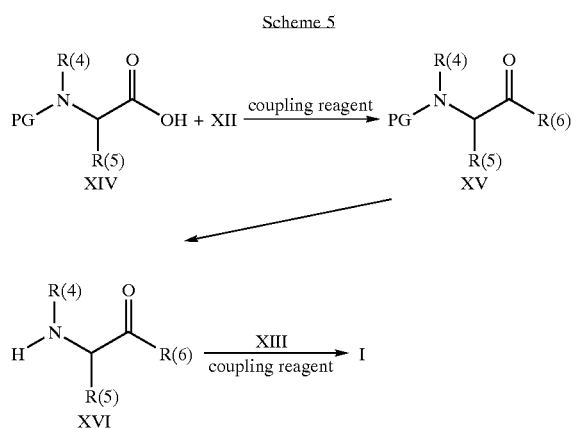

The protected amino acid XIV, wherein PG is a suitable amino protection group, for example Fmoc, benzyloxycarbonyl (Z), or Boc, can be coupled by standard methods as described above with compounds of the formula XII to give compounds of the formula XV. Compounds of the formula XIV can be prepared by standard procedures, which are known to one skilled in the art.

Compounds of the formula XV can be deprotected by standard methods, for example by standard methods for Fmoc-deprotection (L. A. Carpino et al., J. Org. Chem. 1988, 53, 6139–44) to give compounds of the formula XVI. Compounds of the formula XVI can be coupled with compounds of the formula XII by standard methods to give compounds of the formula I.

Compounds of the formula I can also be obtained by solid phase peptide synthesis (method C) as drawn in scheme 6. Such methods are described, for example, by Steward and Young (Solid Phase Peptide Synthesis (Freeman and Co., San Francisco, 1969), which is incorporated herein by reference. Where solid phase synthesis methods are employed, the chemical composition of a compound can be manipulated while the nascent peptide is attached to the resin or after the peptide has been cleaved from the resin to obtain, for example, an N-terminal derivative. Similar modifications can also be made to a carboxy group of a compound, including a C-terminus carboxy group, which, for example, can be amidated. One skilled in the art can also synthesize a compound of the invention using solution phase organic chemistry.

Scheme 6

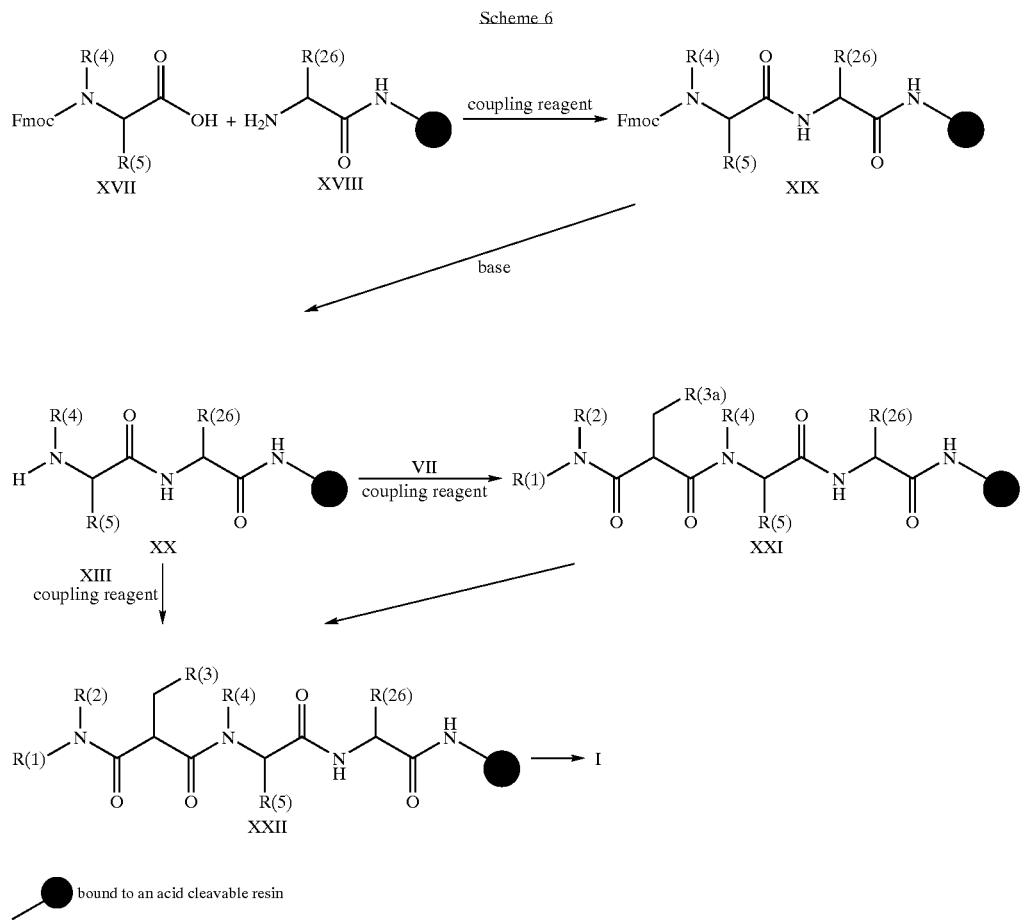

Using this method (C) (scheme 6) compounds of the formula XVIII, where an amino acid is coupled to a suitable carrier, which are for instance Wang, Trityl or Rink resin or other acid cleavable resins which are known to a person skilled in the art, and wherein R(26) is hydrogen, —CH$_2$—R(17), 1-naphthylmethyl, —(CH$_2$)$_3$—NR(28)-C(=N—R(27))-NH—R(28)

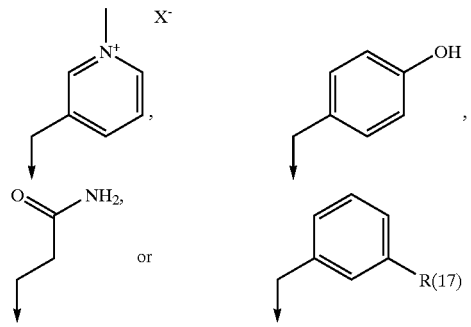

R(27) is R(28), cyano, hydroxy, (C$_1$–C$_6$)-alkoxy, (C$_6$–C$_{14}$)-aryl-(C$_1$–C$_6$)-alkoxy which is unsubstituted or substituted in the aryl moiety, or amino;

R(28) is hydrogen, (C$_1$–C$_6$)-alkyl, or (C$_1$–C$_6$)-alkylcarbonyl;

can be coupled with, for example, an Fmoc-protected amino acid XVII using standard techniques. The use of other protected, for instance Boc-protected, amino acid XVII is also possible.

Compounds of the formula XVIII can be prepared by standard procedures, which are known to one skilled in the art.

The resulting dipeptide XIX can be deprotected using base, for example a solution of 20–50% of piperidin in dimethylformamide, to obtain compounds of the formula XX with a primary or secondary amino group, which can be coupled to the building blocks VII or XIII prepared using methods A and B to yield compounds of the formula XXI or XXII. Conversion of the residue R(3a) of the resulting compound XXI to the residue R(3) can be done as described above to yield compounds of the formula XXII. Compounds of the formula I can be obtained by cleaving compounds of the formula XXII under acidic conditions for example trifluoroacetic acid/water in different concentrations depending on the used resin varying from 1% to 95% of trifluoroacetic acid.

These synthesized compounds can be purified using well known methods such as reverse phase-high pressure liquid chromatography (RP-HPLC) or other methods of separation based, for example, on the size, charge or hydrophobicity of the compound. Similarly, well known methods such as amino acid sequence analysis or mass spectrometry (MS or HPLC/ESMS) can be used for characterizing the structure of a compound of the invention (see Example 1).

Thus, the present invention also relates to a process for the preparation of a compound of formula I, which comprises i)
a1) alkylating a compound of the formula III

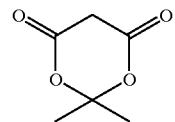

III with a compound of the formula IV,

LG—CH$_2$—R(3a)  (IV)

wherein LG is a leaving group like a halogen or a substituted hydroxy group like tosyloxy or mesyloxy and wherein R(3a) is (C$_6$–C$_{10}$)-aryl which is substituted by R(23);
R(23) is N(R(24))$_2$, nitro, or cyano;
R(24) is (C$_1$–C$_6$)-alkyl, (C$_6$–C$_{10}$)-aryl-(C$_1$–C$_4$)-alkyl, (C$_1$–C$_6$)-alkylcarbonyl, or (C$_1$–C$_6$)-alkoxycarbonyl;

in the presence of a base to give a compound of the formula V,

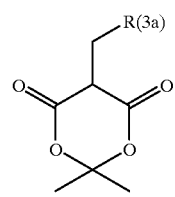

V or reacting a compound of the formula III with a compound of the formula IVa,

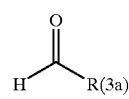

IVa in the presence of a reducing agent to give a compound of the formula V;

b1) reacting a compound of the formula V with a compound of the formula VI,

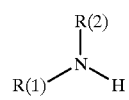

VI wherein R(1) and R(2) are as defined above, to give a compound of the formula VII;

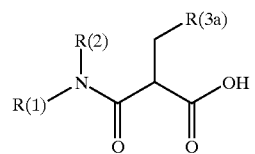

VII c1) coupling of a compound of the formula VII with a compound of the formula VIII,

VIII

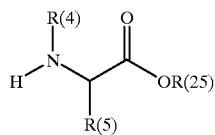

wherein R(4) and R(5) are as defined above and R(25) is an easily cleavable ester to yield a compound of the formula IX,

IX

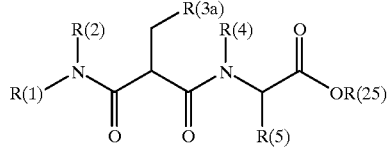

d1) optionally introducing an amidino group or reduction of a nitro group, by converting a compound of the formula IX into a compound of the formula X,

X

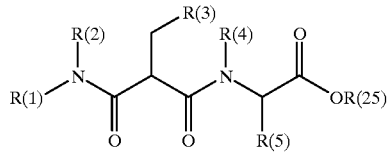

wherein R(3) is as defined above;

e1) saponification of the ester group R(25) and coupling the resulting compound XI according to step c 1) with a compound of the formula XII

HR(6)          (XII)

wherein R(6) is as defined above to give a compund of the formula I; or c2) protecting the carboxylfunction in a compound of the formula VII with an easily cleavable protescting group and introducing an amidino group or reduction of a nitro group according to step d1) to give after deprotection of the carboxylfunction a compound of the formula XIII; and d2) coupling a compound of the formula XIII according to step c1)

XIII

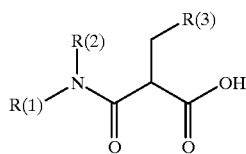

with a compound of formula XVI;

XVI

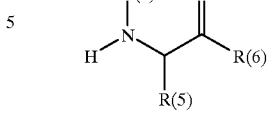

to give a compound of the formula I; or ii)
a) coupling a compound of the formuola XVIII,

XVIII

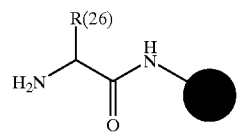

which is bound to a suitable carrier (represented by the shaded circle above), for example an acid cleavable resin, and wherein R(26) is hydrogen, —CH$_2$-R(17), 1-naphthylmethyl, —(CH$_2$)$_3$—NR(28)—C(=N-R(27))—NH—R(28)

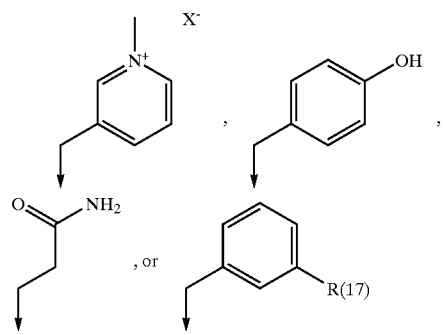

R(27) is R(28), cyano, hydroxy, (C$_1$–C$_6$)-alkoxy, (C$_6$–C$_{14}$)-aryl-(C$_1$–C$_6$)-alkoxy which is unsubstituted or substituted in the aryl moiety, or amino;

R(28) is hydrogen, (C$_1$–C$_6$)-alkyl, or (C$_1$–C$_6$)-alkylcarbonyl; and R(17) is as defined above;

with a compound of the formula XVII

XVII

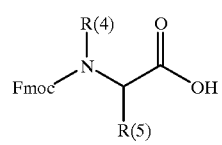

wherein R(4) and R(5) are as defined above to give a compound of the formula XIX

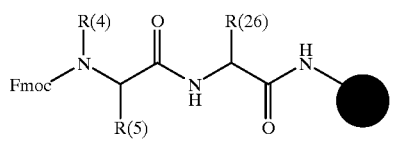

XIX b) and after deprotecting a compound of the formula XIX with a base coupling the deprotected compound XX to a compound of the formula VII or XIII to give a compound of the formula XXI or XXII;

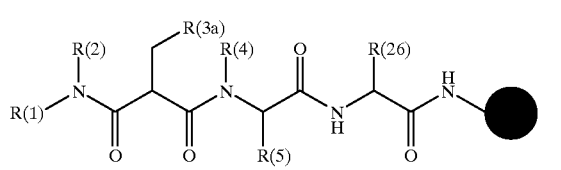

XXI

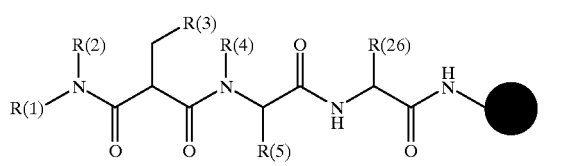

XXII c) optionally converting a compound of the formula XXI to a compound of formula XXII (i.e. transforming the residue R(3a) to a residue R(3) by introducing an amidino group or reduction of a nitro group), and d) cleaving a compound of the formula XXII off the resin to give a compound of the formula I. As is demonstrated in the pharmacological tests described below, the compounds of formula I inhibit factor Xa activity. They can therefore be used as pharmaceuticals when, for example, it is desired to reduce factor Xa activity or to produce effects that can be achieved by inhibiting factor Xa activity in a system, such as influencing coagulation or inhibiting blood clotting. Thus, the present invention also relates to the compounds of formula I for use as pharmaceuticals as well as for the production of medicaments, such as medicaments for treatment or prophylaxis of the conditions and diseases mentioned below and above. Further, the present invention provides a method of specifically inhibiting factor Xa activity by contacting factor Xa with a compound of formula I. More specifically, an effective amount of a compound of the invention inhibits factor Xa catalytic activity either directly, within the prothrombinase complex or as a soluble subunit, or indirectly, by inhibiting the assembly of factor Xa into the prothrombinase complex. One embodiment of the invention comprises such compounds of the formula I which can inhibit factor Xa activity with a $K_i \leq 10$ μM, as well as compounds of the formula I which can inhibit factor Xa activity with a $K_i \leq 100$ μM.

As used herein, the term "factor Xa activity" refers to the ability of factor Xa, by itself or in the assembly of subunits known as the prothrombinase complex, to catalyze the conversion of prothrombin to thrombin. When used in reference to factor Xa activity, the term "inhibition" includes both the direct and indirect inhibition of factor Xa activity. Direct inhibition of factor Xa activity can be accomplished, for example, by the binding of a compound of formula I to factor Xa or to prothrombinase so as to prevent the binding of prothrombin to the prothrombinase complex active site. Indirect inhibition of factor Xa activity can be accomplished, for example, by the binding of a compound of the invention to soluble factor Xa so as to prevent its assembly into the prothrombinase complex. As used herein, the term "specific" when used in reference to the inhibition of factor Xa activity means that a compound of formula I can inhibit factor Xa activity without substantially inhibiting the activity of serine proteases, such as thrombin, trypsin or kallekrein (using the same concentration of the inhibitor). Such proteases are involved in the blood coagulation and fibrinolysis cascade.

Inhibition of factor Xa activity or the production of effects achieved by such an inhibition can take place in vivo, i.e. in an individual. As used herein, the term "individual" means a vertebrate, including a mammal such as, for example a mouse, a rat, a rabbit, a dog, a pig, a monkey, and a human, in which factor Xa is involved in the clotting cascade. It can also take place outside the body of an individual, for example, in an extracorporeal circulation or in the treatment of blood samples from an individual, and generally in vitro. In vitro uses of the compounds of formula I are, for example, the use as a biochemical tool in scientific or analytical investigations or the use for in vitro diagnoses. A compound of formula I can be used as an anticoagulant, which can be contacted with a blood sample to prevent coagulation. For example, an effective amount of a compound of formula I can be contacted with a freshly drawn blood sample to prevent coagulation of the blood sample.

As used herein, the term "effective amount" when used in this connection means an amount of a compound of formula I that inhibits factor Xa activity to the desired extent. The skilled artisan would recognize that an effective amount of a compound of the invention can be determined using the methods disclosed herein or otherwise known in the art.

In view of the disclosed utility of the compounds of formula I, the skilled artisan also would recognize that an agent such as heparin can be replaced with a compound of the invention. Such a use of a compound of formula I can result, for example, in a cost saving as compared to other anticoagulants.

In a further embodiment, the present invention provides a method of inhibiting factor Xa in a patient in need thereof, comprising administering to said patient an effective factor Xa inhibitory amount of a compound of formula I. As used herein, the term "patient" refers to a warm-blooded animal including a mammal and a human. A patient is in need of treatment to inhibit factor Xa when the patient is suffering from a disease state that can be beneficially influenced by inhibiting factor Xa activity or that is expected by the clinician to be beneficially influenced by inhibiting factor Xa activity.

The identification of those patients who are in need of treatment to inhibit factor Xa is well within the ability and knowledge of one skilled in the art. A clinician skilled in the art can readily identify, by the use of clinical tests, physical examination and medical/family history, those patients who are in need of such a treatment.

Since a compound of formula I can inhibit factor Xa activity, such a compound can be used for reducing or inhibiting blood clotting in an individual. Thus, the present invention further provides a method of reducing or inhibiting the formation of blood clots in an individual, such as in a patient in need thereof, by administering a therapeutically effective amount of a compound of formula I.

A therapeutically effective amount relating to the production in an individual of an effect like inhibition or reduction of blood clotting, or an effective factor Xa inhibitory amount of a compound of formula I means the amount or the dose of a compound of formula I that has to be administered to an individual in order to achieve or to maintain the desired effect or to inhibit factor Xa activity in the individual to the desired extent. Such an effective amount or dose to be administered has to be adjusted to the individual circumstances in each case. It can be readily determined by the use of conventional techniques using the methods described herein or otherwise known in the art, and by observing results obtained under analogous circumstances. In determining the effective dose, a number of factors are considered including, but not limited to: the species of patient; its size, age, and general health; the specific disease involved; the degree or the involvement or the severity of the disease; the response of the individual patient; the particular compound administered; the mode of administration; the bioavailability characteristics of the pharmaceutical preparation administered; the dose regimen selected; and the use of concomitant medication. An appropriate dosage can be established using clinical approaches well known in the medical art.

In general, in view of the above factors it is evident that the effective factor Xa inhibitory amount or the therapeutically effective amount of a compound of formula I will vary and can be varied within wide limits. Usually, an effective amount will vary from about 0.01 milligram per kilogram of body weight per day (mg/kg per day) to about 20 mg/kg per day. A daily dose of from about 0.1 mg/kg to about 10 mg/kg is generally preferred. These data refer to a human of about 75 kg of body weight. In particular when administering relatively large quantities, it can be favorable to subdivide the daily dose into several, for example 2, 3 or 4 subdose administrations.

A compound of formula I can be administered to an individual for the treatment of a variety of clinical conditions, including, for example, the treatment and prophylaxis of cardiovascular disorders or complications associated, for example, with infection or surgery. Examples of cardiovascular disorders include restenosis, for example restenosis following angioplasty, reocclusion prophylaxis, conditions after coronary bypass operations, arterial, venous and microcirculatory disease states, cardiac infarction, angina pectoris, thromboembolic diseases, thromboses, embolism, adult respiratory distress syndrome, multi-organ failure, stroke or disseminated intravascular coagulation clotting disorder. Examples of related complications associated with surgery include, for example, deep vein and proximal vein thrombosis, which can occur following surgery. Thus, a compound of the invention is useful as a medicament for reducing or inhibiting unwanted coagulation or blood clotting in an individual.

The compounds of formula I, their physiologically acceptable salts and other suitable derivatives thereof can be employed as medicaments or pharmaceuticals in the above-mentioned methods on their own, in mixtures with each other or in the form of pharmaceutical compositions which comprise, as the active ingredient, an effective amount of at least one compound of formula I and/or of a physiologically acceptable salt and/or another suitable derivative thereof in admixture or otherwise in association with one or more pharmaceutically acceptable carrier substances and auxiliary substances.

In effecting treatment of a patient, compounds of formula I on their own or pharmaceutical compositions comprising them can be administered in any form or mode which makes the compounds of formula I bioavailable in effective amounts, including oral and parenteral routes. For example, they can be administered orally, for example in the form of pills, tablets, lacquered tablets, coated tablets, granules, hard and soft gelatin capsules, solutions, syrups, emulsions, suspensions or aerosol mixtures; rectally, for example in the form of suppositories; parenterally, for example intravenously, intramuscularly, transdermally, intranasally, or subcutaneously; in the form of injection solutions or infusion solutions, microcapsules, implants or rods; percutaneously or topically, for example in the form of ointments, solutions or tinctures, or in other ways, for example in the form of aerosols or nasal sprays. Oral administration is generally preferred but depending on the specific case other modes of administration can also be favourable, for example in an acute stage of a disease intravenous administration by means of injection or infusion. One skilled in the art of preparing formulations can readily select the proper form and mode of administration depending upon the disease state to be treated, the stage of the disease, and other relevant circumstances.

Pharmaceutical compositions or medicaments comprising a compound of formula I and/or a physiologically acceptable salt and/or another suitable derivative thereof can be made by combining the compounds of formula I and/or their physiologically acceptable salts and/or other suitable derivatives thereof with pharmaceutically acceptable carrier substances and auxiliary substances, the proportion and nature of which are determined by the chosen route of administration and standard pharmaceutical practice. The pharmaceutical compositions or medicaments are prepared in a manner well known in the pharmaceutical art. The pharmaceutical compositions will, in general, contain an effective amount of a compound of formula I and/or a physiologically acceptable salt and/or another suitable derivative thereof together with a suitable amount of a carrier so as to comprise the proper dosage for administration to an individual. The pharmaceutical compositions may be adapted for oral or parenteral use and may be administered to the patient in the form, for example, of tablets, capsules, suppositories, solutions, suspensions, ointments, tinctures, nasal sprays, aerosol mixtures, implants, rods, microcapsules or the like. Thus, together with the claimed compounds the present invention provides useful pharmaceutical compositions or medicaments for inhibiting factor Xa activity and blood clotting in an individual.

The present invention further encompasses a process for the preparation of pharmaceutical compositions or medicaments which comprise at least one compound of formula I and/or a physiologically acceptable salt and/or another suitable derivative thereof, as well as it encompasses the use of the compounds of formula I and/or physiologically acceptable salts and/or other suitable derivatives thereof for the preparation of medicaments, for example, medicaments for the treatment or prophylaxis of the above-mentioned diseases.

Pharmaceutically acceptable carrier and auxiliary substances are referred to as substances or compositions that are non-toxic to an individual or have acceptable toxicity as determined by the appropriate regulatory agency. The carrier substance or excipient may be a solid, semi-solid, or liquid material which can serve as a vehicle or medium for the active ingredient. As used herein, the term "pharmaceutically acceptable carrier" encompasses any of the standard pharmaceutical carriers such as liquid carriers, for example phosphate buffered saline, water, an emulsion such as an oil/water or water/oil emulsion, or solid or semi-solid carriers such as, for example, lactose, cornstarch, fats, waxes, etc. Suitable pharmaceutical carriers and their formulations are well known in the art and are, for example, described by Martin in Remington's Pharmaceutical Sciences, 15th Ed. (Mack Publishing Co., Easton 1975) which is incorporated herein by reference also with respect to other aspects of the ingredients and the preparation of pharmaceutical compositions.

Examples of auxiliary substances are fillers, disintegrants, binders, glidants, wetting agents, stabilizers, emulsifiers, preservatives, sweeteners, dyes, flavorants, aromatizing agents, thickeners, diluents, buffering substances, solubilizing agents, agents for achieving a slow-release effect, salts for altering the osmotic pressure, coating agents, antioxidants, etc.

For the purpose of oral administration, the compounds of formula I may be incorporated with excipients or inert diluents or edible carriers and used in the form of, for example, tablets, film tablets, coated tablets, pills, troches, capsules, granules, solutions, suspensions, emulsions, elixirs, syrups, wafers, chewing gums and the like, or they may be enclosed in gelatin capsule. The pharmaceutical compositions for oral administration may be varied depending upon the particular form. Usually they contain at least 1% of the active ingredient of formula I and may conveniently contain up to about 90% of the weight of the unit. Generally, the content of the compounds of formula I and/or their physiologically acceptable salts and/or other suitable derivatives is from about 4% to about 70% by weight. The amount of the active ingredient present in the compositions is such that a unit dosage form suitable for administration will be obtained.

The tablets, pills, capsules, troches and the like may also contain, for example, one or more of the following carrier and auxiliary substances: binders, such as microcrystalline cellulose, gum tragacanth or gelatin; excipients, such as starch or lactose, disintegrating agents such as alginic acid, PRIMOGEL®, cornstarch and the like; lubricants, such as magnesium stearate or STEROTEX®; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, for example sucrose as a sweetening agent and certain preservatives, dyes and colorings and flavors.

For the purpose of parenteral administration, the compounds of formula I and/or physiologically acceptable salts thereof and/or other suitable derivatives thereof may be incorporated into a solution or a suspension. The solutions or suspensions may, for example, also include one or more of the following carrier and auxiliary substances: sterile diluents such as water for injection, saline solution, fixed oils, polyethylene glycols, glycerine, propylene glycol or other synthetic solvents;

antibacterial agents such as benzyl alcohol or methyl paraben; antioxidants such as ascorbic acid or sodium bisulfite; chelating agents such as ethylene diaminotetraacetic acid; buffers such as acetates, citrates or phosphates; agents for the adjustment of toxicity such as sodium chloride or dextrose. The content of the compounds of formula I in the preparations for parenteral adminstration may be varied. Usually they contain at least 0.1% by weight of the compound of formula I. Generally, the content of the compound of formula I and/or the physiologically acceptable salts thereof and/or other suitable derivatives thereof is from about 0.1% to 50%. The parenteral preparations can be enclosed in ampules, disposable syringes, multiple dose vials made of glass or plastic, or infusion bottles. Suitable excipients for microcapsules, implants and rods are, for example, mixed polymers of glycolic acid and lactic acid.

Materials used in preparing the various pharmaceutical compositions should be pharmaceutically pure and non-toxic in the amounts used.

Besides one or more compounds of formula I and/or one or more physiologically acceptable salts thereof and/or one or more other suitable derivatives thereof as active compounds the pharmaceutical compositions according to present invention may also contain one or more other pharmacologically active compounds.

In another, more general embodiment of the present invention, compositions are provided comprising at least one compound of formula I and/or salt thereof and/or another suitable derivative thereof in admixture or otherwise in association with one or more inert carriers. These compositions are useful, for example, as assay standards, as convenient means of making bulk shipments, or as pharmaceutical compositions. An assayable amount of a compound of formula I is an amount which is readily measurable by standard assay procedures and techniques as are well known and appreciated by those skilled in the art. An assayable amount of a compound of formula I will generally vary from about 0.001% to about 90% of the composition by weight. Inert carriers can be any material which does not degrade or otherwise covalently react with a compound of formula I. Examples of suitable inert carriers are water; aqueous buffers, such as, for example, those which are generally useful in High Pressure Liquid Chromatography (HPLC) analysis; organic solvents, such as acetonitrile, ethyl acetate, hexane and the like; and pharmaceutically acceptable carriers and auxiliary substances.

The compounds of formula I can also be used as starting materials or chemical intermediates in the preparation of other compounds, including the preparation of other pharmacologically active compounds. Examples for such conversions of compounds of the invention into other compounds of the invention are given below. For this use, besides the compounds of formula I and their physiologically acceptable salts also other salts of the compounds of the formula I can be useful which are not suitable or less suitable for use as pharmaceuticals. Thus, the present invention also relates to compounds of the formula I and their salts in general as chemical intermediates, especially as intermediates in the preparation of pharmacologically active compounds.

The following tests can serve to investigate the pharmacological activity and to illustrate the utility of the compounds of the present invention as factor Xa inhibitors.

Test 1: In Vitro Inhibition of Selected Purified Coagulation Enzymes and other Serine Proteases The ability of a compound of formula I to inhibit factor Xa, thrombin, plasmin, elastase and trypsin may be assessed by determining the concentration of compound of formula I that inhibits enzyme activity by 50% ($IC_{50}$). Purified enzymes are used in chromogenic assays. To determine the inhibition constant, the $IC_{50}$ value is corrected for competition with substrate using the formula:

$K_i = IC_{50} \times (1/\{1+((\text{substrate concentration})/\text{substrate Km})\})$ where Km is the Michaelis-Menten-constant (Y.-C. Chen and W. H. Prusoff, Biochem. Pharmacol. 22: 3099–3018 (1973), which is incorporated herein by reference).

a. Factor Xa Assay

TBS-PEG buffer (50 mM Tris-Cl, pH 7.8, 200 mM NaCl, 0.05% (w/v) PEG-8000, 0.02% (w/v) NaN$_3$) is used for this assay. The IC$_{50}$ is determined by combining in appropriate wells of a Costar half-area microtiter plate 25 µl human factor Xa (Enzyme Research Laboratories, Inc.; South Bend, Ind.) in TBS-PEG; 40 µl 10% (v/v) DMSO in TBS-PEG (uninhibited control) or various concentrations of the compound to be tested diluted in 10% (v/v) DMSO in TBS-PEG; and substrate S-2765 (N-benzyloxycarbonyl-D-Arg-Gly-L-Arg-p-nitroanilide; Kabi Pharmacia, Inc.; Franklin Ohio) in TBS-PEG.

The assays are performed by pre-incubating the compound of formula I plus enzyme for 10 min, then the assay is initiated by adding substrate to obtain a final volume of 100 µl. The initial velocity of chromogenic substrate hydrolysis is measured by the change in absorbance at 405 nm using a Bio-tek Instruments kinetic plate reader (Ceres UV900HDi) at 25° C. during the linear portion of the time course (usually 1.5 min after addition of substrate). The concentration of inhibitor that causes a 50% decrease in the rate of substrate hydrolysis is predicted by linear regression after plotting the relative rates of hydrolysis (compared to the uninhibited control) versus the log of the compound of formula I concentration. The enzyme concentration is 0.5 nM and substrate concentration is 140 µM.

b. Thrombin Assay

TBS-PEG buffer is used for this assay. The IC$_{50}$ is determined as above for the Factor Xa assay, except that the substrate is S-2366 (L-PyroGlu-L-Pro-L-Arg-p-nitroanilide; Kabi) and the enzyme is human thrombin (Enzyme Research Laboratories, Inc.; South Bend Ind.). The enzyme concentration is 175 µM.

c. Plasmin Assay

TBS-PEG buffer is used for this assay. The IC$_{50}$ is determined as described above for the factor Xa assay, except that the substrate is S-2251 ((D)-Val-L-Leu-L-Lys-p-nitroanilide; Kabi) and the enzyme is human plasmin (Kabi). The enzyme concentration is 5 nM and the substrate concentration is 300 µM.

d. Trypsin Assay

TBS-PEG buffer containing 10 mM CaCl$_2$ is used for this assay. The IC$_{50}$ is determined as described above in the factor Xa assay, except that the substrate is BAPNA (Benzoyl-L-Arg-p-nitroanilide; Sigma Chemical Co.; St. Louis Mo.) and the enzyme is bovine pancreatic trypsin (Type XIII, TPCK treated; Sigma). The enzyme concentration is 50 nM and the substrate concentration is 300 µM.

e. Elastase Assay

Tris-Cl, pH 7.4, 300 mM NaCl, 2% (v/v) N-methyl-pyrrolidone, 0.01% (w/v) NaN$_3$ buffer is used for this assay. The IC$_{50}$ is determined as described above in the factor Xa assay, except that the substrate is succinyl-Ala-Ala-Ala-p-nitroanilide (Calbiochem-Nova Biochem Corp.; San Diego Calif.) and the enzyme is human neutrophil elastase (Athens Research and Technology, Inc.; Athens Ga.). The enzyme concentration is 75 nM and the substrate concentration is 600 µM. The control compound is TENSTOP® (N-alpha-tosyl-Gly-p-amidinophenylalanine methyl ester; American Diagnostica, Inc.; Greenwish Conn.), which is a reversible factor Xa inhibitor (Stuerzebecher et al., Thromb. Res. 54: 245–252 (1989); Hauptmann et al., Thromb. Haem. 63: 220–223 (1990), each of which is incorporated herein by reference).

Test 2: Assays for Determining Inhibition of Coagulation

The effectiveness of compounds of formula I may be assessed by the in vitro prothrombin time (PT) assay using pooled human donor plasma. An ex vivo assay may also be used in which plasma is collected at various times after intravenous (iv) administration of a compound of formula I to rats or to rabbits or intraduodenal (id) administration to rats and analysis using the PT assay to determine plasma half-life. The PT assay is initiated with a thromboplastin dilution selected to obtain an extended and highly reproducible coagulation endpoint, referred to as the "dilute PT assay" as described below. The effectiveness of various compounds may also be determined using an in vivo rat arteriovenous shunt model of thrombosis.

a. In Vitro Dilute Prothrombin Time Assay

100 µl prewarmed (37° C.) pooled human platelet poor plasma (PPP) is added to a fibrometer cup (Baxter Diagnostics., Inc.; McGaw Park Ill.). 50 µl of various concentrations of a compound of formula I in TBS-BSA with calcium (50 mM Tris-Cl, 100 mM NaCl, 0.1% (w/v) bovine serum albumin, 20 mM CaCl$_2$) is added. In control experiments, TBS-BSA with calcium but without test compound of formula I is added for measurement of uninhibited coagulation time. 150 µl diluted prewarmed rabbit thromboplastin (Baxter) with calcium is added to the fibrometer cup and the fibrometer timer is started. A rabbit thromboplastin dilution curve is obtained prior to treating the compound and is used to choose a thromboplastin dilution that allows approximately 30 sec PT time for uninhibited controls. The experimental concentration giving 50% inhibition of coagulation (EC$_{50}$) with test compound is calculated from the dilution curve times.

Alternatively, the dilute prothrombin time assay is conducted using the "research" mode on an Instrumentation Laboratories (Ill.) ACL3000-plus automated coagulation instrument (IL; Milan, Italy). Thromboplastin is diluted until a clotting time of 30–35 sec. is achieved. This clotting time is taken as 100% activity. A standard curve for calibration is established by serial 2-fold dilution of the diluted thromboplastin reagent (rabbit brain IL-brand thromboplastin). During the assay, a 50 µl sample (plasma separated by centrifugation) is mixed with 100 µl thromboplastin reagent and nephelometric readings are taken over 169 sec. Coagulation time is determined from the maximal rate of change of light scatter calculated by the instrument. Inhibition is expressed as percent activity as determined by comparison with the calibration curve.

b. Ex Vivo Dilute Prothrombin Time Assay

A test compound of formula I is administered intravenously either through the tail vein (rat) or ear vein (rabbit) following an approved protocol. 0.5 ml blood samples are removed at timed intervals after administration of a test compound of formula I from a cannulated carotid artery (rat) or auricular artery (rabbit). After centrifugation to obtain PPP, the plasma is immediately stored on ice or frozen.

For dilute prothrombin time determination, the plasma is prewarmed and assayed as described above. Percent inhibition is calculated from a thromboplastin dilution curve, which is run with each series of samples, and used to determine the time at which approximately 50% of the initial anticoagulant activity remains in the plasma ($T_{1/2}$).

The test compounds of formula I can also be administered to rats using an intraduodenal dosing protocol. Male Sprague-Dawley rats weighing approximately 300 g are anesthetized with a combination of ketamine/xylazine, subcutaneously, following an approved protocol. The right carotid artery is cannulated for blood sampling. A laparotomy is performed and duodenum is cannulated with a ball-tip needle and tied into place to ensure that the suture is distal to the point of insertion. An additional tie is placed proximal to the insertion point to prevent leakage of gastric contents. The effectiveness of the suture in preventing a compound from reaching the site of insertion is tested by pressure testing at the conclusion of each experiment. The point of insertion is approximately 4 cm from the duodenal-gastric junction. Compounds are administered in 1 ml normal saline. A 0.7 ml blood sample is drawn prior to administration of the test compound of formula I and at 15, 30, 60, 90 and 120 min after administration. Plasma is separated by centrifugation and assayed for inhibition of coagulation using the dilute prothrombin time assay.

c. Rat Arteriovenous Shunt Model of Thrombosis

The anti-thrombotic efficacy of various compounds of the invention may be assessed using rat extracorporeal arteriovenous (AV) shunt. The AV shunt circuit consisted of a 20 cm length of polyethylene (PE) 60 tubing inserted into the right carotid artery, a 6 cm length of PE 160 tubing containing a 6.5 cm length of mercerized cotton thread (5 cm exposed to blood flow), and a second length of PE 60 tubing (20 cm) completing the circuit into the left jugular vein. The entire circuit is filled with normal saline prior to insertion.

Test compounds of formula I are administered by continuous infusion into the tail vein using a syringe pump and butterfly catheter (infusion volume 1.02 ml/h). A compound is administered for 30 min, then the shunt is opened and blood allowed to flow for a period of 15 min (total of 45 min infusion). At the end of the 15 min period, the shunt is clamped and the thread is carefully removed and weighed on an analytical balance. Percent inhibition of thrombus formation is calculated using the thrombus weight obtained from control rats, which are infused with saline.

The following Table 1 shows the factor Xa inhibitory activities ($K_i$-values) of selected compounds of the formula I (testing the compounds for inhibitory activity was accomplished using the in vitro Factor Xa assay described above (Test 1a).

TABLE 1

| Factor Xa inhibitory activity ($K_i$-values): | |
|---|---|
| Example | Ki (FXa) [μM] |
| 3 | 0.1558 |
| 5 | 0.0006 |
| 6 | 0.0010 |
| 8 | 0.0351 |
| 10 | 0.6040 |
| 14 | 0.0218 |
| 17 | 2.29 |
| 21 | 8.37 |
| 28 | 0.047 |
| 30 | 0.153 |
| 38 | 1.1 |
| 40 | 0.0107 |
| 45 | 26.5 |
| 54 | 3.01 |
| 56 | 0.0021 |
| 58 | 0.0575 |
| 61 | 0.957 |
| 69 | 0.285 |
| 72 | 4.3 |
| 82 | 0.0393 |
| 89 | 6.48 |
| 92 | 5.93 |
| 94 | 1.7 |
| 97 | 0.04 |
| 104 | 6.5 |

TABLE 1-continued

| Factor Xa inhibitory activity ($K_i$-values): | |
|---|---|
| Example | Ki (FXa) [μM] |
| 129 | 0.36 |
| 136 | 0.01 |
| 144 | 0.011 |
| 154 | |

EXAMPLES

The following examples present typical syntheses of the compounds of formula I. These examples are understood to be illustrative only and are not intended to limit the scope of the present invention in any way. The compounds of the examples were characterized by mass spectra (MS) and/or NMR spectra and/or melting point. When in the final step of the synthesis of a compound an acid such as trifluoroacetic acid or acetic acid was used, for example when trifluoroacetic acid was employed to remove a tert-butyl group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt or hydrochloric acid salt.

Example 1

General Method for Synthesis of Malonic Acids Derivatives on Solid Phase

General solid-phase peptide synthesis was used to produce most of the compounds of this invention. Such methods were described, for example, by Steward and Young (Solid Phase Peptide Synthesis (Freeman and Co., San Francisco, 1969), which is incorporated herein by reference. Unless indicated otherwise, compounds were synthesized on polystyrene resin cross-linked with 1% divinylbenzene. An acid sensitive linker (Rink Linker) was coupled to the solid support (Rink, Tetr. Left. 28:3787 (1987); Sieber, Tetr. Lett. 28:2107 (1987), each of which is incorporated herein by reference). All compounds were synthesized on a semi-automated peptide synthesizer built in house. Boc-and Fmoc-protected L- and D-amino acid derivatives were from various commercial sources like Advanced ChemTech (Louisville, Ky. 40228–9973, USA); Bachem (King of Prussia, Pa. 19406, USA) and PerSeptive Biosystems (Framingham, Mass. 01701, USA).

Synthesis of compounds of the formula I was carried out according to the classical Fmoc methodology (E. Atherton and R. C. Sheppard in "Solid Phase Peptide Synthesis: A Practical Approach", IRL Press, Oxford, England, 1989) using diisopropyl-carbodiimide and benzotriazol-1-ol as activating reagents. All couplings were done in dimethylformamide or dimethylformamide: dichloromethane (1:1 mixture) at room temperature for 40 min. Completion of coupling was monitored by a ninhydrin test as described by Kaiser (Kaiser et al., Anal. Biochem. 34:595 (1970)), which is incorporated herein by reference. A second (double) coupling was performed where coupling in the first instance was incomplete.

After completion of peptide assembly on the resin, the final Fmoc deprotection was performed then followed by normal wash cycles and determination of the amount of Fmoc group released by deprotection at 302 nm. Then the malonic acid derivatives were similarly coupled by diisopropyl-carbodiimide/benzotriazol-1-ol procedure. The finished resin was washed successively with dichloromethane, dimethylformamide and dichloromethane, then dried under vacuum and used in the next step.

Solid-Phase Synthesis of Amidoxime

The general procedure was by mixing the resin (from the step above) of the nitrile containing substance with 20–40 equivalents of hydroxylamine hydrochloride in presence of 1:1:1 (by volumes) mixture of triethylamine, pyridine and dimethylformamide. The suspension was usually sonnicated for about 30 sec. and shaken at room temperature for 12–24 hours. The completion of conversion of nitrile to amidoxime was monitored by either FT-IR (KBr disk) to look for the disappearance of—CN absorption at 2225 $cm^{-1}$ or by cleavage of small sample of the resin by trifluoroacetic acid: $H_2O$ (95:5) or reagent K (see below) and determination of the molecular weight by electrospray mass spectroscopy. The finished resin was washed with dimethylformamide, 10% $H_2O$ in dimethylformamide, ethanol, dichloromethane and dried in vacuum before its use in the next step.

Solid-Phase Synthesis of Amidine

Several methods were reported for the synthesis of amidine-containing compounds (for review see P. J. Dunn (1995) in "Comprehensive Organic Functional Group Transformations: Amidines and N-Substituted Amidines", Vol. 5, 741–782 (edts. Alan R. Katritzky, Otto Meth-Cohen & Charles W. Rees), Pergamon, N.Y., 1995). None of these methods were compatible with the solid-phase organic synthesis. Here we developed the proper procedure of amidine synthesis via amidoxime precursor by reduction using excess triethylsilane in presence of soluble catalyst (dichlorotetrakis (triphenylphosphine) ruthenium (II), DCRu). It was found that addition of triphenylphosphine in presence of acetic acid facilitated the reduction and enhanced the yield of amidine compounds. In a typical experiment the dried resin was added to the reduction cocktail composed of DCRu, triphenylphosphine, acetic acid, dimethylformamide and triethylsilane in a stoppered reaction vessel (see example 4/5). The reduction usually took 12–24 hours at room temperature. Additional triethylsilan was used in case of incomplete reduction and the time of reaction was extended by 4–8 additional hours. The finished peptidomimetic resin was washed with dimethylformamide, ethanol, dichloromethane and suspended in reagent K (King et al., Int. J. Pept. Prot. Res. 36:255–266 (1990)) cocktail (5 ml/g peptide resin) for 180 min at room temperature. Then the cleavage mixture was filtered in anhydrous diethyl ether and the solid precipitate was isolated by centrifugation and dried in vacuum over solid pellets of KOH and the solid material was dissolved in a mixture of 1:1 of 0.1% trifluoroacetic acid in water and acetonitrile and lyophilized.

For purification of the compounds of formula I, a sample of crude lyophilized compound was dissolved in a mixture of 0.1% aqueous trifluoroacetic acid containing 10% to 50% acetonitrile. The compound solution usually filtered through a syringe connected to a 0.45 $\mu$m nylon ACRODISCO® 13 (Gelman Sciences; Ann Arbor Mich.) filter. A proper volume of filtered peptidomimetic solution was injected into a semi-preparative C18 column (Vydac Protein and Peptide C18, 218TP1010; The Separation Group; Hesperia Calif.). The flow rate of a gradient or isocratic mixture of 0.1% trifluoroacetic acid buffer and acetonitrile (HPLC grade) as an eluent was maintained using a Beckman SYSTEM GOLD® HPLC. Elution of the peptidomimetic was monitored by UV detection at 230 nm (Beckman, SYSTEM GOLD®, Programmable Solvent Module 126 and Programmable Detector Module 166 controlled by SYSTEM GOLD® software). After identifying the peak corresponding to each diastereomer using MS, the compounds were collected, lyophilized and biologically tested. MS was performed using a SCIEX API III+instrument. In addition, NMR was performed using a General Electric instrument (300 MHz) or Bruker Avance DPX 300 (300 MHz). For NMR, samples typically were measured in DMSO-$d_6$ or $CDCl_3$ (Aldrich).

Typical synthesis of individual compounds is summarized in Scheme 6 and the following examples illustrate the experimental details.

Examples 2 and 3

N-[(1-(S)-Carbamoyl-4-guanidino-butylcarbamoyl)-(S)-cyclohexyl-methyl]-2-[4-(N-hydroxycarbamimidoyl)-benzyl]-N',N'-dimethyl-malonamide trifluoroacetic acid salt, more polar diastereomer and N-[(1-(S)-Carbamoyl-4-guanidino-butylcarbamoyl)-(S)-cyclohexyl-methyl]-2-[4-(N-hydroxycarbamimidoyl)-benzyl]-N',N'-dimethyl-malonamide trifluoroacetic acid salt, less polar diastereomer a) N-[(1-(S)-{Carbonyl-(Rink-resin)}-4-(bis-tert-butoxycarbonyl-guanidino)-butylcarbamoyl)-(S)-cyclohexyl-methyl]-2-(R,S)-(4-cyano-benzyl)-N',N'-dimethyl-malonamide Fmoc-deprotected Rink resin (210 mg, 0.16 mmol) was coupled to 2-(Fmoc-amino)-4-(S)-(N,N'-bis-tert-butoxycarbonyl-guanidino)-butyric acid (326 mg, 0.5 mmol, 2 eq.) using benzotriazol-1-ol and diisopropyl-carbodiimide (2 eq. of each) as outlined in example 1. After Fmoc-deprotection, the resin was coupled with (S)-cyclohexyl-(Fmoc-amino)-acetic acid (2 eq.) using the same coupling conditions. After Fmoc-deprotection the resin was coupled with 2-(R,S)-(4-cyano-benzyl)-N,N-dimethyl-malonamic acid (45 mg, 0.17 mmol, 1.1 eq.) using diisopropyl-carbodiimide/benzotriazol-1-ol (1.1 eq. each) in dimethylformamide for 4 hours at room temperature. The completion of the reaction was confirmed by ninhydrin test. The resin was washed with dimethylformamide, methanol and dichloromethane and dried in vacuo for 2–3 hours.

b) N-[(1-(S)-Carbamoyl-4-guanidino-butylcarbamoyl)-(S)-cyclohexyl-methyl]-2-(R)-[4-(N-hydroxycarbamimidoyl)-benzyl]-N',N'-dimethyl-malonamide trifluoroacetate and N-[(1-(R)-Carbamoyl4-guanidino-butylcarbamoyl)-(S)-cyclohexyl-methyl]-2-(S)-[4-(N-hydroxycarbamimidoyl)-benzyl]-N',N'-dimethyl-malonamide trifluoroacetate The dried resin from step a was transferred into a screw-capped 20-ml vial and mixed with hyroxylamine hydrochloride (350 mg, 5 mmole, 25 eq.). To the reaction vial was added a mixture of triethylamine, pyridine and dimethylformamide (1:1:1, 8 ml), the vial capped, and sonnicated for 30 sec. The reaction was rocked at room temperature over night. The completion of the reaction was checked as mentioned in example 1. The finished resin was split into two portions. One portion was cleaved and processed as outlined in example 1 to give the title compound. Analysis by MS gave M.Wt. 573.4 (cal. 573.3). The second portion of the resin was used in examples 4 and 5.

Examples 4 and 5

2-(4-Carbamimidoyl-benzyl)-N-[(1-carbamoyl-4-guanidino-butylcarbamoyl)-cyclohexyl-methyl]-N',N'-dimethyl-malonamide trifluoroacetic acid salt, diastereomeric mixture and less polar diastereomer A solution of dichlorotetrakis (triphenylphosphine) ruthenium (II) (20 mg) and triphenylphosphine (80 mg) in dimethylformamide (1 ml) and glacial acetic acid (135 µl) was heated at 50° C. for 10–15 minutes to give a clear brown colored solution. The reaction vial was cooled to room temperature and the second portion of the dried resin (100 mg) from example 2/3b was added followed by triethylsilane (1 ml). The vial was capped under $N_2$ and shaken at room temperature for 12 hours. Completion of reduction to amidine was monitored by cleavage of small amount of the resin and testing the product with HPLC/ESMS. The finished resin was washed with dimethylformamide, methanol, dichloromethane and processed as outlined in example 1. The lyophilized product (14 mg) was purified by HPLC and the two distereoisomers were separated. The purified product was analyzed by ESMS cal. 560.35; found 560.

Examples 6 and 7

2-(S)-{2-(S)-[2-(Benzyl-methyl-carbamoyl)-3-(4-carbamimidoyl-phenyl)-propionylamino]-2-cyclohexyl-acetylamino}-5-guanidino-pentanoic acid allyl ester trifluoroacetic acid salt, less polar diastereomer and 2-(S)-{2-(S)-[2-(Benzyl-methyl-carbamoyl)-3-(4-carbamimidoyl-phenyl)-propionylamino]-2-cyclohexyl-acetylamino}-5-guanidino-pentanoic acid allyl ester trifluoroacetic acid salt, more polar diastereomer a) N-Benzyl-2-(R,S)-(4-cyano-benzyl)-N-methyl-malonamic acid A solution of benzyl-methyl-amine (120 ml, 887 mmol), bis-(trimethylsilyl)-acetamide (118 ml, 482 mmol) and anhydrous dichloromethane (1000 ml) was heated to reflux for 3 hours. The reaction mixture was allowed to cool to room temperature and 4-(R,S)-(2,2-dimethyl-4,6-dioxo-[1,3]dioxan-5-ylmethyl)-benzonitrile (25 g, 97 mmol) was added portionwize. The reaction mixture was refluxed for further 3 hours, allowed to cool to room temperature and poured into a cool mixture of 1700 ml 1 n hydrochloric acid and 800 ml ethylacetate, brought to pH 4 with 6 n sodium hydroxide solution, and extracted with ethylacetate and dichloromethane. The combined organic layers were washed with brine, dried and concentrated in vacuo.

The precipitated crystals were suctioned off and dried to give 25.0 g (80%) of the desired product. mp: 152–153° C. (dc).

b) (S)-[2-(Benzyl-methyl-carbamoyl)-3-(R,S)-(4-cyano-phenyl)-propionylamino]-cyclohexyl-acetic acid methyl ester A solution of N-benzyl-2-(R,S)-(4-cyano-benzyl)-N-methyl-malonamic acid (25.0 g, 78 mmol), (S)-amino-cyclohexyl-acetic acid methyl ester (14.2 g, 83 mmol), diisopropylethylamine (16 ml, 94 mmol), 3-hydroxy-3H-benzo[d][1,2,3]triazin-4-one (3.2 g, 20 mmol), and dimethylformamide (520 ml) was cooled to 10° C. A solution of dicyclohexyl-carbodiimide (18.7 g, 91 mmol) in toluene (30 ml) was added dropwise and the reaction mixture stood over night. The precipitated urea was suctioned off, the filtrate was evaporated in vacuo, dissolved in ethylacetate, washed with saturated sodium hydrogen carbonate solution and brine, dried, and evaporated in vacuo. Crystallization from n-heptane/isopropanol gave 6.3 g (17%) of the desired product. mp: 119–120° C.

The filtrate was evaporated and purified by column chromatography on silica gel with n-heptane/ethyl acetate=10/1 as eluent. Combined fractions gave 6.1 g (17%) of the desired product. mp: 120–121° C.

c) {2-(Benzyl-methyl-carbamoyl)-3-(R,S)-[4-(N-hydroxycarbamimidoyl)-phenyl]-propionylamino}-(S)-cyclohexyl-acetic acid methyl ester A suspension of [2-(benzyl-methyl-carbamoyl)-3-(R,S)-(4-cyano-phenyl)-propionylamino]-(S)-cyclohexyl-acetic acid methyl ester (12.0 g, 26 mmol) and hydroxylamine (4.3 g, 130 mmol) in ethanol (150 ml) was heated to reflux for 4 hours. The reaction mixture was cooled to room temperature, evaporated in vacuo, dissolved in ethanol and poured in ice-water. The precipitate was collected by suction and dried at 60° C. in vacuo to give 11.6 g (90%) of the desired product. mp: 135–138° C., MS: 509 (M+H).

d) [2-(Benzyl-methyl-carbamoyl)-3-(R,S)-(4-carbamimidoyl-phenyl)-propionylamino]-(S)-cyclohexyl-acetic acid methyl ester {2-(Benzyl-methyl-carbamoyl)-3-(R,S)-[4-(N-hydroxycarbamimidoyl)-phenyl]-propionylamino}-(S)-cyclohexyl-acetic acid methyl ester (11.0 g, 22 mmol) was hydrogenated in acetic acid with palladium/charcoal to give 9.2 g (77%) of the desired product which was used without further purification in the next step. mp: 123–124° C., MS: 493 (M+H)

e) [2-(Benzyl-methyl-carbamoyl)-3-(R,S)-(4-carbamimidoyl-phenyl)-propionylamino]-(S)-cyclohexyl-acetic acid trifluoroacetic acid salt The above [2-(benzyl-methyl-carbamoyl)-3-(R,S)-(4-carbamimidoyl-phenyl)-propionylamino]-(S)-cyclohexyl-acetic acid methyl ester (9.2 g, 19 mmol) was suspended in acetonitrile (350 ml), water/concentrated hydrochloric acid (1/1, 500 ml) was added and the reaction mixture was stirred at room temperature. After 4 days the reaction mixture was evaporated, water was added and the mixture was lyophilized. The product was purified by column chromatography on silica gel with dichloromethane/methanol/trifluoroacetic acid=15/110.5 to 4/1/0.5. Collected fractions gave 8.2 g (74%) of the desired product. MS: 479 (M+H).

f) 2-(S)-{2-(S)-[2-(Benzyl-methyl-carbamoyl)-3-(4-carbamimidoyl-phenyl)-propionylamino]-2-cyclohexyl-acetylamino}-5-guanidino-pentanoic acid allyl ester trifluoroacetic acid salt, less polar diastereomer and 2-(S)-{2-(S)-[2-(Benzyl-methyl-carbamoyl)-3-(4-carbamimidoyl-phenyl)-propionylamino]-2-cyclohexyl-acetylamino}-5-guanidino-pentanoic acid allyl ester trifluoroacetic acid salt, more polar diastereomer To a solution of [2-(benzyl-methyl-carbamoyl)-3-(R,S)-(4-carbamimidoyl-phenyl)-propionylamino]-(S)-cyclohexyl-acetic acid trifluoroacetic acid salt (2.9 g, 4.9 mmol) in dimethylformamide (350 ml) were added collidin (2.4 g, 19.6 mmol) and HATU (2.1 g, 5.4 mol) at 0° C. The reaction mixture was stirred at this temperature for 30 minutes, then (S)-2-amino-5-guanidino-pentanoic acid allyl ester (1.2 g, 4.9 mmol) was added. The reaction mixture was allowed to warm up to room temperature and stood for 60 hours. The solvent was evaporated in vacuo and the residue was purified by MPLC on $RP_{18}$ material using water/ethanol/trifluoroacetic acid (9/1/0.1 to 5/5/0.1) as eluent to give 1.0 g (23%) of the more polar diastereomer and 584 mg (13%) of the less polar diastereomer. Both fractions showed the correct MS spectrum. The following compounds were prepared using the procedures described above:

| Expl. | Name | MS | Method |
|---|---|---|---|
| 8 | N-Benzyl-2-(4-carbamimidoyl-benzyl)-N'-[(S)-(1-(S)-carbamoyl-4-guanidino-butylcarbamoyl)-cyclohexyl-methyl]-malonamide trifluoroacetic acid salt, more polar diastereomer | ok | solid phase |
| 9 | N-Benzyl-2-(4-carbamimidoyl-benzyl)-N'-[(S)-(1-(S)-carbamoyl-4-guanidino-butylcarbamoyl)-cyclohexyl-methyl]-malonamide trifluoroacetic acid salt, less polar diastereomer | ok | solid phase |
| 10 | 2-[3-(4-Carbamimidoyl-phenyl)-2-dimethylcarbamoyl-propionyl]-1,2,3,4-tetrahydro-isoquinoline-3-(S)-carboxylic acid (1-(S)-carbamoyl-4-guanidino-butyl)-amide trifluoroacetic acid salt | ok | solid phase |
| 11 | 2-(4-Carbamimidoyl-benzyl)-N'-[1-(S)-(1-(S)-carbamoyl-4-guanidino-butylcarbamoyl)-2-phenyl-ethyl]-N'-methyl-malonamide trifluoroacetic acid salt | ok | solid phase |
| 12 | N-Allyl-2-(4-carbamimidoyl-benzyl)-N'-[1-(S)-(1-(S)-carbamoyl-4-guanidino-butylcarbamoyl)-2-phenyl-ethyl]-malonamide trifluoroacetic acid salt | ok | solid phase |
| 13 | 2-(4-Carbamimidoyl-benzyl)-N-[1-(S)-(1-(S)-carbamoyl-4-guanidino-butylcarbamoyl)-2-phenyl-ethyl]-N'-phenyl-malonamide trifluoroacetic acid salt | ok | solid phase |
| 14 | N-Benzyl-N'-[(S)-(1-(S)-carbamoyl-4-guanidino-butylcarbamoyl)-cyclohexyl-methyl]-2-[4-(N-hydroxycarbamimidoyl)-benzyl]-malonamide trifluoroacetic acid salt | ok | solid phase |
| 15 | N-[2-(4-Amino-phenyl)-1-(S)-(1-(S)-carbamoyl-4-guanidino-butylcarbamoyl)-ethyl]-2-(4-carbamimidoyl-benzyl)-N'-methyl-malonamide trifluoroacetic acid salt | ok | solid phase |
| 16 | N-[2-(4-Amino-phenyl)-1-(S)-(1-(S)-carbamoyl-4-guanidino-butylcarbamoyl)-ethyl]-2-(4-carbamimidoyl-benzyl)-N', N'-dimethyl-malonamide trifluoroacetic acid salt | ok | solid phase |
| 17 | N-Allyl-N'-[2-(4-amino-phenyl)-1-(S)-(1-(S)-carbamoyl-4-guanidino-butylcarbamoyl)-ethyl]-2-(4-carbamimidoyl-benzyl)-malonamide trifluoroacetic acid salt | ok | solid phase |
| 18 | N-[2-(4-Amino-phenyl)-1-(S)-(1-(S)-carbamoyl-4-guanidino-butylcarbamoyl)-ethyl]-2-(4-carbamimidoyl-benzyl)-N-phenyl-malonamide trifluoroacetic acid salt | ok | solid phase |
| 19 | 2-(4-Carbamimidoyl-benzyl)-N-[1-(S)-(1-(S)-carbamoyl-4-guanidino-butylcarbamoyl)-2-methyl-butyl]-N,N'-dimethyl-malonamide | ok | solid phase |
| 20 | N-Allyl-2-(4-carbamimidoyl-benzyl)-N'-[1-(S)-(1-(S)-carbamoyl-4-guanidino-butylcarbamoyl)-2-methyl-butyl]-N'-methyl-malonamide trifluoroacetic acid salt | ok | solid phase |
| 21 | 2-(4-Carbamimidoyl-benzyl)-N-[1-(S)-(1-(S)-carbamoyl-4-guanidino-butylcarbamoyl)-2-methyl-butyl]-N-methyl-N'-phenyl-malonamide trifluoroacetic acid salt | ok | solid phase |
| 22 | 2-(4-Carbamimidoyl-benzyl)-N-[1-(S)-(1-(S)-carbamoyl-4-guanidino-butylcarbamoyl)-2-phenyl-ethyl]-N,N'-dimethyl-malonamide trifluoroacetic acid salt | ok | solid phase |
| 23 | N-Allyl-2-(4-carbamimidoyl-benzyl)-N'-[1-(S)-(1-(S)-carbamoyl-4-guanidino-butylcarbamoyl)-2-phenyl-ethyl]-N'-methyl-malonamide trifluoroacetic acid salt | ok | solid phase |
| 24 | 2-(4-Carbamimidoyl-benzyl)-N-[1-(S)-(1-(S)-carbamoyl-4-guanidino-butylcarbamoyl)-2-phenyl-ethyl]-N-methyl-N'-phenyl-malonamide trifluoroacetic acid salt | ok | solid phase |
| 25 | 2-(S)-[3-(4-Carbamimidoyl-phenyl)-2-methylcarbamoyl-propionyl]-1,2,3,4-tetrahydro-isoquinoline-3-carboxylic acid (1-(S)-carbamoyl-4-guanidino-butyl)-amide trifluoroacetic acid salt | ok | solid phase |
| 26 | 2-(S)-[2-Allylcarbamoyl-3-(4-carbamimidoyl-phenyl)-propionyl]-1,2,3,4-tetrahydro-isoquinoline-3-carboxylic acid (1-(S)-carbamoyl-4-guanidino-butyl)-amide trifluoroacetic acid salt | ok | solid phase |
| 27 | 2-(S)-[3-(4-Carbamimidoyl-phenyl)-2-phenylcarbamoyl-propionyl]-1,2,3,4-tetrahydro-isoquinoline-3-carboxylic acid (1-(S)-carbamoyl-4-guanidino-butyl)-amide trifluoroacetic acid salt | ok | solid phase |
| 28 | 2-(4-Carbamimidoyl-benzyl)-N-1-(S)-(1-(S)-carbamoyl-4-guanidino-butylcarbamoyl)-pentyl]-N'-methyl-malonamide trifluoroacetic acid salt | ok | solid phase |
| 29 | N-Allyl-2-(4-carbamimidoyl-benzyl)-N'-[1-(S)-(1-(S)-carbamoyl-4-guanidino-butylcarbamoyl)-pentyl]-malonamide trifluoroactic acid salt | ok | solid phase |
| 30 | 2-(4-Carbamimidoyl-benzyl)-N-[1-(S)-(1-(S)-carbamoyl-4-guanidino-butylcarbamoyl)-pentyl]-N'-phenyl-malonamide trifluoroactic acid salt | ok | solid phase |
| 31 | 4-(S)-[3-(4-Carbamimidoyl-phenyl)-2-methylcarbamoyl-propionylamino]-4-(1-(S)-carbamoyl-4-guanidino-butylcarbamoyl)-butyric acid trifluoroactic acid salt | ok | solid phase |
| 32 | 4-(S)-[3-(4-Carbamimidoyl-phenyl)-2-dimethylcarbamoyl-propionylamino]-4-(1-(S)-carbamoyl-4-guanidino-butylcarbamoyl)-butyric acid | ok | solid phase |
| 33 | 4-(S)-[2-Allylcarbamoyl-3-(4-carbamimidoyl-phenyl)-propionylamino]-4-(1-(S)-carbamoyl-4-guanidino-butylcarbamoyl)-butyric acid trifluoroacetic acid salt | ok | solid phase |
| 34 | 4-(S)-[3-(4-Carbamimidoyl-phenyl)-2-phenylcarbamoyl-propionylamino]-4-(1-(S)-carbamoyl-4-guanidino-butylcarbamoyl)-butyric acid | ok | solid phase |
| 35 | 2-(4-Carbamimidoyl-benzyl)-N-[1-(S)-(1-(S)-carbamoyl-4-guanidino-butylcarbamoyl)-2-naphthalen-2-yl-ethyl]-N'-methyl-malonamide trifluoroacetic acid salt | ok | solid phase |
| 36 | 2-(4-Carbamimidoyl-benzyl)-N-[1-(S)-(1-(S)-carbamoyl-4-guanidino-butylcarbamoyl)-2-naphthalen-2-yl-ethyl]-N',N'-dimethyl-malonamide trifluoroacetic acid salt | ok | solid phase |
| 37 | N-Allyl-2-(4-carbamimidoyl-benzyl)-N'-[1-(S)-(1-(S)-carbamoyl-4-guanidino-butylcarbamoyl)-2-naphthalen-2-yl-ethyl]-malonamide trifluoroacetic acid salt | ok | solid phase |
| 38 | 2-(4-Carbamimidoyl-benzyl)-N-[1-(S)-(1-(S)-carbamoyl-4-guanidino-butylcarbamoyl)-2-naphthalen-2-yl-ethyl]-N'-phenyl-malonamide trifluoroacetic acid | ok | solid phase |
| 39 | 2-(4-Carbamimidoyl-benzyl)-N-[1-(S)-(1-(S)-carbamoyl-4-guanidino-butylcarbamoyl)-3-phenyl-propyl]-N'-methyl-malonamide trifluoroacetic acid salt | ok | solid phase |
| 40 | 2-(4-Carbamimidoyl-benzyl)-N-[1-(S)-(1-(S)-carbamoyl-4-guanidino-butylcarbamoyl)-3-phenyl-propyl]-N',N'-dimethyl-malonamide trifluoroacetic acid salt | ok | solid phase |
| 41 | N-Allyl-2-(4-carbamimidoyl-benzyl)-N'-[1-(S)-(1-(S)-carbamoyl-4-guanidino-butylcarbamoyl)-3-phenyl-propyl]-malonamide trifluoroacetic acid salt | ok | solid phase |
| 42 | 2-(4-Carbamimidoyl-benzyl)-N-[1-(S)-(1-(S)-carbamoyl-4-guanidino-butylcarbamoyl)-3-phenyl-propyl]-N'-phenyl-malonamide trifluroacetic acid salt | ok | solid phase |
| 43 | N-[4-Amino-1-(S)-(1-(S)-carbamoyl-4-guanidino-butylcarbamoyl)-butyl]-2-(4-carbamimidoyl-benzyl)-N'-methyl-malonamide trifluoroacetic acid salt | ok | solid phase |
| 44 | N-[4-Amino-1-(S)-(1-(S)-carbamoyl-4-guanidino-butylcarbamoyl)-butyl]-2-(4-carbamimidoyl-benzyl)-N',N'-dimethyl-malonamide trifluoroacetic acid salt | ok | solid phase |
| 45 | N-Allyl-N'-[4-amino-1-(S)-(1-(S)-carbamoyl-4-guanidino-butylcarbamoyl)-butyl]-2-(4-carbamimidoyl-benzyl)-malonamide trifluoroacetic acid salt | ok | solid phase |
| 46 | N-[4-Amino-1-(S)-(1-(S)-carbamoyl-4- | ok | solid |

| Expl. | Name | MS | Method |
|---|---|---|---|
| | guanidino-butylcarbamoyl)-butyl]-2-(4-carbamimidoyl-benzyl)-N'-phenyl-malonamide trifluoroacetic acid salt | | phase |
| 47 | 3-(S)-[3-(4-Carbamimidoyl-phenyl)-2-methylcarbamoyl-propionylamino]-N-(1-(S)-carbamoyl-4-guanidino-butyl)-succinamic acid trifluoroacetic acid salt | ok | solid phase |
| 48 | 3-(S)-[3-(4-Carbamimidoyl-phenyl)-2-dimethylcarbamoyl-propionylamino]-N-(1-(S)-carbamoyl-4-guanidino-butyl)-succinamic acid trifluoroacetic acid salt | ok | solid phase |
| 49 | 3-(S)-[2-Allylcarbamoyl-3-(4-carbamimidoyl-phenyl)-propionylamino]-N-(1-(S)-carbamoyl-4-guanidino-butyl)-succinamic acid trifluoroacetic acid salt | ok | solid phase |
| 50 | 3-(S)-[3-(4-Carbamimidoyl-phenyl)-2-phenylcarbamoyl-propionylamino]-N-(1-(S)-carbamoyl-4-guanidino-butyl)-succinamic acid trifluoroacetic acid salt | ok | solid phase |
| 51 | 2-(4-Carbamimidoyl-benzyl)-N-[1-(S)-(1-(S)-carbamoyl-4-guanidino-butylcarbamoyl)-2-hydroxy-ethyl]-N'-methyl-malonamide trifluoroacetic acid salt | ok | solid phase |
| 52 | 2-(4-Carbamimidoyl-benzyl)-N-[1-(S)-(1-(S)-carbamoyl-4-guanidino-butylcarbamoyl)-2-hydroxy-ethyl]-N',N'-dimethyl-malonamide trifluoroacetic acid salt | ok | solid phase |
| 53 | N-Allyl-2-(4-carbamimidoyl-benzyl)-N'-[1-(S)-(1-(S)-carbamoyl-4-guanidino-butylcarbamoyl)-2-hydroxy-ethyl]-malonamide trifluoroacetic acid salt | ok | solid phase |
| 54 | 2-(4-Carbamimidoyl-benzyl)-N-[1-(S)-(1-(S)-carbamoyl-4-guanidino-butylcarbamoyl)-2-hydroxy-ethyl]-N'-phenyl-malonamide trifluoroacetic acid salt | ok | solid phase |
| 55 | 2-(4-Carbamimidoyl-benzyl)-N-[(S)-(1-(S)-carbamoyl-4-guanidino-butylcarbamoyl)-phenyl-methyl]-N'-methyl-malonamide trifluoroacetic acid salt | ok | solid phase |
| 56 | 2-(4-Carbamimidoyl-benzyl)-N-[(S)-(1-(S)-carbamoyl-4-guanidino-butylcarbamoyl)-phenyl-methyl]- N',N'-dimethyl-malonamide trifluoroacetic acid salt | ok | solid phase |
| 57 | N-Allyl-2-(4-carbamimidoyl-benzyl)-N'-[(S)-(1-(S)-carbamoyl-4-guanidino-butylcarbamoyl)-phenyl-methyl]-malonamide trifluoroacetic acid salt | ok | solid phase |
| 58 | 2-(4-Carbamimidoyl-benzyl)-N-[(S)-(1-(S)-carbamoyl-4-guanidino-butylcarbamoyl)-phenyl-methyl]- N'-phenyl-malonamide trifluoroacetic acid salt | ok | solid phase |
| 59 | N-[2-Benzyloxy-1-(S)-(1-(S)-carbamoyl-4-guanidino-butylcarbamoyl)-ethyl]-2-(4-carbamimidoyl-benzyl)-N'-methyl-malonamide trifluoroacetic acid salt | ok | solid phase |
| 60 | N-[2-Benzyloxy-1-(S)-(1-(S)-carbamoyl-4-guanidino-butylcarbamoyl)-ethyl]-2-(4-carbamimidoyl-benzyl)-N',N'-dimethyl-malonamide trifluoroacetic acid salt | ok | solid phase |
| 61 | N-Allyl-N'-[2-benzyloxy-1-(S)-(1-(S)-carbamoyl-4-guanidino-butylcarbamoyl)-ethyl]-2-(4-carbamimidoyl-benzyl)-malonamide trifluoroacetic acid salt | ok | solid phase |
| 62 | N-[2-Benzyloxy-1-(S)-(1-(S)-carbamoyl-4-guanidino-butylcarbamoyl)-ethyl]-2-(4-carbamimidoyl-benzyl)-N'-phenyl-malonamide trifluoroacetic acid salt | ok | solid phase |
| 63 | [5-(S)-[3-(4-Carbamimidoyl-phenyl)-2-ethylcarbamoyl-propionylamino]-5-(1-(S)-carbamoyl-4-guanidino-butylcarbamoyl)-pentyl]-carbamic acid benzyl ester | ok | solid phase |
| 64 | [5-(S)-[3-(4-Carbamimidoyl-phenyl)-2-imethylcarbamoyl-propionylamino]-5-(1-(S)-carbamoyl-4-guanidino-butylcarbamoyl)-pentyl]-carbamic acid benzyl ester | ok | solid phase |
| 65 | [5-(S)-[2-Allylcarbamoyl-3-(4-carbamimidoyl-phenyl)-propionylamino]-5-(1-(S)-carbamoyl-4-guanidino-butylcarbamoyl)-pentyl]-carbamic acid benzyl ester | ok | solid phase |
| 66 | [5-(S)-[3-(4-Carbamimidoyl-phenyl)-2-phenylcarbamoyl-propionylamino]-5-(1-(S)-carbamoyl-4-guanidino-butylcarbamoyl)-pentyl]-carbamic acid benzyl ester | ok | solid phase |
| 67 | 2-(4-Carbamimidoyl-benzyl)-N-[1-(S)-(1-(S)-carbamoyl-4-guanidino-butylcarbamoyl)-pentyl]-N',N'-dimethyl-malonamide trifluoroacetic acid salt, more polar diastereomer | ok | solid phase |
| 68 | 2-(4-Carbamimidoyl-benzyl)-N-[1-(S)-(1-(S)-carbamoyl-4-guanidino-butylcarbamoyl)-pentyl]-N',N'-dimethyl-malonamide trifluoroacetic acid salt, less polar diastereomer | ok | solid phase |
| 69 | 4-(S)-[3-(4-Carbamimidoyl-phenyl)-2-dimethylcarbamoyl-propionylamino]-4-[1-(S)-(1-(S)-carbamoyl-2-cyclohexyl-ethylcarbamoyl)-4-guanidino-butylcarbamoyl]-butyric acid trifluoroacetic acid salt | ok | solid phase |
| 70 | 4-(S)-[3-(4-Carbamimidoyl-phenyl)-2-methylcarbamoyl-propionylamino]-4-[1-(S)-(1-(S)-carbamoyl-2-cyclohexyl-ethylcarbamoyl)-4-guanidino-butylcarbamoyl]-butyric acid trifluoroacetic acid salt | ok | solid phase |
| 71 | 2-(4-Carbamimidoyl-benzyl)-N-[1-(S)-(1-(S)-carbamoyl-4-guanidino-butylcarbamoyl)-pentyl]-N',N'-dimethyl-malonamide trifluoroacetic acid salt trifluoroacetic acid salt | ok | solid phase |
| 72 | 2-(S)-{2-(R)-[3-(4-Carbamimidoyl-phenyl)-2-dimethylcarbamoyl-propionylamino]-hexanoylamino}-5-guanidino-pentanoic acid trifluoroacetic acid salt | ok | solid phase |
| 73 | 2-(S)-{2-(R)-[3-(4-Carbamimidoyl-phenyl)-2-methylcarbamoyl-propionylamino]-hexanoylamino}-5-guanidino-pentanoic acid trifluoroacetic acid salt | ok | solid phase |
| 74 | 2-(S)-{2-(R)-[2-Benzylcarbamoyl-3-(4-carbamimidoyl-phenyl)-propionylamino]-hexanoylamino}-5-guanidino-pentanoic acid trifluoroacetic acid salt | ok | solid phase |
| 75 | 2-(4-Carbamimidoyl-benzyl)-N-{1-(S)-[1-(S)-carbamoyl-2-(4-hydroxy-phenyl)-ethylcarbamoyl]-pentyl}-N',N'-dimethyl-malonamide trifluoroacetic acid salt | ok | solid phase |
| 76 | 2-(3-Carbamimidoyl-benzyl)-N-{1-(S)-[1-(S)-carbamoyl-2-(4-hydroxy-phenyl)-ethylcarbamoyl]-pentyl}-N',N'-dimethyl-malonamide trifluoroacetic acid salt | ok | solid phase |
| 77 | 2-(S)-{2-(S)-[3-(4-Carbamimidoyl-phenyl)-2-dimethylcarbamoyl-propionylamino]-hexanoylamino}-5-guanidino-pentanoic acid trifluoroacetic acid salt | ok | solid phase |
| 78 | 2-(S)-{2-(S)-[3-(4-Carbamimidoyl-phenyl)-2-methylcarbamoyl-propionylamino]-hexanoylamino}-5-guanidino-pentanoic acid trifluoroacetic acid salt | ok | solid phase |
| 79 | 2-(S)-{2-(S)-[2-Benzylcarbamoyl-3-(4-carbamimidoyl-phenyl)-propionylamino]-hexanoylamino}-5-guanidino-pentanoic acid trifluoroacetic acid salt | ok | solId phase |
| 80 | 2-(S)-{2-(S)-[3-(4-Carbamimidoyl-phenyl)-2-dimethylcarbamoyl-propionylamino]-2-cyclohexyl-acetylamino}-5-guanidino-pentanoic acid; compound with trifluoro-acetic acid trifluoroacetic acid salt | ok | solid phase |
| 81 | 2-(S)-{2-(S)-[3-(4-Carbamimidoyl-phenyl)-2-methylcarbamoyl-propionylamino]-2-cyclohexyl-acetylamino}-5-guanidino-pentanoic acid trifluoroacetic acid salt | ok | solid phase |
| 82 | 2-(S)-{2-(S)-[2-Benzylcarbamoyl-3-(4-carbamimidoyl-phenyl)-propionylamino]-2-cyclohexyl-acetylamino}-5-guanidino-pentanoic acid trifluoroacetic acid salt | ok | solid phase |
| 83 | 2-(S)-{2-(S)-[3-(4-Carbamimidoyl-phenyl)-2-dimethylcarbamoyl-propionylamino]-3- | ok | solid phase |

-continued

| Expl. | Name | MS | Method |
|---|---|---|---|
| | cyclohexyl-propionylamino}-5-guanidino-pentanoic acid trifluoroacetic acid salt | | |
| 84 | 2-(S)-{2-(S)-[3-(4-Carbamimidoyl-phenyl)-2-methylcarbamoyl-propionylamino]-3-cyclohexyl-propionylamino}-5-guanidino-pentanoic acid trifluoroacetic acid salt | ok | solid phase |
| 85 | 2-(S)-{2-(S)-[2-Benzylcarbamoyl-3-(4-carbamimidoyl-phenyl)-propionylamino]-3-cyclohexyl-propionylamino}-5-guanidino-pentanoic acid trifluoroacetic acid salt | ok | solid phase |
| 86 | 2-(4-Carbamimidoyl-benzyl)-N-[1-(R)-(1-(R)-carbamoyl-4-guanidino-butylcarbampyl)-2-cyclohexyl-ethyl]-N',N'-dimethyl-malonamide trifluoroacetic acid salt | ok | solid phase |
| 87 | 2-(3-Carbamimidoyl-benzyl)-N-[1-(S)-(1-(S)-carbamoyl-4-guanidino-butylcarbamoyl)-pentyl]-N',N'-dimethyl-malonamide trifluoroacetic acid salt | ok | solid phase |
| 88 | 4-(S)-[3-(4-Carbamimidoyl-phenyl)-2-phenylcarbamoyl-propionylamino]-4-[1-(S)-(1-(S)-carbamoyl-2-cyclohexyl-ethylcarbamoyl)-4-guanidino-butylcarbamoyl]-butyric acid trifluoroacetic acid salt | ok | solid phase |
| 89 | 4-(S)-[2-Allylcarbamoyl-3-(4-carbamimidoyl-phenyl)-propionylamino]-4-[1-(S)-(1-(S)-carbamoyl-2-cyclohexyl-ethylcarbamoyl)-4-guanidino-butylcarbamoyl]-butyric acid trifluoroacetic acid salt | ok | solid phase |
| 90 | 2-(4-Carbamimidoyl-benzyl)-N-[(S)-(2-carbamimidoyl-1-(S)-carbamoyl-ethylcarbamoyl)-cyclohexyl-methyl]-N',N'-dimethyl-malonamide trifluoroacetic acid salt, more polar diastereomer | ok | solid phase |
| 91 | 2-(4-Carbamimidoyl-benzyl)-N-[(S)-(2-carbamimidoyl-1-(S)-carbamoyl-ethylcarbamoyl)-cyclohexyl-methyl]-N',N'-dimethyl-malonamide trifluoroacetic acid salt, less polar diastereomer | ok | solid phase |
| 92 | 2-(4-Carbamimidoyl-benzyl)-N-{1-(S)-[(3-carbamimidoyl-benzyl)-carbamoylmethyl-carbamoyl]-pentyl}-N',N'-dimethyl-malonamide trifluoroacetic acid salt | ok | solid phase |
| 93 | 2-(4-Carbamimidoyl-benzyl)-N-((S)-{1-(S)-[1-(S)-(2-(S)-carbamoyl-pyrrolidine-1-carbonyl)-3-methyl-butylcarbamoyl]-4-guanidino-butylcarbamoyl}-cyclohexyl-methyl)-N',N'-diisopropyl-malonamide trifluoroacetic acid salt, less polar diastereomer | ok | solid phase |
| 94 | 3-{2-(S)-{2-(S)-[3-(4-Carbamimidoyl-phenyl)-2-diisopropylcarbamoyl-propionylamino]-2-cyclohexyl-acetylamino}-2-[1-(S)-(2-(S)-carbamoyl-pyrrolidime-1-carbonyl)-3-methyl-butylcarbamoyl]-ethyl}-1-methyl-pyridinium trifluoro-acetate trifluoroacetic acid, more polar diastereomer | ok | solid phase |
| 95 | 3-{2-(S)-{2-(S)-[3-(4-Carbamimidoyl-phenyl)-2-diisopropylcarbamoyl-propionylamino]-2-cyclohexyl-acetylamino}-2-[1-(S)-(2-(S)-carbamoyl-pyrrolidime-1-carbonyl)-3-methyl-butylcarbamoyl]-ethyl}-1- methyl-pyridinium trifluoro-acetate trifluoroacetic acid, less polar diastereomer | ok | solid phase |
| 96 | 2-(4-Amino-benzyl)-N-((S)-{1-(S)-[1-(S)-(2-(S)-carbamoyl-pyrrolidime-1-carbonyl)-3-methyl-butylcarbamoyl]-4-guanidino-butylcarbamoyl}-cyclohexyl-methyl)-N',N'-diisopropyl-malonamide trifluoroacetic acid salt, more polar diastereomer | ok | solid phase |
| 97 | 2-(4-Amino-benzyl)-N-((S)-{1-(S)-[1-(S)-(2-(S)-carbamoyl-pyrrolidine-1-carbonyl)-3-methyl-butylcarbamoyl]-4-guanidino-butylcarbamoyl}-cyclohexyl-methyl)-N',N'-diisopropyl malonamide trifluoroacetic acid salt, less polar diastereomer | ok | solid phase |
| 98 | 2-(4-Carbamimidoyl-benzyl)-N-((S)-{1-(S)-(2-(S)-carbamoyl-pyrrolidine-1-carbonyl)-3-methyl-butylcarbamoyl]-4-guanidino-butylcarbamoyl}-cyclohexyl-methyl)-N',N'-diisobutyl-malonamide trifluoroacetic acid salt, more polar diastereomer | ok | solid phase |
| 99 | 2-(4-Carbamimidoyl-benzyl)-N-((S)-{1-(S)-[1-(S)-(2-(S)-carbamoyl-pyrrolidine-1-carbonyl)-3-methyl-butylcarbamoyl]-4-guanidino-butylcarbamoyl}-cyclohexyl-methyl)-N',N'-diisobutyl-malonamide trifluoroacetic acid salt, less polar diastereomer | ok | solid phase |
| 100 | N-[(S)-(1-(S)-Carbamoyl-4-guanidino-butylcarbamoyl)-cyclohexyl-methyl]-2-(4-dimethylamino-naphthalen-2-ylmethyl)-N',N'-diisopropyl-malonamide trifluoroacetic acid salt, more polar diastereomer | ok | solid phase |
| 101 | N-[(S)-(1-(S)-Carbamoyl-4-guanidino-butylcarbamoyl)-cyclohexyl-methyl]-2-(4-dimethylamino-naphthalen-2-ylmethyl)-N',N'-diisopropyl-malonamide trifluoroacetic acid salt, less polar diastereomer | ok | solid phase |
| 102 | N-[(S)-(1-(S)-Carbamoyl-4-guanidino-butylcarbamoyl)-cyclohexyl-methyl]-2-[4-(N-hydroxycarbamimidoyl)-benzyl]-N',N'-dimethyl-malonamide trifluoroacetic acid salt, more polar diastereomer | ok | solid phase |
| 103 | N-[(S)-(1-(S)-Carbamoyl-4-guanidino-butylcarbamoyl)-cyclohexyl-methyl]-2-[4-(N-hydroxycarbamimidoyl)-benzyl]-N',N'-dimethyl-malonamide trifluoroacetic acid salt, less polar diastereomer | ok | solid phase |
| 104 | 2-(4-Carbamimidoyl-benzyl)-N-[(S)-(carbamoylmethyl-pyridin-4-yl methyl-carbamoyl)-cyclohexyl-methyl]-N',N'-dimethyl-malonamide trifluoroacetic acid salt, more polar diastereomer | ok | solid phase |
| 105 | 2-(4-Carbamimidoyl-benzyl)-N-[(S)-(carbamoylmethyl-pyridin-4-ylmethyl-carbamoyl)-cyclohexyl-methyl]-N',N'-dimethyl-malonamide trifluoroacetic acid salt, less polar diastereomer | ok | class. Synth. |
| 106 | N-{(S)-[4-Amino-butyl)-carbamoylmethyl-carbamoyl]-cyclohexyl-methyl}-2-(4-carbamimidoyl-benzyl)-N',N'-dimethyl-malonamide trifluoroacetic acid salt, more polar diastereomer | ok | solid phase |
| 107 | N-{(S)-[(4-Amino-butyl)-carbamoylmethyl-carbamoyl]-cyclohexyl-methyl}-2-(4-carbamimidoyl-benzyl)-N',N'-dimethyl-malonamide trifluoroacetic acid salt, less polar diastereomer | ok | class. Synth. |
| 108 | 2-(4-Carbamimidoyl-benzyl)-N-[1-(S)-(1-(S)-carbamoyl-4-guanidino-butylcarbamoyl)-2-phenyl-ethyl]-N',N'-dimethyl-malonamide trifluoroacetic acid salt, less polar diastereomer | ok | class. Synth. |
| 109 | 2-(4-Carbamimidoyl-benzyl)-N-[1-(S)-(1-(S)-carbamoyl-4-guanidino-butylcarbamoyl)-2-phenyl-ethyl]-N',N'-dimethyl-malonamide trifluoroacetic acid salt, more polar diastereomer | ok | class. Synth. |
| 110 | 2-(4-Carbamimidoyl-benzyl)-N-[1-(S)-(1-(S)-carbamoyl-4-guanidino-butylcarbamoyl)-2-naphthalen-1-yl-ethyl]-N',N'-dimethyl-malonamide trifluoroacetic acid salt | ok | class. Synth. |
| 111 | 2-(4-Carbamimidoyl-benzyl)-N-[1-(S)-(1-(S)-carbamoyl-4-guanidino-butylcarbamoyl)-2-methyl-butyl]-N ,N',N'-trimethyl-malonamide trifluoroacetic acid salt | ok | solid phase |
| 112 | 2-(4-Carbamimidoyl-benzyl)-N-[1-(S)-(1-(S)-carbamoyl-4-guanidino-butylcarbamoyl)-2-phenyl-ethyl]-N ,N',N'-trimethyl-malonamide trifluoroacetic acid salt | ok | solid phase |
| 113 | 2-(S)-[3-(4-Carbamimidoyl-phenyl)-2-dimethylcarbamoyl-propionyl]-1,2,3,4-tetrahydro-isoquinoline-3-carboxylic acid (1-(S)-carbamoyl-4-guanidino-butyl)-amide trifluoroacetic acid salt | ok | solid phase |
| 114 | 2-(4-Carbamimidoyl-benzyl)-N-[1-(S)-(1-(S)- | ok | solid |

-continued

| Expl. | Name | MS | Method |
|---|---|---|---|
|  | carbamoyl-4-guanidino-butylcarbamoyl)-pentyl]-N',N'-dimethyl-malonamide trifluoroacetic acid salt |  | phase |
| 115 | 2-(4-Carbamimidoyl-benzyl)-N-[1-(S)-(1-(S)-carbamoyl-4-guanidino-butylcarbamoyl)-2,2-dimethyl-propyl]-N'-methyl-malonamide trifluoroacetic acid salt | ok | solid phase |
| 116 | 2-(4-Carbamimidoyl-benzyl)-N-[1-(S)-[1-(S)-carbamoyl-4-guanidino-butylcarbamoyl)-2,2-dimethyl-propyl]-N',N'-dimethyl-malonamide trifluoroacetic acid salt | ok | solid phase |
| 117 | N-Allyl-2-(4-carbamimidoyl-benzyl)-N'-[1-(S)-(1-(S)-carbamoyl-4-guanidino-butylcarbamoyl)-2,2-dimethyl-propyl]-malonamide trifluoroacetic acid salt | ok | solid phase |
| 118 | 2-(4-Carbamimidoyl-benzyl)-N-[1-(S)-(1-(S)-carbamoyl-4-guanidino-butylcarbamoyl)-2,2-dimethyl-propyl]-N'-phenyl-malonamide trifluoroacetic acid salt | ok | solid phase |
| 119 | 2-(4-Carbamimidoyl-benzyl)-N-[(S)(1-(S)-carbamoyl-4-guanidino-butylcarbamoyl)-cyclohexyl-methyl]-N'-methyl-malonamide trifluoroacetic acid salt | ok | solid phase |
| 120 | N-Allyl-2-(4-carbamimidoyl-benzyl)-N'-[(S)-(1-(S)-carbamoyl-4-guanidino-butylcarbamoyl) cyclohexyl-methyl]-malonamide trifluoroacetic acid salt | ok | solid phase |
| 121 | 2-(4-Carbamimidoyl-benzyl)-N-[(S)-(1-(S)-carbamoyl-4-guanidino-butylcarbamoyl) cyclohexyl-methyl]-N'-phenyl-malonamide trifluoroacetic acid salt | ok | solid phase |
| 122 | 2-(4-Carbamimidoyl-benzyl)-N-[1-(S)-(1-(S)-carbamoyl-4-guanidino-butylcarbamoyl)-2-cyclohexyl-ethyl]-N'-methyl-malonamide trifluoroacetic acid salt | ok | solid phase |
| 123 | 2-(4-Carbamimidoyl-benzyl)-N-[1-(S)-(1-(S)-carbamoyl-4-guanidino-butylcarbamoyl)-2-cyclohexyl-ethyl]-N',N'-dimethyl-malonamide trifluoroacetic acid salt | ok | solid phase |
| 124 | N-Allyl-2-(4-carbamimidoyl-benzyl)-N'-[1-(S)-(1-(S)-carbamoyl-4-guanidino-butylcarbamoyl)-2-cyclohexyl-ethyl]-malonamide trifluoroacetic acid salt | ok | solid phase |
| 125 | 2-(4-Carbamimidoyl-benzyl)-N-[1-(S)-(1-(S)-carbamoyl-4-guanidino-butylcarbamoyl)-2-cyclohexyl-ethyl]-N'-phenyl-malonamide trifluoroacetic acid salt | ok | solid phase |
| 126 | 2-(4-Carbamimidoyl-benzyl)-N-[1-(S)-(1-(S)-carbamoyl-4-guanidino-butylcarbamoyl)-2-phenyl-ethyl]-N'-methyl-malonamide trifluoroacetic acid salt | ok | solid phase |
| 127 | N-Allyl-2-(4-carbamimidoyl-benzyl)-N'-[1-(S)-(1-(S)-carbamoyl-4-guanidino-butylcarbamoyl)-2-phenyl-ethyl]-malonamide trifluoroacetic acid salt | ok | solid phase |
| 128 | 2-(4-Carbamimidoyl-benzyl)-N-[1-(S)-(1-(S)-carbamoyl-4-guanidino-butylcarbamoyl)-2-phenyl-ethyl]-N'-phenyl-malonamide trifluoroacetic acid salt | ok | solid phase |
| 129 | N-Benzyl-N'-[(S)-(1-(S)-carbamoyl-4-guanidino-butylcarbamoyl)-cyclohexyl-methyl]-2-[4-(N-hydroxycarbamimidoyl)-benzyl]-malonamide trifluoroacetic acid salt, more polar diastereomer | ok | solid phase |
| 130 | N-Benzyl-N'-[(S)-(1-(S)-carbamoyl-4-guanidino-butylcarbamoyl)-cyclohexyl-methyl]-2-[4-(N-hydroxycarbamimidoyl)-benzyl]-malonamide trifluoroacetic acid salt, less polar diastereomer | ok | solid phase |
| 131 | 2-(S)-{2-(S)-[3-(4-Carbamimidoyl-phenyl)-2-dimethylcarbamoyl-propionylamino]-2-cyclohexyl-acetylamino}-5-guanidino-pentanoic acid ethyl ester hydrochloric acid salt | ok | class. Synth. |
| 132 | (S)-[2-Benzylcarbamoyl-3-(4-carbamimidoyl phenyl)-propionylamino]-cyclohexyl-acetic acid, less polar diastereomer | ok | class. Synth. |
| 133 | (S)-[2-Benzylcarbamoyl-3-(4-carbamimidoyl phenyl)-propionylamino]-cyclohexyl-acetic acid, more polar diastereomer | ok | class. Synth. |
| 134 | 2-{2-[3-(4-Carbamimidoyl-phenyl)-2-dimethylcarbamoyl-propionylamino]-2-cyclohexyl-acetylamino}-pentanedioic acid diamide hydrochloric acid salt | ok | class. Synth. |
| 135 | 2-(S)-{2-(S)-[2-Benzylcarbamoyl-3-(4-carbamimidoyl-phenyl)-propionylamino]-2-cyclohexyl-acetylamino}-5-guanidino-pentanoic acid ethyl ester trifluoroacetic acid salt | ok | class. Synth. |
| 136 | 2-(S)-{2-(S)-[2-Benzylcarbamoyl-3-(4-carbamimidoyl-phenyl)-propionylamino]-2-cyclohexyl-acetylamino}-5-guanidino-pentanoic acid ethyl trifluoroacetic acid salt, less polar diastereomer | ok | class. Synth. |
| 137 | 2-(4-Carbamimidoyl-benzyl)-N-[(S)-cyclohexyl-(4-guanidino-1-(S)-phenethylcarbamoyl-butylcarbamoyl)-methyl]-N',N'-dimethyl-malonamide hydrochloric acid salt | ok | class. Synth. |
| 138 | 2-(S)-{2-(S)-[3-(4-Carbamimidoyl-phenyl)-2-dimethylcarbamoyl-propionylamino]-2-cyclohexyl-acetylamino}-5-guanidino-pentanoic acid benzyl ester hydrochloric acid acetic acid salt | ok | class. Synth. |
| 139 | N-Benzyl-2-(4-carbamimidoyl-benzyl)-N'-{(S)-cyclohexyl-[(naphthalen-1-ylmethyl)-carbamoyl]-methyl}-malonamide trifluoroacetic acid salt | ok | class. Synth. |

Examples 140 and 141

N-Benzyl-2-(4-carbamimidoyl-benzyl)-N'-[(S)-(1-(S)-carbamoyl-4-guanidino-butylcarbamoyl)-cyclohexyl-methyl]-malonamide trifluoroacetic acid salt, less polar diastereomer and N-Benzyl-2-(4-carbamimidoyl-benzyl)-N'-[(S)-(1-(S)-carbamoyl-4-guanidino-butylcarbamoyl)-cyclohexyl-methyl]-malonamide trifluoroacetic acid salt, more polar diastereomer a) N-Benzyl-2-(R,S)-(4-cyano-benzyl)-malonamic acid A solution of benzylamine (58.6 g, 534 mmol), bis-(trimethylsilyl)-acetamide (71 ml, 90 mmol) and anhydrous dichloromethane (600 ml) was heated to reflux for 3 hours. The reaction mixture was allowed to cool to room temperature and 4-(R,S)-(2,2-dimethyl-4,6-dioxo-[1,3]dioxan-5-ylmethyl)-benzonitrile (15 g, 58 mmol) was added portionwize. The reaction mixture was refluxed for further 3 hours, allowed to cool to room temperature and poured into a cool mixture of 1000 ml 1 n hydrochloric acid and 500 ml ethylacetate, acidified to pH 4 with 2 n hydrochloric acid, and extracted with ethylacetate. The combined organic layers were washed with brine, dried and concentrated in vacuo. The precipitated crystals were suctioned off and dried to give 11.07 g (62%) of the desired product. mp: 152–153° C. (dc), MS: 309 (M+H).

b) [2-Benzylcarbamoyl-3-(R,S)-(4-cyano-phenyl)-propionylamino]-(S)-cyclohexyl-acetic acid methyl ester A solution of N-benzyl-2-(R,S)-(4-cyano-benzyl)-malonamic acid (10 g, 32.4 mmol), (S)-amino-cyclohexyl-acetic acid methyl ester (5.94 g, 34.7 mmol), diisopropyl-ethylamine (6.45 ml, 37.9 mmol), 3-hydroxy-3H-benzo[d][1,2,3]triazin-4-one (1.32 g, 8.1 mmol), and dimethylformamide (100 ml) was cooled to 10° C. A solution of dicyclohexyl-carbodiimide (7.83 g, 37.9 mmol) in toluene (10 ml) was added dropwise and the reaction mixture stood over night. The precipitated urea was suctioned off, the filtrate was evaporated in vacuo, dissolved in ethylacetate, washed with saturated sodium bicarbonate-solution and brine, dried, and evaporated in vacuo. Crystallization from n-heptane/isopropanol gave 9.91 g (66%) of the desired product. mp: 170–174° C., MS: 462 (M+H).

c) {2-Benzylcarbamoyl-3-(R,S)-[4-(N-hydroxycarbamimidoyl)-phenyl]-propionylamino}-(S)-cyclohexyl-acetic acid methyl ester A suspension of [2-benzylcarbamoyl-3-(R,S)-(4-cyano-phenyl)-propionylamino]-(S)-cyclohexyl-acetic acid methyl ester (9.0 g, 19.5 mmol) and hydroxylamine (3.22 g, 97.5 mmol) in ethanol (180 ml) was heated to reflux for 4 hours. The reaction mixture was cooled to room temperature, evaporated in vacuo, dissolved in ethanol and poured in ice-water. The precipitate was collected by suction and dried at 50° C. in vacuo to give 7.9 g (82%) of the desired product. mp: 101–104° C., MS: 495 (M+H).

d) [2-Benzylcarbamoyl-3-(R,S)-(4-carbamimidoyl-phenyl)-propionylamino]-(S)-cyclohexyl-acetic acid methyl ester {2-Benzylcarbamoyl-3-(R,S)-[4-(N-hydroxycarbamimidoyl)-phenyl]-propionylamino}-(S)-cyclohexyl-acetic acid methyl ester (7.6 g, 15.4 mmol) was hydrogenated in acetic acid with palladium/charcoal to give the desired product which was used without further purification in the next step. mp: 101–104° C., MS: 479 (M+H).

e) [2-Benzylcarbamoyl-3-(R,S)-(4-carbamimidoyl-phenyl)-propionylamino]-(S)-cyclohexyl-acetic acid hydrochloride The above [2-benzylcarbamoyl-3-(R,S)-(4-carbamimidoyl-phenyl)-propionylamino]-(S)-cyclohexyl-acetic acid methyl ester was suspended in water/concentrated hydrochloric acid (1/1,200 ml) and stirred at room temperature. After 8 days acetonitrile (100 ml) was added and stirred for further 2 days. The reaction mixture was filtered and poured in ice-water.

The precipitate was collected by fractionized crystallization:

Fr.1: 3.36 g (52%, diast. mixture:6.7% more polar, 78.0% less polar)

Fr.2: 857 mg (13%, diast. mixture: 55.3% more polar, 31.9% less polar), oil

Fr.3: 461 mg (7%, diast. mixture: 3.8% more polar, 93.5% less polar), mp: 166° C. (subl.)

Fr.4: 455 mg (7%, 96.7% less polar diastereomer), oil

HPLC: polar diastereomer: 15.62 min, non-polar diastereomer: 16.21 min.

HPLC-conditions: Nucleosil 250/4, 7 $\mu$M, 1 ml/min, gradient: 100% ($H_2O$+0.1% trifluoroacetic acid) to 100% acetonitrile in 30 min, 100% acetonitrile 5 min, $\lambda$=254 nm.

MS of all fractions show: 465 (M+H). It was tried to purify Fr.1 by flash chromatography on silica gel (dichloromethane/methanol/ glacial acetic acid =9/1/0.5), but isomerization of the malonic chiral center took place to give the acetic acid salt of the title compound.

f) N-Benzyl-2-(R)-(4-carbamimidoyl-benzyl)-N'-[(1-carbamoyl-4-guanidino-butylcarbamoyl)-cyclohexyl-methyl]-malonamide trifluoroacetic acid salt and N-Benzyl-2-(S)-(4-carbamimidoyl-benzyl)-N'-[(1-carbamoyl-4-guanidino-butylcarbamoyl)-cyclohexyl-methyl]-malonamide trifluoroacetic acid salt A solution of [2-benzylcarbamoyl-3-(R,S)-(4-carbamimidoyl-phenyl)-propionylamino]-(S)-cyclohexyl-acetic acid acetate (103 mg, 0.20 mmol), benzotriazol-1-ol hydrate (32 mg, 0.24 mmol), 2-(S)-amino-5-guanidino-pentanoic acid amide in dimethylformamide (4 ml) was stirred for 30 min and cooled to 0 to −5° C. A solution of 1,3-dicyclohexyl urea (49 mg, 0.24 mmol) was added and the reaction mixture was stirred for 24 hours at 0° C. The solvent was evaporated and the residue was purified by preparative HPLC to give 4.5 mg (3%) of F1 (more polar diastereomer) and 7.8 mg (5%) of F2 (less polar diastereomer).

HPLC-conditions: Nucleosil 250/21 mm, 7 $\mu$M, 15 ml/min, 68% $H_2O$+0.1% trifluoroacetic acid, 32% acetonitrile.

F1: mp.: 150–154° C., MS m/z: 620.5 ((M+H)$^+$, 9%), 310.9 ((M+2H)$^{2+}$, 100%).

F2: mp.: 102–106° C., MS m/z: 620.5 ((M+H)$^+$, 5%), 310.9 ((M+2H)$^{2+}$, 34%), 150.0 (100%).

The following compounds were prepared using the procedures described above:

| Expl. | Name | MS | Method |
|---|---|---|---|
| 142 | 2-(4-Carbamimidoyl-benzyl)-N-{(S)-[2-(3-carbamimidoyl-phenyl)-1-carbamoyl-ethyl-carbamoyl]-cyclohexyl-methyl} N',N'-dimethyl-malonamide trifluoroacetic acid salt, more polar diastereomer | ok | class. Synth. |
| 143 | 2-(4-Carbamimidoyl-benzyl)-N-{(S)-[2-(3-carbamimidoyl-phenyl)-1-carbamoyl-ethylcarbamoyl]-cyclohexyl-methyl}-N',N'-dimethyl-malonamide trifluoroacetic acid salt, less polar diastereomer | ok | class. Synth. |
| 144 | N-Benzyl-2-(4-carbamimidoyl-benzyl)-N'-[(S)-(1-(S)-carbamoyl-4-guanidino-butylcarbamoyl)-cyclohexyl-methyl]-N-methyl-malonamide trifluoroacetic acid salt | ok | class. Synth. |
| 145 | 2-(S)-{2-(S)-[2-(Benzyl-methyl-carbamoyl)-3-(4-carbamimidoyl-phenyl)-propionylamino]-2-cyclohexyl-acetylamino}-5-guanidino-pentanoic acid hydrochloric acid salt | ok | class. Synth. |
| 146 | 2-{2-(S)-[2-(Benzyl-methyl-carbamoyl)-3-(4-carbamimidoyl-phenyl)-propionylamino]-2-cyclohexyl-acetylamino}-3-naphthalen-1-yl-propionic acid ethyl ester trifluoroacetic acid salt, less polar diastereomer | ok | class. Synth. |
| 147 | 2{2-(S)-[2-(Benzyl-methyl-carbamoyl)-3-(4-carbamimidoyl-phenyl)-propionylamino]-2-cyclohexyl-acetylamino}-3-naphthalen-1-yl-propionic acid ethyl ester trifluoroacetic acid salt, more polar diastereomer | ok | class. Synth. |
| 148 | 2-(S)-{2-[2-(Benzyl-methyl-carbamoyl)-3-(4-carbamimidoyl-phenyl)-propionylamino]-2-cyclohexyl-acetylamino}-5-guanidino-pentanoic acid methyl ester trifluoroacetic acid salt, least polar diastereomer | ok | class. Synth. |
| 149 | 2-(S)-{2-[2-(Benzyl-methyl-carbamoyl)-3-(4-carbamimidoyl-phenyl)-propionylamino]-2-cyclohexyl-acetylamino}-5-guanidino-pentanoic acid methyl ester trifluoroacetic acid salt, less polar diastereomer | ok | class. Synth. |
| 150 | 2-(S)-{2-[2-(Benzyl-methyl-carbamoyl)-3-(4-carbamimidoyl-phenyl)-propionylamino]-2-cyclohexyl-acetylamino}-5-guanidino-pentanoic acid methyl ester trifluoroacetic acid salt, more polar diastereomer | ok | class. Synth. |
| 151 | 2-(S)-{2-[2-(Benzyl-methyl-carbamoyl)-3-(4-carbamimidoyl-phenyl)-propionylamino]-2-cyclohexyl-acetylamino}-5-guanidino-pentanoic acid methyl ester trifluoroacetic acid salt, most polar diastereomer | ok | class. Synth. |
| 152 | N-Benzyl-N'-{[1-(S)-(benzyl-methyl-carbamoyl)-4-guanidino-butylcarbamoyl]-cyclohexyl-methyl}-2-(4-carbamimidoyl-benzyl)-N-methyl- | ok | class. Synth. |

| Expl. | Name | MS | Method |
|---|---|---|---|
| | malonamide trifluoroacetic acid salt, most polar diastereomer | | |
| 153 | N-Benzyl-N'-{[1-(S)-(benzyl-methyl-carbamoyl)-4-guanidino-butylcarbamoyl]-cyclohexyl-methyl}-2-(4-carbamimidoyl-benzyl)-N-methyl-malonamide trifluoroacetic acid salt, more polar diastereomer | ok | class. Synth. |
| 154 | N-Benzyl-N'-{[1-(S)-(benzyl-methyl-carbamoyl)-4-guanidino-butylcarbamoyl]-cyclohexyl-methyl}-2-(4-carbamimidoyl-benzyl)-N-methyl-malonamide trifluoroacetic acid salt, less polar diastereomer | ok | class. Synth. |
| 155 | N-Benzyl-2-(4-carbamimidoyl-benzyl)-N'-[cyclohexyl-(1-(S)-dimethylcarbamoyl-4-guanidino-butylcarbamoyl)-methyl]-N-methyl-malonamide trifluoroacetic acid salt | ok | class. Synth. |
| 156 | (S)-[2-(4-Carbamimidoyl-benzylcarbamoyl)-3-(4-carbamidino-phenyl)-propionylamino]-cyclohexyl-acetic acid methyl ester trifluoroacetic acid salt | ok | class. Synth. |
| 157 | (S)-[2-(4-Carbamimidoyl-benzylcarbamoyl)-3-(4-carbamidino-phenyl)-propionylamino]-cyclohexyl-acetic acid trifluoroacetic acid salt | ok | class. Synth. |

Abbreviations Used aPTT activated partial thromboplastin time
ATS Antistasin
AV Arteriovenous
BAPNA benzoyl-L-Arg-p-nitroanilide
Boc tert butoxycarbonyl
° C. degrees Celsius
Cal Calculated
$CDCl_3$ deutero chloroform
Class. Synth. classical synthesis
Cm Centimeter
Dc Decomposition
DCCI Dicyclohexylcarbodiimide
DCRu Dichlorotetrakis (triphenylphosphine) ruthenium (II)
DIC disseminated intravascular coagulation
DICI Diisopropylcarbodiimide
DMSO Dimethylsulfoxide
DVT deep vein thrombosis
eq. Equivalent
ESMS electro spray mass spectra
expl Example
FAB fast atom bombardment
Fmoc 9-fluorenylmethoxycarbonyl
FT-IR Fourier transformed infrared
G Gram
H Hour
HATU N-[(dimethylamino)-1H-1,2,3-triazolo[4,5-b]pyridin-1yl-methylene]-N-methylmethanaminium hexafluorophosphate N-oxide
HPLC high pressure liquid chromatography
HPLC/ESMS high pressure liquid chromatography/electro spray mass spectra
Id Intraduodenal
Iv Intravenous
Kg Kilogram
Km Michaelis-Menten-constant
LMWH low molecular weight heparin
Mg Milligram
MHz Megahertz
min Minutes
Ml Milliliter
mM Millimolar
mmol Millimol
MS mass spectra
Mp. melting point
μl Microliter
μm Micrometer
μM Micromolar
Nm Nanometer
NM Nanomolar
NMR nuclear magnetic resonance
PE Polyethylene
PEG Polyethyleneglycol
PG protecting group
PPP platelet poor blood
PT prothrombin time
sec Seconds
TAP tick anticoagulant peptide
TBS-BSA tris buffered saline bovine serum albumin
TBS-PEG tris buffered saline polyethylene glycol
TF tissue factor
TFPI tissue factor pathway inhibitor
TOTU O-((cyano-(ethoxycarbonyl)-methylene)amino)-N,N,N',N'-tetra-methyluronium tetrafluoroborate
TPCK Tosyl phenyl chloromethyl ketone
TRIS-Cl bis(2-Hydroxyethyl)iminotris(hydroxymethyl)methane 2-bis(2-Hydroxyethyl)amino-2-(hydroxymethyl)-1,3-propanediol, chloride salt
UV Ultra violet

We claim:

1. Compounds of the formula I,

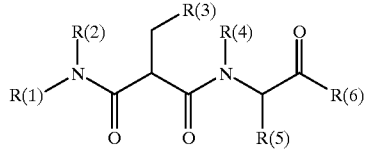
(I)

wherein
R(1) is hydrogen, $(C_1–C_6)$-alkyl, $(C_2–C_6)$-alkenyl, $(C_6–C_{10})$-aryl, $(C_6–C_{10})$-aryl-$(C_1–C_4)$-alkyl, where aryl in aryl-alkyl is unsubstituted or substituted by R(17);
R(2) is hydrogen or $(C_1–C_4)$-alkyl;
R(3) is $(C_6–C_{10})$-aryl which is substituted by R(7);
R(4) is hydrogen or $(C_1–C_4)$-alkyl;
R(5) is $(C_1–C_6)$-alkyl, $(C_3–C_7)$-cycloalkyl, $(C_3–C_7)$-cycloalkyl-$(C_1–C_4)$-alkyl, $(C_6–C_{10})$-aryl, or $(C_6–C_{10})$-aryl-$(C_1–C_4)$-alkyl, where aryl in aryl-alkyl is unsubstituted or substituted by a residue R(20), and where alkyl is unsubstituted or substituted by a residue R(21); or
R(4) and R(5) together form a residue of the formula II

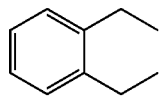
(II)

R(6) is NR(8)R(9) or OR(22);
R(7) is R(17) or R(20);
R(8) is hydrogen; $(C_1–C_4)$-alkyl, where alkyl is unsubstituted or substituted by a residue R(20); heteroaryl- ($C_1$–$C_4$)-alkyl; or ($C_6$–$C_{10}$)-aryl-($C_1$–$C_4$)-alkyl, where aryl is unsubstituted or substituted by a residue R(17);

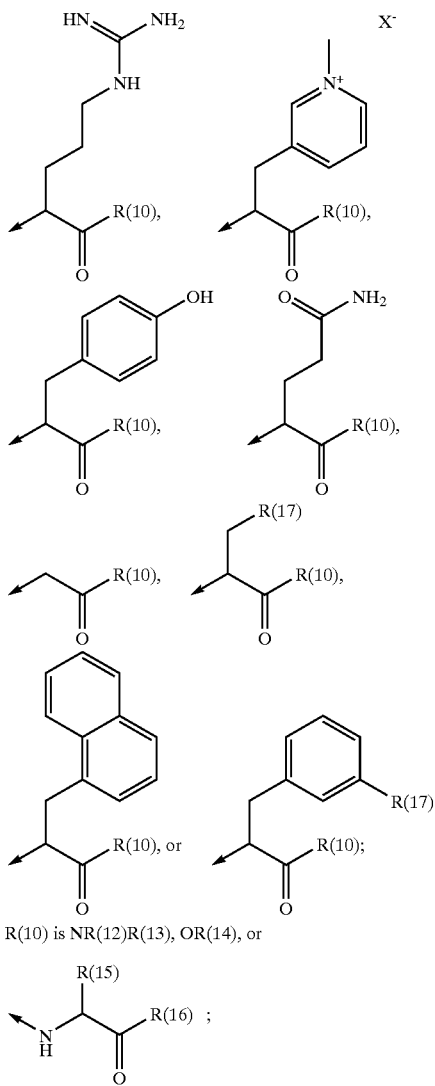

R(10) is NR(12)R(13), OR(14), or

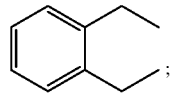

R(12) is hydrogen or ($C_1$–$C_4$)-alkyl;
R(13) is hydrogen, ($C_6$–$C_{10}$)-aryl-($C_1$–$C_4$)-alkyl, or ($C_1$–$C_4$)-alkyl;
R(14) is hydrogen, ($C_1$–$C_4$)-alkyl, ($C_2$–$C_4$)-alkenyl or ($C_6$–$C_{10}$)-aryl-($C_1$–$C_4$)-alkyl;
R(15) is ($C_3$–$C7$)-cycloalkyl-($C_1$–$C_4$)-alkyl;
R(16) is R(20);
R(17) is —C(=N—R(18))—N(R(19))$_2$;
R(18) is hydrogen, hydroxy, or an amino protective group;
R(19) is hydrogen, ($C_1$–$C_4$)-alkyl, ($C_6$–$C_{10}$)-aryl-($C_1$–$C_4$)-alkoxycarbonyl, or an amino protective group;
R(20) is N(R(19))$_2$;
R(21) is hydroxy, ($C_6$–$C_{10}$)-aryl-($C_1$–$C_4$)-alkoxy, ($C_6$–$C_{10}$)-aryl-($C_1$–$C_4$)-alkoxycarbonylamino, carboxyl, or R(20);
R(22) is hydrogen or ($C_1$–$C_4$)-alkyl;

X⁻ is a physiologically acceptable anion;

in all stereoisomeric forms and physiologically acceptable salts thereof.

2. Compounds of the formula I as claimed in claim 1, wherein:

R(1) is hydrogen, ($C_1$–$C_4$)-alkyl, allyl, phenyl, benzyl, or 4-carbamimidoyl-benzyl;

R(2) is hydrogen or ($C_1$–$C_4$)-alkyl;

R(3) is phenyl or naphthyl, which are substituted by R(7);

R(4) is hydrogen or methyl;

R(5) is n-butyl, sec-butyl, tert-butyl, cyclohexyl, cyclohexylmethyl, phenyl, benzyl, 2-phenyl-ethyl, 1-naphthylmethyl, 2-naphthylmethyl, aminobenzyl, hydroxymethyl, benzyloxymethyl, carboxymethyl, 2-carboxy-ethyl, 3-amino-propyl, or 4-(benzyloxycarbonylamino)-butyl; or R(4) and R(5) together form a residue of the formula II (II)

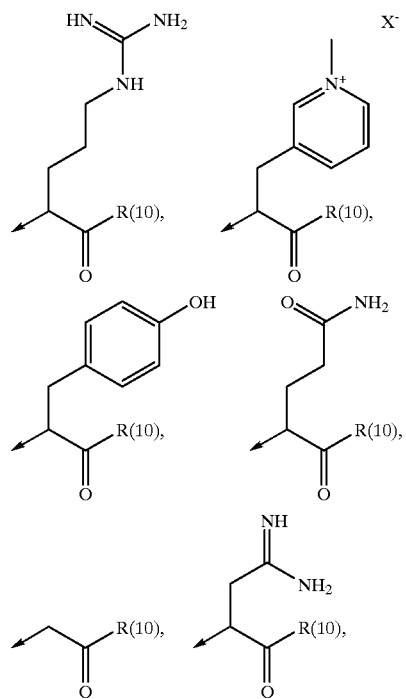

R(6) is NR(8)R(9), OH, or OCH$_3$;

R(7) is amidino, hydroxyamidino, amino, or dimethylamino;

R(8) is hydrogen, pyridylmethyl, 3-carbamimidoylbenzyl, or 4-amino-butyl;

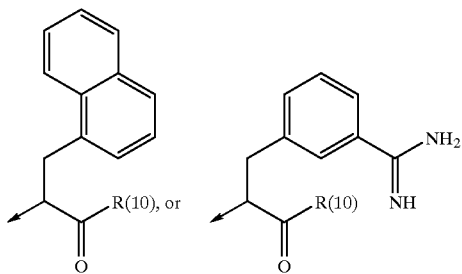

R(10) is NR(12)R(13), OR(14), or

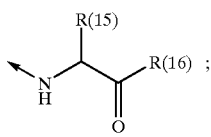

R(12) is hydrogen or methyl;

R(13) is hydrogen, phenyl-($C_1$–$C_2$)-alkyl, or methyl;

R(14) is hydrogen, ($C_1$–$C_2$)-alkyl, benzyl, or allyl;

R(15) is cyclohexylmethyl;

R(16) is amino;

X⁻ is a physiologically acceptable anion;

and all stereoisomeric forms and physiologically acceptable salts thereof.

3. Compounds of the formula I as claimed in claim 1, wherein

R(1) is hydrogen, ($C_1$–$C_3$)-alkyl, allyl, phenyl, benzyl, or 4-carbamimidoyl-benzyl;

R(2) is hydrogen or ($C_1$–$C_3$)-alkyl;

R(3) is phenyl or 2-naphthyl which is substituted by R(7);

R(4) is hydrogen or methyl;

R(5) is n-butyl, sec-butyl, tert-butyl, cyclohexyl, cyclohexylmethyl, phenyl, benzyl, 2-phenyl-ethyl, 1-naphthylmethyl, 2-naphthylmethyl, 4-aminobenzyl, hydroxymethyl, benzyloxymethyl, carboxymethyl, 2-carboxy-ethyl, 3-amino-propyl, or 4-(benzyloxycarbonylamino)-butyl; or R(4) and R(5) together form a residue of the formula II (II)

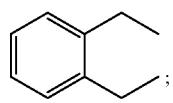

R(6) is NR(8)R(9), OH, or $OCH_3$;

R(7) is amidino, hydroxyamidino, or dimethylamino;

R(8) is hydrogen, pyridylmethyl, 3-carbamimidoylbenzyl, or 4-amino-butyl;

R(9) is naphthylmethyl,

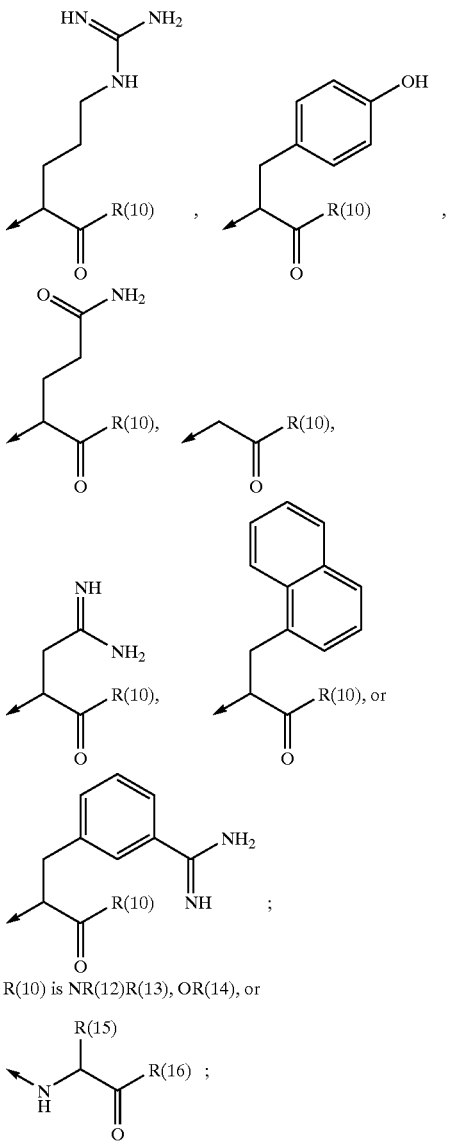

R(10) is NR(12)R(13), OR(14), or

R(12) is hydrogen or methyl;
R(13) is hydrogen, phenyl-($C_1$–$C_2$)-alkyl, or methyl;
R(14) is hydrogen, ($C_1$–$C_2$)-alkyl, benzyl, or allyl;
R(15) is cyclohexylmethyl;
R(16) is amino;
and all stereoisomeric forms and physiologically acceptable salts thereof.

4. Compounds of the formula I as claimed in claim 1, wherein

R(1) is hydrogen, ($C_1$–$C_3$)-alkyl, allyl, phenyl, benzyl, or 4-carbamimidoyl-benzyl;

R(2) is hydrogen or ($C_1$–$C_3$)-alkyl;

R(3) is phenyl or naphthyl, which are substituted by R(7);

R(4) is hydrogen or methyl;

R(5) is n-butyl, sec-butyl, tert-butyl, cyclohexyl, cyclohexylmethyl, phenyl, benzyl, 2-phenyl-ethyl, 1-naphthylmethyl, 2-naphthylmethyl, aminobenzyl, hydroxymethyl, benzyloxymethyl, carboxymethyl, 2-carboxy-ethyl, 3-amino-propyl, or 4-(benzyloxycarbonylamino)-butyl; or R(4) and R(5) together form a residue of the formula II

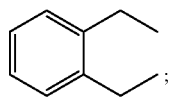
(II)

R(6) is NR(8)R(9), OH, or OCH$_3$;
R(7) is amidino, hydroxyamidino, or dimethylamino;
R(8) is hydrogen, pyridylmethyl, 3-carbamimidoylbenzyl, or 4-amino-butyl;
R(9) is naphthylmethyl,

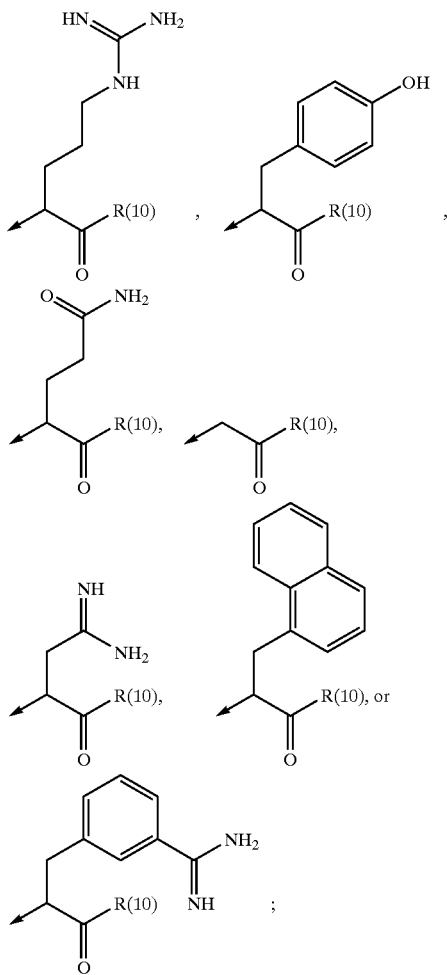

R(10) is NR(12)R(13), or OR(14);
R(12) is hydrogen or methyl;
R(13) is hydrogen, phenyl-(C$_1$–C$_2$)-alkyl, or methyl;
R(14) is hydrogen, (C$_1$–C$_2$)-alkyl, benzyl, or allyl;
and all stereoisomeric forms and physiologically acceptable salts thereof.

5. Compounds of the formula I as claimed in claim 1, wherein
R(1) is methyl, allyl, phenyl, or benzyl;
R(2) is hydrogen or methyl;
R(3) is phenyl which is substituted by R(7);
R(4) is hydrogen;
R(5) is butyl, cyclohexyl, cyclohexylmethyl, phenyl, benzyl, 2-phenyl-ethyl, 1-naphthylmethyl, 2-naphthylmethyl, aminobenzyl, benzyloxymethyl, carboxymethyl, or 2-carboxy-ethyl;
R(6) is NR(8)R(9);
R(7) is amidino or hydroxyamidino;
R(8) is hydrogen;

R(9) is

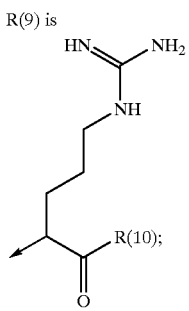

R(10) is NR(12)R(13) or OR(14);
R(12) is hydrogen or methyl;
R(13) is hydrogen or phenyl-(C$_1$–C$_2$)-alkyl;
R(14) is hydrogen, (C$_1$–C$_2$)-alkyl, or allyl;
an all their stereoisomeric forms and physiologically acceptable salts thereof.

6. Compounds of the formula I as claimed in claim 5, wherein
R(1) is methyl or benzyl.

7. Compounds of the formula I as claimed in claim 1, selected from the group consisting of:
2-(4-Carbamimidoyl-benzyl)-N-[(1-carbamoyl-4-guanidino-butylcarbamoyl)-cyclohexyl-methyl]-N',N'-dimethyl-malonamide trifluoroacetic acid salt, less polar diastereomer, 2-(S)-{2-(S)-[2-(Benzyl-methyl-carbamoyl)-3-(4-carbamimidoyl-phenyl)-propionylamino]-2-cyclohexyl-acetylamino}-5-guanidino-pentanoic acid allyl ester trifluoroacetic acid salt, less polar diastereomer, N-Benzyl-2-(4-carbamimidoyl-benzyl)-N'-[(S)-(1-(S)-carbamoyl-4-guanidino-butylcarbamoyl)-cyclohexyl-methyl]-malonamide trifluoroacetic acid salt, more polar diastereomer, N-Benzyl-2-(4-carbamimidoyl-benzyl)-N'-[(S)-(1-(S)-carbamoyl-4-guanidino-butylcarbamoyl)-cyclohexyl-methyl]-malonamide trifluoroacetic acid salt, less polar diastereomer, N-Benzyl-N'-[(S)-(1-(S)-carbamoyl-4-guanidino-butylcarbamoyl)-cyclohexyl-methyl]-2-[4-(N-hydroxycarbamimidoyl)-benzyl]-malonamide trifluoroacetic acid salt, N-[2-(4-Amino-phenyl)-1-(S)-(1-(S)-carbamoyl-4-guanidino-butylcarbamoyl)-ethyl]-2-(4-carbamimidoyl-benzyl)-N',N'-dimethyl-malonamide trifluoroacetic acid salt, 2-(4-Carbamimidoyl-benzyl)-N-[1-(S)-(1-(S)-carbamoyl-4-guanidino-butylcarbamoyl)-pentyl]-N'-methyl-malonamide trifluoroacetic acid salt, 4-(S)-[3-(4-Carbamimidoyl-phenyl)-2-dimethylcarbamoyl-propionylamino]-4-(1-(S)-carbamoyl-4-guanidino-butylcarbamoyl)-butyric acid, 2-(4-Carbamimidoyl-benzyl)-N-[1-(S)-(1-(S)-carbamoyl-4-guanidino-butylcarbamoyl)-2-naphthalen-2-yl-ethyl]-N',N'-dimethyl-malonamide trifluoroacetic acid salt, 2-(4-Carbamimidoyl-benzyl)-N-[1-(S)-(1-(S)-carbamoyl-4-guanidino-butylcarbamoyl)-3-phenyl-propyl]-N',N'-dimethyl-malonamide trifluoroacetic acid salt, 3-(S)-[3-(4-Carbamimidoyl-phenyl)-2-dimethylcarbamoyl-propionylamino]-N-(1-(S)-carbamoyl-4-guanidino-butyl)-succinamic acid trifluoroacetic acid salt, 2-(4-Carbamimidoyl-benzyl)-N-[(S)-(1-(S)-carbamoyl-4-guanidino-butylcarbamoyl)-phenyl-methyl]-N'-methyl-malonamide trifluoroacetic acid salt, 2-(4-Carbamimidoyl-benzyl)-N-[(S)(1-(S)-carbamoyl-4-guanidino-butylcarbamoyl)-phenyl-methyl]-N',N'-dimethyl-malonamide trifluoroacetic acid salt, N-[2-Benzyloxy-1-(S)-(1-(S)-carbamoyl-4-guanidino-butylcarbamoyl)-ethyl]-2-(4-carbamimidoyl-benzyl)-N',N'-dimethyl-malonamide trifluoroacetic acid salt, 2-(4-Carbamimidoyl-benzyl)-N-[1-(S)-(1-(S)-carbamoyl-4-guanidino-butylcarbamoyl)-pentyl]-N',N'-dimethyl-malonamide trifluoroacetic acid salt, less polar diastereomer, 2-(S)-{2-(S)-[3-(4-Carbamimidoyl-phenyl)-2-dimethylcarbamoyl-propionylamino]-hexanoylamino}-5-guanidino-pentanoic acid trifluoroacetic acid salt, 2-(S)-{2-(S)-[3-(4-Carbamimidoyl-phenyl)-2-dimethylcarbamoyl-propionylamino]-2-cyclohexyl-acetylamino}-5-guanidino-pentanoic acid; compound with trifluoro-acetic acid trifluoroacetic acid salt, 2-(S)-{12-(S)-[3-(4-Carbamimidoyl-phenyl)-2-methylcarbamoyl-propionylamino]-2-cyclohexyl-acetylamino}-5-guanidino-pentanoic acid trifluoroacetic acid salt, 2-(S)-{2-(S)-[2-Benzylcarbamoyl-3-(4-carbamimidoyl-phenyl)-propionylamino]-2-cyclohexyl-acetylamino}-5-guanidino-pentanoic acid trifluoroacetic acid salt, 2-(S)-{2-(S)-[3-(4-Carbamimidoyl-phenyl)-2-dimethylcarbamoyl-propionylamino]-3-cyclohexyl-propionylamino}-5-guanidino-pentanoic acid trifluoroacetic acid salt, 2-(4-Carbamimidoyl-benzyl)-N-[1-(S)-(1-(S)-carbamoyl-4-guanidino-butylcarbamoyl)-2-phenyl-ethyl]-N',N'-dimethyl-malonamide trifluoroacetic acid salt, less polar diastereomer, 2-(4-Carbamimidoyl-benzyl)-N-[1-(S)-(1-(S)-carbamoyl-4-guanidino-butylcarbamoyl)-2-naphthalen-1-yl-ethyl]-N',N'-dimethyl-malonamide trifluoroacetic acid salt, 2-(4-Carbamimidoyl-benzyl)-N-[1-(S)-(1-(S)-carbamoyl-4-guanidino-butylcarbamoyl)-pentyl]-N',N'-dimethyl-malonamide trifluoroacetic acid salt, 2-(4-Carbamimidoyl-benzyl)-N-[(S)-(1-(S)-carbamoyl4-guanidino-butylcarbamoyl)-cyclohexyl-methyl]-N'-methyl-malonamide trifluoroacetic acid salt, 2-(4-Carbamimidoyl-benzyl)-N-[1-(S)-(1-(S)-carbamoyl-4-guanidino-butylcarbamoyl)-2-cyclohexyl-ethyl]-N',N'-dimethyl-malonamide trifluoroacetic acid salt, N-Benzyl-N'-[(S)-(1-(S)-carbamoyl-4-guanidino-butylcarbamoyl)-cyclohexyl-methyl]-2-[4-(N-hydroxycarbamimidoyl)-benzyl]-malonamide trifluoroacetic acid salt, less polar diastereomer, 2-(S)-{2-(S)-[3-(4-Carbamimidoyl-phenyl)-2-dimethylcarbamoyl-propionylamino]-2-cyclohexyl-acetylaminol-5-guanidino-pentanoic acid ethyl ester hydrochloric acid salt, 2-(S)-{2-(S)-[2-Benzylcarbamoyl-3-(4-carbamimidoyl-phenyl)-propionylamino]-2-cyclohexyl-acetylaminol-5-guanidino-pentanoic acid ethyl trifluoroacetic acid salt, less polar diastereomer, 2-(4-Carbamimidoyl-benzyl)-N-[(S)-cyclohexyl-(4-guanidino-1-(S)-phenethylcarbamoyl-butylcarbamoyl)-methyl]-N',N'-dimethyl-malonamide hydrochloric acid salt, N-Benzyl-2-(4-carbamimidoyl-benzyl)-N'-[(S)-(1-(S)-carbamoyl-4-guanidino-butylcarbamoyl)-cyclohexyl-methyl]-malonamide trifluoroacetic acid salt, more polar diastereomer, N-Benzyl-2-(4-carbamimidoyl-benzyl)-N'-[(S)-(1-(S)-carbamoyl-4-guanidino-butylcarbamoyl)-cyclohexyl-methyl]-malonamide trifluoroacetic acid salt, less polar diastereomer, N-Benzyl-2-(4-carbamimidoyl-benzyl)-N'-[(S)-(1-(S)-carbamoyl-4-guanidino-butylcarbamoyl)-cyclohexyl-methyl]-N-methyl-malonamide trifluoroacetic acid salt, 2-(S)-{2-(S)-[2-(Benzyl-methyl-carbamoyl)-3-(4-carbamimidoyl-phenyl)-propionylamino]-2-cyclohexyl-acetylamino}-5-guanidino-pentanoic acid hydrochloric acid salt, 2-(S)-{2-[2-(Benzyl-methyl-carbamoyl)-3-(4-carbamimidoyl-phenyl)-propionylamino]-2-cyclohexyl-acetylamino}-5-guanidino-pentanoic acid methyl ester trifluoroacetic acid salt, least polar diastereomer, N-Benzyl-N'-{[1-(S)-(benzyl-methyl-carbamoyl)-4-guanidino-butylcarbamoyl]-cyclohexyl-methyl}-2-(4-carbamimidoyl-benzyl)-N-methyl-malonamide trifluoroacetic acid salt, less polar diastereomer, or their physiologically acceptable salts.

8. Compounds of the formula I,

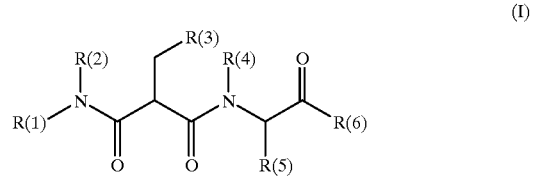

wherein

R(1) is hydrogen, $(C_1-C_6)$-alkyl, $(C_2-C_6)$-alkenyl, $(C_6-C_{10})$-aryl, or $(C_6-C_{10})$-aryl-$(C_1-C_4)$-alkyl, where aryl in aryl-alkyl is unsubstituted or substituted by R(17);

R(2) is hydrogen or $(C_1-C_4)$-alkyl;

R(3) is $(C_6-C_{10})$-aryl which is substituted by R(7);

R(4) is hydrogen or $(C_1-C_4)$-alkyl;

R(5) is $(C_1-C_6)$-alkyl, $(C_3-C7)$-cycloalkyl, $(C_3-C7)$-cycloalkyl-$(C_1-C_4)$-alkyl, $(C_6-C_{10})$-aryl, or $(C_6-C_{10})$-aryl-$(C_1-C_4)$-alkyl, where aryl in aryl-alkyl is unsubstituted or substituted by a residue R(20), and where alkyl is unsubstituted or substituted by a residue R(21); or R(4) and R(5) together form a residue of the formula II

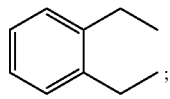
(II)

R(6) is NR(8)R(9) or OR(22);

R(7) is R(17) or R(20);

R(8) is hydrogen; $(C_1-C_4)$-alkyl, where alkyl is unsubstituted or substituted by a residue R(20); heteroaryl-$(C_1-C_4)$-alkyl; or $(C_6-C_{10})$-aryl-$(C_1-C_4)$-alkyl, where aryl is unsubstituted or substituted by a residue R(17);

R(9) is

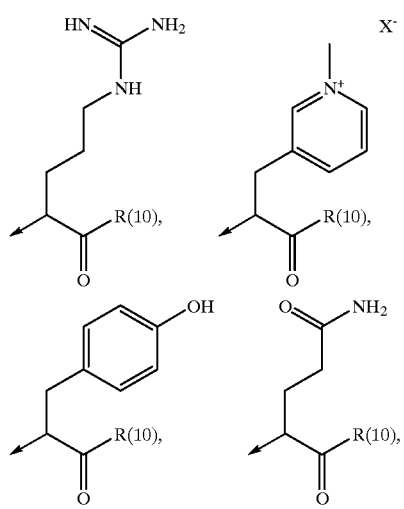

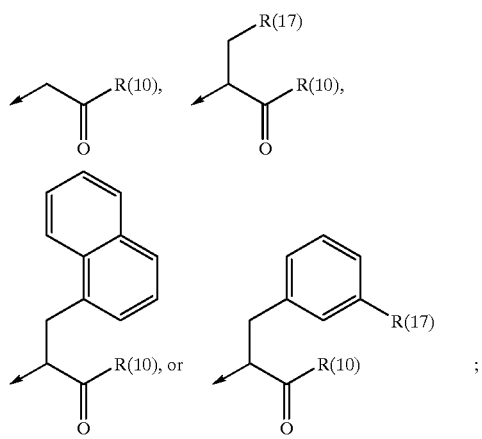

R(10) is

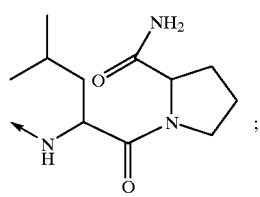

R(17) is —C(=N—R(18))—N(R(19))$_2$;

R(18) is hydrogen, hydroxy, or an amino protective group;

R(19) is hydrogen, $(C_1-C_4)$-alkyl, $(C_6-C_{10})$-aryl-$(C_1-C_4)$-alkoxycarbonyl, or an amino protective group;

R(20) is N(R(19))$_2$;

R(21) is hydroxy, $(C_6-C_{10})$-aryl-$(C_1-C_4)$-alkoxy, $(C_6-C_{10})$-aryl-$(C_1-C_4)$-alkoxycarbonylamino, carboxyl, or R(20);

R(22) is hydrogen or $(C_1-C_4)$-alkyl;

X$^-$ is a physiologically acceptable anion;

an all stereoisomeric forms and physiologically acceptable salts thereof.

9. Compounds of the formula I as claimed in claim 8, wherein

R(1) is hydrogen, $(C_1-C_4)$-alkyl, allyl, phenyl, benzyl, or 4-carbamimidoyl-benzyl;

R(2) is hydrogen or $(C_1-C_4)$-alkyl;

R(3) is phenyl or 2-naphthyl which are substituted by R(7);

R(4) is hydrogen or methyl;

R(5) is n-butyl, sec-butyl, tert-butyl, cyclohexyl, cyclohexylmethyl, phenyl, benzyl, 2-phenyl-ethyl, 1-naphthylmethyl, 2-naphthylmethyl, aminobenzyl, hydroxymethyl, benzyloxymethyl, carboxymethyl, 2-carboxy-ethyl, 3-amino-propyl, or 4-(benzyloxycarbonylamino)-butyl; or R(4) and R(5) together form a residue of the formula II

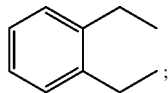
(II)

R(6) is NR(8)R(9), OH, or OCH$_3$;

R(7) is amidino, hydroxyamidino, amino, or dimethylamino;

R(8) is hydrogen, pyridylmethyl, 3-carbamimidoylbenzyl, or 4-amino-butyl;

R(9) is

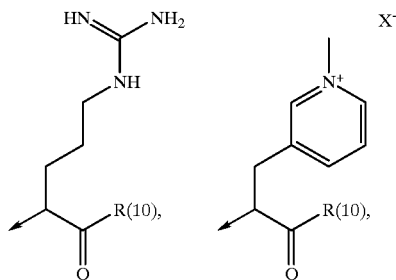

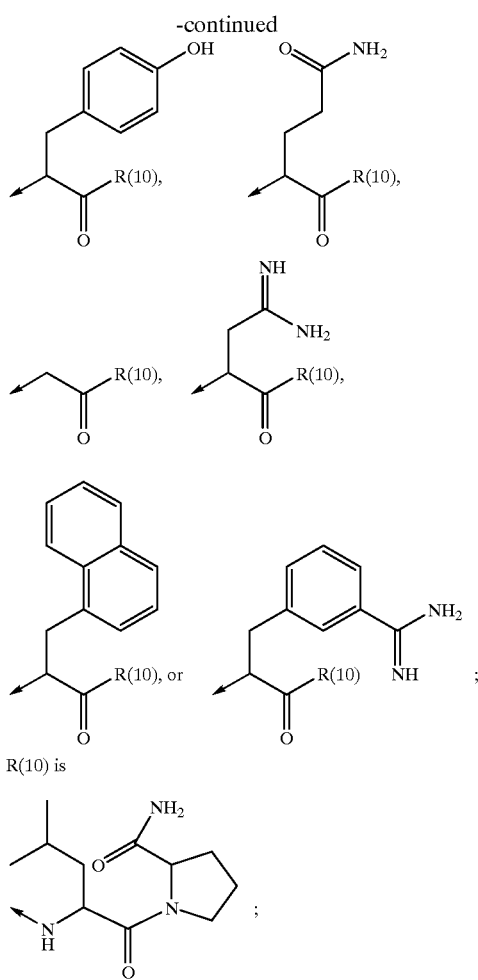

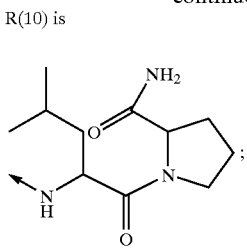

X⁻ is a physiologically acceptable anion;
an all stereoisomeric forms and physiologically acceptable salts thereof.

10. Compounds of the formula I as claimed in claim 8, wherein
R(1) is propyl or butyl;
R(2) is propyl or butyl;
R(3) is phenyl which is substituted by R(7);
R(4) is hydrogen;
R(5) is cyclohexyl;
R(6) is NR(8)R(9);
R(7) is amidino, or amino;
R(8) is hydrogen;

R(9) is

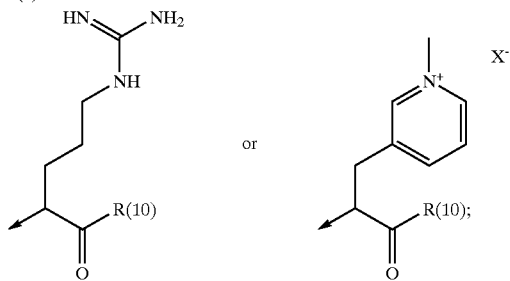

R(10) is

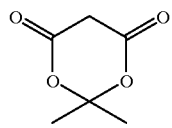

X⁻ is a physiologically acceptable anion;
an all stereoisomeric forms and physiologically acceptable salts thereof.

11. Compounds of the formula I as claimed in claim 10, wherein
R(1) is butyl.

12. Compounds of the formula I as claimed in claim 10, wherein
R(2) is butyl.

13. Compounds as claimed in claim 8, selected from the group consisting of:
2-(4-Carbamimidoyl-benzyl)-N-((S)-{1-(S)-[1-(S)-(2-(S)-carbamoyl-pyrrolidine-1-carbonyl)-3-methyl-butylcarbamoyl]-4-guanidino-butylcarbamoyl}-cyclohexyl-methyl)-N',N'-diisopropyl-malonamide trifluoroacetic acid salt, less polar diastereomer;

3-{2-(S)-{2-(S)-[3-(4-Carbamimidoyl-phenyl)-2-diisopropylcarbamoyl-propionylamino]-2-cyclohexyl-acetylamino}-2-[1-(S)-(2-(S)-carbamoyl-pyrrolidine-1-carbonyl)-3-methyl-butylcarbamoyl]-ethyl}-1-methyl-pyridinium trifluoro-acetate trifluoroacetic acid, less polar diastereomer, 2-(4-Amino-benzyl)-N-((S)-{1-(S)-[1-(S)-(2-(S)-carbamoyl-pyrrolidine-1-carbonyl)-3-methyl-butylcarbamoyl]-4-guanidino-butylcarbamoyl}-cyclohexyl-methyl)-N',N'-diisopropyl-malonamide trifluoroacetic acid salt, less polar diastereomer 2-(4-Carbamimidoyl-benzyl)-N-((S)-{1-(S)-[1-(S)-(2-(S)-carbamoyl-pyrrolidine-1-carbonyl)-3-methyl-butylcarbamoyl]-4-guanidino-butylcarbamoyl}-cyclohexyl-methyl)-N',N'-diisobutyl-malonamide trifluoroacetic acid salt, more polar diastereomer,
or their physiologically acceptable salts.

14. A process for the preparation of a compound of formula I as claimed in claim 1, which comprises
i)
a1) alkylating a compound of the formula III $$\underset{\underset{\phantom{x}}{}}{\text{III}}$$

with a compound of the formula IV,

LG—CH₂—R(3a)　　(IV)

wherein LG is a leaving group and wherein
R(3a) is (C₆–C₁₀)-aryl which is substituted by R(23);
R(23) is N(R(24))₂, nitro, or cyano;
R(24) is (C₁–C₆)-alkyl, (C₆–C₁₀)-aryl-(C₁–C₄)-alkyl, (C₁–C₆)-alkylcarbonyl, or (C₁–C₆)-alkoxycarbonyl;

in the presence of a base to give a compound of the formula V,

V

[structure IVa]

IVa or reacting a compound of the formula III with a compound of the formula IVa,

[structure of H-C(=O)-R(3a)]

in the presence of a reducing agent to geve a compound of the formula V;

b1) reacting a compound of the formula V with a compound of the formula VI,

[structure VI: R(1)-N(R(2))-H]

VI wherein R(1) and R2) are as claimed in claim 1, to give a compound of the formula VII;

[structure VII]

VII c1) coupling of a compound of the formula VII with a compound of the formula VIII,

[structure VIII]

VIII wherein R4) and R(5) are as claimed in claim 1 and R(25) is an easily cleavable ester to yield a compound of the formula IX,

[structure IX]

IX d1) optionally introducing an amidino group or reduction of a nitro group, by converting a compound of the formula IX into a compound of the formula X,

[structure X]

X wherein R(3) is as claimed in claim 1;

e1) saponification of the ester group R(25) and coupling the resulting compound A according to step c1) with a compound of the formula XII

HR(6)  (XII)

wherein R(6) is as claimed in claim 1 to give a compound of the formula 1; or c2) protecting the carboxylfunction in a compound of the formula VII with an easily cleavable protecting group and introducing an amidino group or reduction of a nitro group according to step d1) to give after deprotection of the carboxylfunction a compound of the formula XIII; and d2) coupling a compound of the formula XIII according to step c1)

[structure XIII]

XIII with a compound of formula XVI;

[structure XVI]

XVI to give a compound of the formula I; or ii)

a) coupling a compound of the formula XVIII,

[structure XVIII]

XVIII which is bound to a suitable carrier, and wherein

R(26) is hydrogen, —$CH_2$—R(17), 1-naphthylmethyl, —$(CH_2)3$—NR(28)—C(=N—R(27))-NH—R(28)

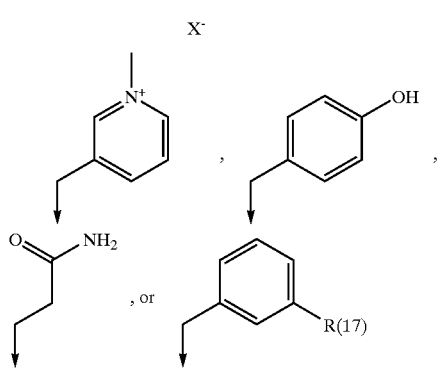

R(27) is R(28), cyano, hydroxy, $(C_1-C_6)$-alkoxy, $(C_6-C_{14})$-aryl-$(C_1-C_6)$-alkoxy which is unsubstituted or substituted in the aryl moiety, or amino;
R(28) is hydrogen, $(C_1-C_6)$-alkyl, or $(C_1-C_6)$-alkylcarbonyl;
and R(17) is as claimed in claim 1;
with a compound of the formula XVII

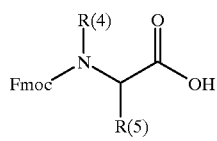

XVII wherein R4) and R(5) are as claimed in claim 1 to give a compound of the formula XIX

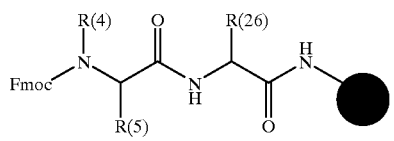

XIX b) and after deprotecting a compound of the formula XIX with a base coupling the deprotected compound XX to a compound of the formula VII or XIII to give a compound of the formula XXI or XXII;

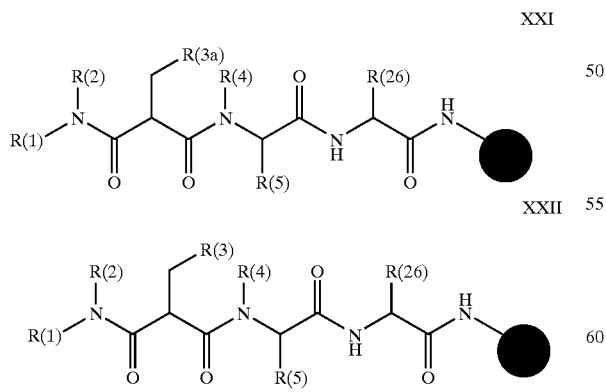

XXI

XXII c) optionally converting a compound of the formula XXI to a compound of formula XXII, and
d) cleaving a compound of the formula XXII off the resin to give a compound of the formula I.

15. A composition comprising at least one compound claimed in claim I and at least one pharmaceutically acceptable carrier.

16. A method of inhibiting factor Xa comprising administering to an individual in need thereof an effective amount of a compound as claimed in claim 1 for a time and under conditions effective to inhibit factor Xa.

17. A method of inhibiting blood clotting comprising administering to an individual in need thereof an effective amount of a compound as claimed in claim 1 for a time and under conditions effective to inhibit blood clotting.

18. A process for the preparation of a compound of formula I as claimed in claim 8, which comprises
i)
a1) alkylating a compound of the formula III

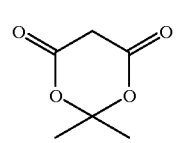

III with a compound of the formula IV,

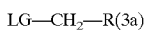
(IV)

wherein LG is a leaving group and wherein
R(3a) is $(C_6-C_{10})$-aryl which is substituted by R(23);
R(23) is $N(R(24))_2$, nitro, or cyano;
R(24) is $(C_1-C_6)$-alkyl, $(C_6-C_{10})$-aryl-$(C_1-C_4)$-alkyl, $(C_1-C_6)$-alkylcarbonyl, or $(C_1-C_6)$-alkoxycarbonyl;
in the presence of a base to give a compound of the formula V,

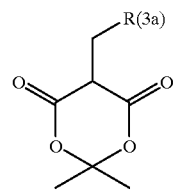

V or reacting a compound of the formula III with a compound of the formula IVa,

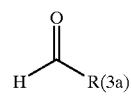

IVa in the presence of a reducing agent to give a compound of the formula V;
b1) reacting a compound of the formula V with a compound of the formula VI,

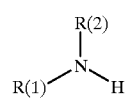

VI wherein R1) and R(2) are as claimed in claim 8, to give a compound of the formula VII;

VII

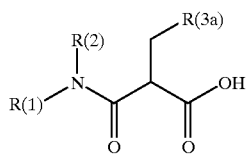

c1) coupling of a compound of the formula VII with a compound of the formula VIII,

VIII

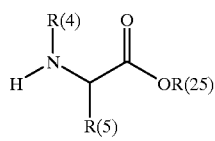

wherein R(4) and R(5) are as claimed in claim 8 and R(25) is an easily cleavable ester to yield a compound of the formula IX,

IX

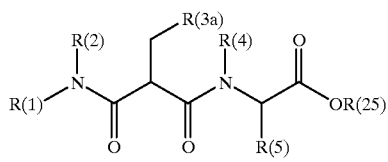

d1) optionally introducing an amidino group or reduction of a nitro group, by converting a compound of the formula IX into a compound of the formula X,

X

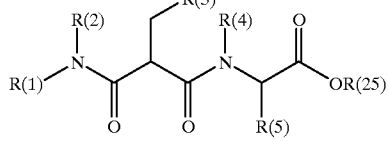

wherein R(3) is as claimed in claim 8;

e1) saponification of the ester group R(25) and coupling the resulting compound A according to step c1) with a compound of the formula XII HR(6)(XII)

HR(6)                        (XII)

wherein R(6) is as claimed in claim 8 to give a compound of the formula I; or c2) protecting the carboxylfunction in a compound of the formula VII with an easily cleavable protecting group and introducing an amidino group or reduction of a nitro group according to step d1) to give after deprotection of the carboxylfunction a compound of the formula XIII; and d2) coupling a compound of the formula XIII according to step c1)

XIII

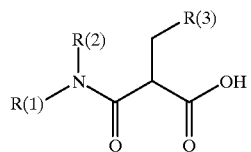

with a compound of formula XVI:

XVI

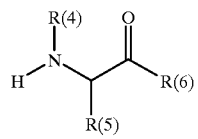

to give a compound of the formula 1; or ii)

a) coupling a compound of the formula XVIII,

XVIII

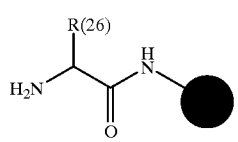

which is bound to a suitable carrier, and wherein R(26) is hydrogen, —CH₂—R(17), 1-naphthylmethyl, —(CH₂)₃—NR(28)—C(=N—R(27))-NH—R(28)

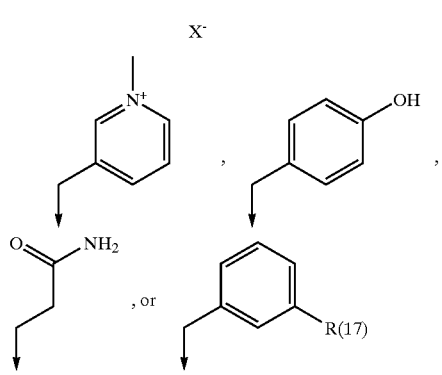

R(27) is R(28), cyano, hydroxy, $(C_1-C_6)$-alkoxy, $(C_6-C_{14})$-aryl-$(C_1-C_6)$-alkoxy which is unsubstituted or substituted in the aryl moiety, or amino;

R(28) is hydrogen, $(C_1-C_6)$-alkyl, or $(C_1-C_6)$-alkylcarbonyl; and R(17) is as claimed in claim 8;

with a compound of the formula XVII

XVII

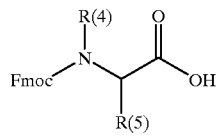

wherein R(4) and R(5) are as claimed in claim 8 to give a compound of the formula XIX

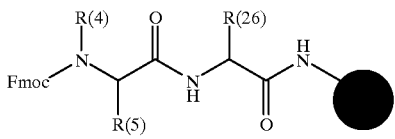

XIX b) and after deprotecting a compound of the formula XIX with a base coupling the deprotected compound XX to a compound of the formula VII or XIII to give a compound of the formula XXI or XXII;

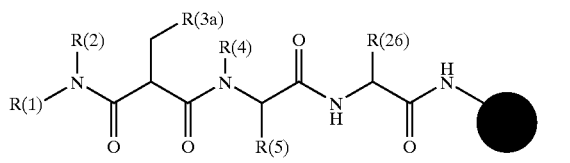

XXI

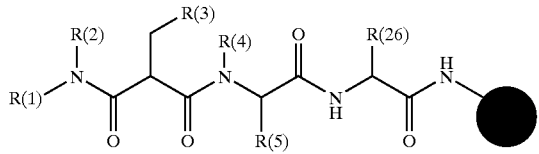

XXII c) optionally converting a compound of the formula XXI to a compound of formula XXII, and d) cleaving a compound of the formula XXII off the resin to give a compound of the formula I.

19. A composition xomprising at least one compound as claimed in claim 8 and at least one pharmaceutically acceptable carrier.

20. A method of inhibiting factor Xa comprising administering to an individual in need thereof an effective amount of a compound as claimed in claim 8 for a time and under consitions effective to inhibit factor Xa.

21. A method of inhibiting blood clotting comprising administering to an individual in need thereof an effective amount of a compound as claimed in claim 8 for a time and under conditions to inhibit blood clotting.

22. A method of reducing or inhibiting the coagulation of blood in a blood sample comprising contacting the blood with a compound according to claim 1 for a time and under conditions effective to inhibit factor Xa.

23. A method of reducing or inhibiting the coagulation of blood in a blood sample comprising contacting the blood with a compound according to claim 8 for a time and under conditions effective to inhibit factor Xa.

24. A mixture comprising at least two compounds according to claim 1.

25. A mixture comprising at least two compounds according to claim 2.

26. A mixture comprising at least two compounds according to claim 3.

27. A mixture comprising at least two compounds according to claim 4.

28. A mixture comprising at least two compounds according to claim 5.

29. A mixture comprising at least two compounds according to claim 8.

30. A mixture comprising at least two compounds according to claim 9.

31. A mixture comprising at least two compounds according to claim 10.

* * * * *

UNITED STATES PATENT AND TRADEMARK OFFICE
CERTIFICATE OF CORRECTION

PATENT NO. : 6,794,365 B2
DATED : September 21, 2004
INVENTOR(S) : Fahad A. Al-Obeidi, Armin Walser and Peter Wildgoose It is certified that error appears in the above-identified patent and that said Letters Patent is hereby corrected as shown below:

Title page,
Item [54], Title, "PREPARATION THEIR" should read -- PREPARATION, THEIR --.

Column 55,
Line 53, "($C_3$-C7)-cycloalkyl-($C_1$-C4)-alkyl;" should read -- ($C_3$-$C_7$)-cycloalkyl-($C_1$-$C_4$)-alkyl; --.

Column 56,
Line 2, "in" should read -- and --.

Column 60,
Line 26, "an" should read -- and --.
Line 31, delete "of the formula I".

Column 61,
Line 11, "2-(4-Carbamimidoyl-benzyl)-N-[(S)(1-(S)-carbamoyl-4-" should read -- 2-(4-Carbamimidoyl-benzyl)-N-[(S)-(1-(S)-carbamoyl-4- --.
Line 30, "2-(S)-{12-(S)-[3-(4-Carbamimidoyl-phenyl)-2-" should read -- 2-(S)-{2-(S)-[3-(4-Carbamimidoyl-phenyl)-2- --.
Line 54, "2-(4-Carbamimidoyl-benzyl)-N-[(S)-(1-(S)-carbamoyl4-" should read -- 2-(4-Carbamimidoyl-benzyl)-N-[(S)-(1-(S)-carbamoyl-4- --.

Column 62,
Line 62, "($C_3$-C7)-cycloalkyl, ($C_3$-C7)-" should read -- ($C_3$-$C_7$)-cycloalkyl, ($C_3$-$C_7$)- --.

Column 64,
Line 14, "an" should read -- and --.

Column 65,
Line 41, "an" should read -- and --.

Column 66,
Line 14, "an" should read -- and --.
Line 35, "2-(4-Amino-benzyl)-N-((S)- { 1 -(S)-[1-(S)-(2-(S)-" should read -- 2-(4-Amino-benzyl)-N-((S)-{l-(S)-[1-(S)-(2-(S) --.

Column 67,
Line 1, delete "V" and insert -- V -- on line 5 to the far right of the structure.
Line 11, delete "lVa" and insert -- IVa -- on line 14 to the far right of the structure.
Line 19, "geve" should read -- give --.

UNITED STATES PATENT AND TRADEMARK OFFICE
CERTIFICATE OF CORRECTION

PATENT NO. : 6,794,365 B2
DATED : September 21, 2004
INVENTOR(S) : Fahad A. AlObeidi, Armin Walser, and Peter Wildgoose It is certified that error appears in the above-identified patent and that said Letters Patent is hereby corrected as shown below:

Column 67 (cont'd),
Line 30, "R2)" should read -- R(2) --.
Line 52, "R4)" should read -- R(4) --.

Column 68,
Line 67, "-(CH$_2$)3-NR(28)-C(=N-R(27))-NH-R(28)" should read -- -(CH$_2$)$_3$-NR(28)-C(=N-R(27))-NH-R(28) --.

Column 69,
Line 32, "R4)" should read -- R(4) --.

Column 70,
Line 2, "claim I" should read -- claim 1 --.
Line 57, "bl)reacting" should read -- bl) reacting --.
Line 66, "R1)and" should read -- R(1) and --.

Column 71,
Line 51, after "formula XII" delete "HR(6)(XII)".

Column 72,
Line 20, "formula 1;" should read -- formula I; --.

Column 74,
Line 1, "xomprising" should read -- comprising --.
Line 7, "consitions" should read -- conditions --.

Signed and Sealed this

Nineteenth Day of April, 2005

JON W. DUDAS
*Director of the United States Patent and Trademark Office*

UNITED STATES PATENT AND TRADEMARK OFFICE
CERTIFICATE OF CORRECTION

PATENT NO.    : 6,794,365 B2
DATED         : September 21, 2004
INVENTOR(S)   : Fahad A. Al-Obeidi, Armin Walser and Peter Wildgoose It is certified that error appears in the above-identified patent and that said Letters Patent is hereby corrected as shown below:

Title page,
Item [54], Title, "PREPARATION THEIR" should read
-- PREPARATION, THEIR --.

Column 55,
Line 53, "$(C_3-C7)$-cycloalkyl-$(C_1-C_4)$-alkyl;" should read -- $(C_3-C_7)$-cycloalkyl-$(C_1-C_4)$-alkyl; --.

Column 56,
Line 2, "in" should read -- and --.

Column 60,
Line 26, "an" should read -- and --.
Line 31, delete "of the formula I".

Column 61,
Line 11, "2-(4-Carbamimidoyl-benzyl)-N-[(S)(1-(S)-carbamoyl-4-" should read
-- 2-(4-Carbamimidoyl-benzyl)-N-[(S)-(1-(S)-carbamoyl-4- --.
Line 30, "2-(S)-{12-(S)-[3-(4-Carbamimidoyl-phenyl)-2-" should read
-- 2-(S)-{2-(S)-[3-(4-Carbamimidoyl-phenyl)-2- --.
Line 54, "2-(4-Carbamimidoyl-benzyl)-N-[(S)-(1-(S)-carbamoyl4-" should read
-- 2-(4-Carbamimidoyl-benzyl)-N-[(S)-(1-(S)-carbamoyl-4- --.

Column 62,
Line 62, "$(C_3-C7)$-cycloalkyl, $(C_3-C7)$-" should read
-- $(C_3-C_7)$-cycloalkyl, $(C_3-C_7)$- --.

Column 64,
Line 14, "an" should read -- and --.

Column 65,
Line 41, "an" should read -- and --.

Column 66,
Line 14, "an" should read -- and --.
Line 35, "2-(4-Amino-benzyl)-N-((S)-{1 -(S)-[1-(S)-(2-(S)-" should read -- 2-(4-Amino-benzyl)-N-((S)-{1-(S)-[1-(S)-(2-(S)- --.

Column 67,
Line 1, delete "V".
Line 5, insert -- V -- to the far right of the structure.
Line 11, delete "IVa".

UNITED STATES PATENT AND TRADEMARK OFFICE
CERTIFICATE OF CORRECTION

PATENT NO.    : 6,794,365 B2
DATED         : September 21, 2004
INVENTOR(S)   : Fahad A. Al-Obeidi, Armin Walser and Peter Wildgoose It is certified that error appears in the above-identified patent and that said Letters Patent is hereby corrected as shown below:

Column 67 (cont'd),
Line 14, insert -- IVa -- to the far right of the structure.
Line 19, "geve" should read -- give --.
Line 30, "R2)" should read -- R(2) --.

Column 68,
Line 67, "-(CH$_2$)3-NR(28)-C(=N-R(27))-NH-R(28)" should read
-- -(CH$_2$)$_3$-NR(28)-C(=N-R(27))-NH-R(28) --.

Column 69,
Line 32, "R4)" should read -- R(4) --.

Column 70,
Line 2, "claim I" should read -- claim 1 --.
Line 57, "b1)reacting" should read -- b1) reacting --.
Line 66, "R1)and" should read -- R(1) and --.

Column 71,
Line 51, after "formula XII" delete "HR(6)(XII)".

Column 72,
Line 20, "formula 1;" should read -- formula I; --.

Column 74,
Line 1, "xomprising" should read -- comprising --.
Line 7, "consitions" should read -- conditions --.

Signed and Sealed this

Fourth Day of April, 2006

JON W. DUDAS
*Director of the United States Patent and Trademark Office*